US 8,268,778 B2

(12) United States Patent
McLinden et al.

(10) Patent No.: US 8,268,778 B2
(45) Date of Patent: Sep. 18, 2012

(54) FLAVIVIRUS NS5A PROTEINS FOR THE TREATMENT OF HIV

(75) Inventors: James McLinden, Coralville, IA (US); Jinhua Xiang, Iowa City, IA (US); Jack T. Stapleton, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 337 days.

(21) Appl. No.: 12/532,064

(22) PCT Filed: Mar. 20, 2008

(86) PCT No.: PCT/US2008/057719
§ 371 (c)(1),
(2), (4) Date: Jan. 6, 2010

(87) PCT Pub. No.: WO2008/127840
PCT Pub. Date: Oct. 23, 2008

(65) Prior Publication Data
US 2010/0143454 A1    Jun. 10, 2010

Related U.S. Application Data

(60) Provisional application No. 60/896,454, filed on Mar. 22, 2007, provisional application No. 60/947,836, filed on Jul. 3, 2007.

(51) Int. Cl.
*A01N 37/18* (2006.01)
*A61K 38/00* (2006.01)
*A61P 31/18* (2006.01)
(52) U.S. Cl. .......................................... 514/3.8; 514/3.9
(58) Field of Classification Search .................. None
See application file for complete search history.

(56) References Cited

FOREIGN PATENT DOCUMENTS

| WO | WO 2004/108159 | 12/2004 |
|---|---|---|
| WO | WO 2006/088664 | 8/2006 |

OTHER PUBLICATIONS

Chang et al. Expression of GB virus C NS5A protein from genotypes 1, 2, 3, 5 and a 30 aa NS5A fragment inhibit human immunodeficiency virus type 1 replication in a CD4+ T-lymphocyte cell line. Journal of General Virology. 2007. vol. 88, pp. 3341-3346.*
Bjorkman et al., "GB virus C during the natural course of HIV-1 infection: viremia at diagnosis does not predict mortality," *AIDS*, 18:877-86, 2004.
Dawson et al., "Prevalence studies of GB virus-C infection using reverse transcriptase-polymerase chain reaction," *J. Med. Virol.*, 50:97-103, 1996.
Fogeda et al., "In vitro infection of human peripheral blood mononuclear cells by GB virus C/Hepatitis G virus," *J. Virol.*, 73:4052-4061, 1999.
Jung et al., "Inhibition of HIV strains by GB virus C in cell culture can be mediated by CD4 and CD8 T-lymphocyte derived soluble factors," *AIDS*, 19:12567-12572, 2005.
Lefère et al., "Carriage of GB virus C/hepatitis G virus RNA is associated with a slower immunologic, virologic, and clinical progression of human immunodeficiency virus disease in coinfected persons," *J. Infect. Dis.*, 179:783-789, 1999.
Nunnari et al., "Slower progression of HIV-1 infection in persons with GB virus C co-infection correlates with an intact T-helper 1 cytokine profile," *Ann. Int. Med.*, 139:26-30, 2003.
PCT International Preliminary Report on Patentability, issued in International application No. PCT/US2008/057719, mailed Oct. 1, 2009.
Sabin et al., "Effects of coinfection with hepatitis G virus on HIV disease progression in hemophilic men," *J. Acquir. Immune Defic. Syndr.*, 19:546-547, 1998.
Stapleton et al. "Evidence for delayed human immunodeficiency virus (HIV) disease progression in HIV-GB virus C co-infected individuals," In: *Viral Hepatitis and Liver Disease*, H. Margolis and Fields, H.A., editors, Lipincott, London, pp. 473-476, 2004.
Stapleton et al., "GB virus type C: a beneficial infection?" *J. Clin. Microbiol.*, 42:3915-3919, 2004.
Thomas et al., "Association of antibody to GB virus C (hepatitis G virus) with viral clearance and protection from reinfection,"*J. Infect. Dis.*, 177:539-542, 1998.
Toyoda et al., "Effect of GB virus C/hepatitis G virus coinfection on the course of HIV infection in hemophilia patients in Japan," *J. Acquir. Immune Defic. Syndr.*, 17:209-213, 1998.
Wunschmann et al., "Characterization of hepatitis C virus (HCV) and HCV E2 interactions with CD81 and the low-density lipoprotein receptor," *J. Virol.*, 74:10055-10062, 2000.
Xiang et al., "An 85-aa segment of the GB virus type C NS5A phosphoprotein inhibits HIV-1 replication in CD4+ Jurkat T cells," *Proc. Nat'l Acad. Sci USA*, 103:15570-15575, 2006.
Xiang et al., "Characterization of a peptide domain within the GB virus C NS5A phosphoprotein that inhibits HIV replication," *PLoS One*, 3(7):e2580, 2008.
Xiang et al., "Effect of coinfection with GB virus C on survival among patients with HIV infection," *N. Engl. J. Med.*, 345:707-714, 2001.
Xiang et al., "GB virus type C NS5A sequence polymorphisms: association with interferon susceptibility and inhibition of PKR-mediated eIF2alpha phosphorylation," *J. Interferon Cytokin Res.*, 25:261-270, 2005.
Xiang et al., "Inhibition of HIV-1 replication by GB virus C infection through increases in RANTES, MIP-1alpha, MIP-1beta, and SDF-1," *Lancet*, 363:2040-2046, 2004.
Xiang et al., "South African GB virus C isolates: interactions between genotypes 1 and 5 isolates and HIV," *J. Infect. Dis.*, 192:2147-2151, 2005.
Zhang et al., "Effect of early and late GB virus C viraemia on survival of HIV-infected individuals: a meta-analysis," *HIV Med.*, 7:173-80, 2006.

* cited by examiner

*Primary Examiner* — Marcela M Cordero Garcia
(74) *Attorney, Agent, or Firm* — Parker Highlander, PLLC

(57) ABSTRACT

GB virus C (GBV-C or hepatitis G virus) is a flavivirus that frequently leads to chronic viremia in humans. The invention provides compositions and methods involving a -GBV-C NS5A peptide or polypeptide for inhibiting and treating HIV infections.

41 Claims, 32 Drawing Sheets

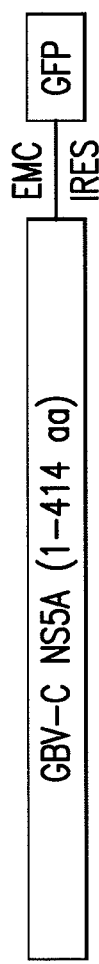
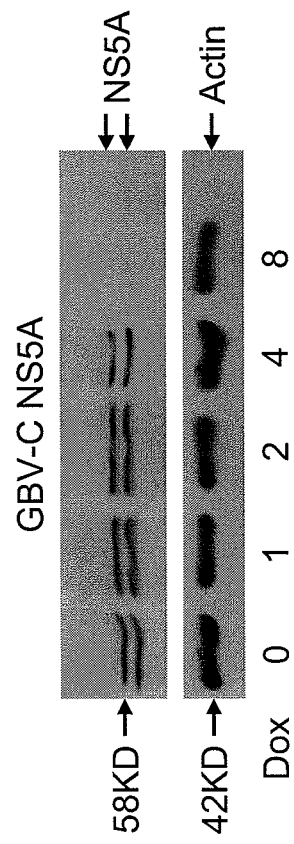
FIG. 3A
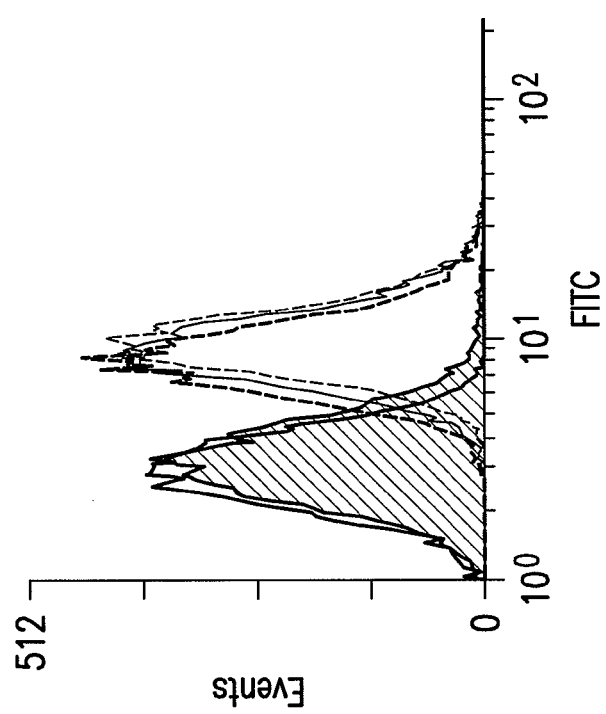
FIG. 3C
FIG. 3B

| Gene Name | Fold Change | p value |
|---|---|---|
| IL8 | −25.11 | 0.0007 |
| CXCL11 | −17.03 | 0.0009 |
| CCRL2 | −15.03 | 0.0017 |
| CCR8 | −4.90 | 0.0002 |
| IL18 | −2.78 | 0.0003 |
| TLR2 | −2.39 | 0.0086 |
| CXCR4 | −1.32 | 0.0489 |
| CXCL12 (SDF-1) | 1.47 | (high CT) |
| CCR4 | 4.72 | 0.0301 |
| TNF | 37.79 | 0.0013 |

FIG.7

| Gene | Fold Change | p value |
|------|-------------|---------|
| CD80 | -5.8 | 0.006 |
| CCR2 | -4.0 | 0.014 |
| IL10 | -3.1 | 0.004 |
| ICOS | -2.3 | 0.005 |
| IL13 | -2.1 | 0.045 |
| IL4 | -1.7 | 0.039 |
| STAT4 | -1.7 | 0.040 |
| STAT6 | -1.6 | 0.010 |

| Gene | Fold Change | p value |
|------|-------------|---------|
| FASLG | 4.0 | 0.0035 |
| IL13RA | 4.2 | 0.0974 |
| TBX21 | 6.9 | 0.0151 |
| CD69 | 9.2 | 0.0408 |
| IRF4 | 12.9 | 0.0107 |
| IL4R | 15.3 | 0.0062 |
| TNF | 16.6 | 0.0963 |
| IL18R1 | 19.2 | 0.0096 |

FIG.12

| Gene Name | Fold Change | p value |
|---|---|---|
| CASP1 | −17.3 | 0.017 |
| CD40LG | −4.53 | 0.019 |
| TNFRSF7 | −3.31 | 0.013 |
| BIRC1 | −2.23 | 0.006 |
| DAPK1 | −1.87 | 0.046 |
| TNFRSF25 | 2.44 | 0.018 |
| GADD45A | 2.63 | 0.012 |
| BCL2 | 5.63 | <0.001 |
| TNF | 37.79 | 0.001 |
| TNFSF7 | 186.7 | <0.001 |

FIG.13

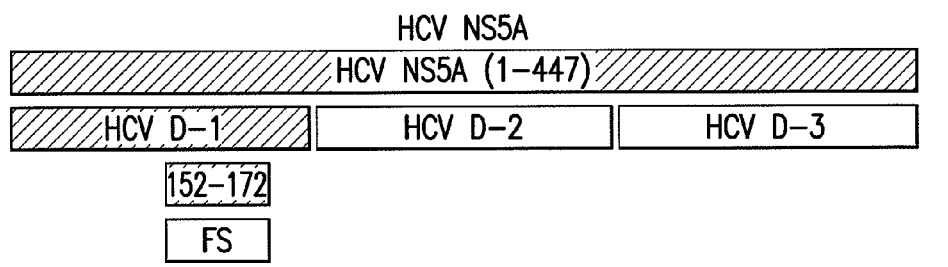
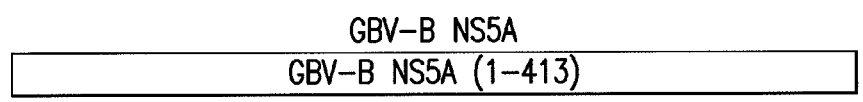
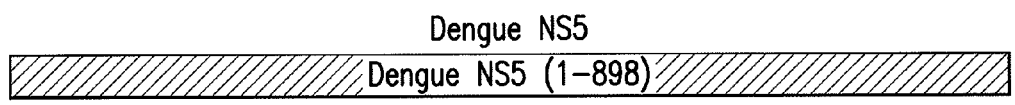
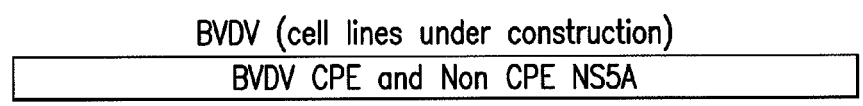
FIG. 16

| GBV-C | GT | |
|---|---|---|
| AF121950 | 2 | VDG IPVSWD ADARA P A |
| AF196904 | 2 | VDG IPVSWD ADARA P A |
| AB003288 | 4 | VDG IPVSWE ADARA P A |
| AB003290 | 3 | VDG IPVSWE ADARA P A |
| AB003291 | 1 | VDG IPVSWD ADARA P A |
| AB003292 | 4 | VDG IPVSWE ADARA P A |
| AB013500 | 1 | VDG IPVSWE ADARA P A |
| AB013501 | 3 | VDG IPVSWE ADARA P A |
| D090600 | 2 | VDG IPVSWD ADARA P A |
| U-75356 | 2 | VDG IPVSWE ADARA P A |
| AY949771 | 5 | VDG IPVSWD ADARA P A |
| HCV 1A | | LDG VRLHRF APPCK P LLREEV |
| HCV 1B | | VDG VRLHRY APPCR P LLREEV |
| HCV 2A | | VDG VQIHRF APIPK P FFRDEV |
| HCV 3A | | VDG VRLHRY APPCK P LLREEI |
| CONSENSUS | | DG     A    P |

FIG.17

HIV (X4) superinfection of YFV infected PBMCs

FIG.24A

HIV (R5) superinfection of YFV infected PBMCs

FIG.24B

SEQUENCE LISTING

```
<160> NUMBER OF SEQ ID NOS: 26

<210> SEQ ID NO 1
<211> LENGTH: 9377
<212> TYPE: DNA
<213> ORGANISM: Hepatitis GB virus C
<220> FEATURE:
<221> NAME/KEY: CDS
<222> LOCATION: (534)..(9065)

<400> SEQUENCE: 1
cccccccccc ggcactgggt gcaagcccca gaaaccgacg cctactgaag tagacgtaat      60
ggccccgcgc cgaaccggcg accggccaaa aggtggtgga tgggtgatga cagggttggt     120
aggtcgtaaa tcccggtcat cctggtagcc actataggtg ggtcttaagg ggaggctacg     180
gtccctcttg cgcatatgga ggaaaagcgc acggtccaca ggtgttggtc ctaccggtgt     240
aataaggacc cggcgctagg cacgccgtta aaccgagccc gttactcccc tgggcaaacg     300
acgcccacgt acggtccacg tcgcccttca atgtctctct tgaccaatag gcgtagccgg     360
cgagttgaca aggaccagtg ggggccggc gggaggggga aggaccccca ccgctgccct      420
tcccggggag gcgggaaatg catggggcca cccagctccg cggcggccta cagccgggt     480 agcccaagaa ccttcgggtg agggcgggtg gcatttcttt tcctataccg atc atg        536
                                                           Met
                                                            1 gca gtc ctt ctg ctc cta ctc gtg gtg gag gcc ggg gct att tta gcc      584
Ala Val Leu Leu Leu Leu Leu Val Val Glu Ala Gly Ala Ile Leu Ala
        5                  10                  15
```

| | | | | | | | | | | | | | | | | |
|---|---|---|---|---|---|---|---|---|---|---|---|---|---|---|---|---|
| ccg | gcc | acc | cat | gct | tgt | agc | gcg | aaa | ggg | caa | tat | tts | ctc | aca | aac | 632 |
| Pro | Ala | Thr | His | Ala | Cys | Ser | Ala | Lys | Gly | Gln | Tyr | Xaa | Leu | Thr | Asn | |
| | | 20 | | | | 25 | | | | 30 | | | | | | |
| tgt | tgc | gcc | ctg | gag | gac | ata | ggc | ttc | tgc | ctg | gag | ggc | gga | tgc | ctg | 680 |
| Cys | Cys | Ala | Leu | Glu | Asp | Ile | Gly | Phe | Cys | Leu | Glu | Gly | Gly | Cys | Leu | |
| | 35 | | | | 40 | | | | 45 | | | | | | | |
| gtg | gct | ctg | ggg | tgc | acc | att | tgc | acc | gac | cgc | tgc | tgg | cca | ctg | tat | 728 |
| Val | Ala | Leu | Gly | Cys | Thr | Ile | Cys | Thr | Asp | Arg | Cys | Trp | Pro | Leu | Tyr | |
| 50 | | | | 55 | | | | 60 | | | | 65 | | | | |
| cag | gcg | ggt | ttg | gcc | gtg | cgg | ccc | ggc | aag | tcc | gcc | gcc | cag | ttg | gtg | 776 |
| Gln | Ala | Gly | Leu | Ala | Val | Arg | Pro | Gly | Lys | Ser | Ala | Ala | Gln | Leu | Val | |
| | | 70 | | | | 75 | | | | 80 | | | | | | |
| ggg | gaa | ctc | ggt | agt | ctc | tac | ggg | ccc | ttg | tcg | gtc | tcg | gct | tat | gtg | 824 |
| Gly | Glu | Leu | Gly | Ser | Leu | Tyr | Gly | Pro | Leu | Ser | Val | Ser | Ala | Tyr | Val | |
| | 85 | | | | 90 | | | | 95 | | | | | | | |
| gcc | ggg | atc | ctg | ggg | ctt | ggg | gag | gtc | tac | tcg | ggg | gtc | ctc | acc | gtc | 872 |
| Ala | Gly | Ile | Leu | Gly | Leu | Gly | Glu | Val | Tyr | Ser | Gly | Val | Leu | Thr | Val | |
| 100 | | | | 105 | | | | 110 | | | | | | | | |
| ggg | gtg | gcg | ttg | acg | cgc | agg | gtc | tac | ccg | gtc | ccg | aac | ctg | acg | tgt | 920 |
| Gly | Val | Ala | Leu | Thr | Arg | Arg | Val | Tyr | Pro | Val | Pro | Asn | Leu | Thr | Cys | |
| 115 | | | | 120 | | | | 125 | | | | | | | | |
| gca | gta | gag | tgt | gag | ttg | aag | tgg | gaa | agt | gag | ttt | tgg | aga | tgg | act | 968 |
| Ala | Val | Glu | Cys | Glu | Leu | Lys | Trp | Glu | Ser | Glu | Phe | Trp | Arg | Trp | Thr | |
| 130 | | | | 135 | | | | 140 | | | | 145 | | | | |
| gaa | cag | ctg | gcc | tca | aac | tac | tgg | att | ctg | gaa | tac | ctc | tgg | aag | gtg | 1016 |
| Glu | Gln | Leu | Ala | Ser | Asn | Tyr | Trp | Ile | Leu | Glu | Tyr | Leu | Trp | Lys | Val | |
| | | 150 | | | | 155 | | | | 160 | | | | | | |
| cct | ttc | gac | ttt | tgg | cgg | gga | gtg | atg | agc | ctt | act | cct | ctc | ttg | gtg | 1064 |
| Pro | Phe | Asp | Phe | Trp | Arg | Gly | Val | Met | Ser | Leu | Thr | Pro | Leu | Leu | Val | |
| | 165 | | | | 170 | | | | 175 | | | | | | | |
| tgc | gtg | gcg | gcc | ctc | ctc | ctg | ctg | gag | cag | cgt | att | gtc | atg | gtc | ttc | 1112 |
| Cys | Val | Ala | Ala | Leu | Leu | Leu | Leu | Glu | Gln | Arg | Ile | Val | Met | Val | Phe | |
| 180 | | | | 185 | | | | 190 | | | | | | | | |
| ctc | ctg | gtc | act | atg | gcg | ggc | atg | tca | caa | ggc | gcg | ccc | gcc | tca | gtg | 1160 |
| Leu | Leu | Val | Thr | Met | Ala | Gly | Met | Ser | Gln | Gly | Ala | Pro | Ala | Ser | Val | |
| 195 | | | | 200 | | | | 205 | | | | | | | | |
| ttg | ggg | tca | cgg | cct | ttc | gag | gcc | ggg | ttg | act | tgg | cag | tct | tgt | tct | 1208 |
| Leu | Gly | Ser | Arg | Pro | Phe | Glu | Ala | Gly | Leu | Thr | Trp | Gln | Ser | Cys | Ser | |
| 210 | | | | 215 | | | | 220 | | | | 225 | | | | |
| tgc | agg | tcg | aac | ggg | tcc | cgc | gtg | ccg | acg | ggg | gag | agg | gtt | tgg | gaa | 1256 |
| Cys | Arg | Ser | Asn | Gly | Ser | Arg | Val | Pro | Thr | Gly | Glu | Arg | Val | Trp | Glu | |
| | | 230 | | | | 235 | | | | 240 | | | | | | |
| cgt | ggg | aac | gtc | aca | ctt | ttg | tgt | gac | tgc | ccc | aac | ggt | cct | tgg | gtg | 1304 |
| Arg | Gly | Asn | Val | Thr | Leu | Leu | Cys | Asp | Cys | Pro | Asn | Gly | Pro | Trp | Val | |
| | 245 | | | | 250 | | | | 255 | | | | | | | |
| tgg | gtc | ccg | gcc | ctt | tgc | cag | gca | atc | gga | tgg | ggc | gac | cct | atc | act | 1352 |
| Trp | Val | Pro | Ala | Leu | Cys | Gln | Ala | Ile | Gly | Trp | Gly | Asp | Pro | Ile | Thr | |
| 260 | | | | 265 | | | | 270 | | | | | | | | |
| cat | tgg | agc | cac | gga | caa | aat | cag | tgg | ccc | ctt | tct | tgt | ccc | caa | ttt | 1400 |
| His | Trp | Ser | His | Gly | Gln | Asn | Gln | Trp | Pro | Leu | Ser | Cys | Pro | Gln | Phe | |
| 275 | | | | 280 | | | | 285 | | | | | | | | |
| gtc | tac | ggc | gcc | gtt | tca | gtg | acc | tgc | gtg | tgg | ggt | tct | gtg | tct | tgg | 1448 |
| Val | Tyr | Gly | Ala | Val | Ser | Val | Thr | Cys | Val | Trp | Gly | Ser | Val | Ser | Trp | |
| 290 | | | | 295 | | | | 300 | | | | 305 | | | | |
| ttt | gct | tcc | act | ggg | ggt | cgc | gac | tcc | aag | gtt | gat | gtg | tgg | agt | ttg | 1496 |
| Phe | Ala | Ser | Thr | Gly | Gly | Arg | Asp | Ser | Lys | Val | Asp | Val | Trp | Ser | Leu | |
| | | 310 | | | | 315 | | | | 320 | | | | | | |
| gtt | cca | gtt | ggc | tct | gcc | agc | tgc | acc | ata | gcc | gca | ctg | gga | tct | tcg | 1544 |
| Val | Pro | Val | Gly | Ser | Ala | Ser | Cys | Thr | Ile | Ala | Ala | Leu | Gly | Ser | Ser | |
| | 325 | | | | 330 | | | | 335 | | | | | | | |

```
gat cgc gac aca gtg gtt gag ctc tcc gag tgg gga att ccc tgc gcc      1592
Asp Arg Asp Thr Val Val Glu Leu Ser Glu Trp Gly Ile Pro Cys Ala
        340                 345                 350 act tgt atc ctg gac agg cgg cct gcc tcg tgt ggc acc tgt gtg agg      1640
Thr Cys Ile Leu Asp Arg Arg Pro Ala Ser Cys Gly Thr Cys Val Arg
355                 360                 365 gac tgc tgg ccc gag acc ggg tcg gta cgt ttc cca ttc cac agg tgt      1688
Asp Cys Trp Pro Glu Thr Gly Ser Val Arg Phe Pro Phe His Arg Cys
370                 375                 380                 385 ggc gcg gga ccg agg ctg acc aga gac ctt gag gct gtg ccc ttc gtc      1736
Gly Ala Gly Pro Arg Leu Thr Arg Asp Leu Glu Ala Val Pro Phe Val
                390                 395                 400 aat agg aca act ccc ttc acc ata agg ggg ccc ctg ggc aac cag ggg      1784
Asn Arg Thr Thr Pro Phe Thr Ile Arg Gly Pro Leu Gly Asn Gln Gly
            405                 410                 415 cga ggc aac ccg gtg cgg tcg ccc ttg ggt ttt ggg tcc tac acc atg      1832
Arg Gly Asn Pro Val Arg Ser Pro Leu Gly Phe Gly Ser Tyr Thr Met
        420                 425                 430 acc aag atc cga gac tcc tta cac ttg gtg aaa tgt ccc acc cca gcc      1880
Thr Lys Ile Arg Asp Ser Leu His Leu Val Lys Cys Pro Thr Pro Ala
    435                 440                 445 att gag cct ccc acc gga acg ttt ggg ttc ttc cca gga gtc ccc ccc      1928
Ile Glu Pro Pro Thr Gly Thr Phe Gly Phe Phe Pro Gly Val Pro Pro
450                 455                 460                 465 ctt aac aac tgc atg ctt ctc ggc act gag gtg tca gag gta ttg ggt      1976
Leu Asn Asn Cys Met Leu Leu Gly Thr Glu Val Ser Glu Val Leu Gly
                470                 475                 480 ggg gcg ggc ctc act ggg ggg ttt tac gaa cct ctg gtg cgg cgg tgt      2024
Gly Ala Gly Leu Thr Gly Gly Phe Tyr Glu Pro Leu Val Arg Arg Cys
            485                 490                 495 tca gag ctg atg ggt cgg cgg aat ccg gtc tgc ccg ggg ttt gca tgg      2072
Ser Glu Leu Met Gly Arg Arg Asn Pro Val Cys Pro Gly Phe Ala Trp
        500                 505                 510 ctc tct tcg gga cgg cct gat ggg ttc ata cat gtt cag ggc cac ttg      2120
Leu Ser Ser Gly Arg Pro Asp Gly Phe Ile His Val Gln Gly His Leu
515                 520                 525 cag gag gtg gat gcg ggc aac ttc att ccg ccc cca cgc tgg ttg ctc      2168
Gln Glu Val Asp Ala Gly Asn Phe Ile Pro Pro Pro Arg Trp Leu Leu
530                 535                 540                 545 ttg gac ttt gta ttt gtc ctg tta tac ctg atg aag ctg gca gag gca      2216
Leu Asp Phe Val Phe Val Leu Leu Tyr Leu Met Lys Leu Ala Glu Ala
                550                 555                 560 cgg ttg gtc ccg ctg atc ctc ctc cta tgg tgg tgg gtg aac cag          2264
Arg Leu Val Pro Leu Ile Leu Leu Leu Trp Trp Trp Val Asn Gln
            565                 570                 575 ttg gcg gtc ctt gkt gtg scg gct gck crc gcc gcc gtg gct gga gag      2312
Leu Ala Val Leu Xaa Val Xaa Ala Ala Xaa Ala Ala Val Ala Gly Glu
        580                 585                 590 gtg ttt gcg ggc cct gcc ttg tcc tgg tgt ctg ggc cta ccc ttc gtg      2360
Val Phe Ala Gly Pro Ala Leu Ser Trp Cys Leu Gly Leu Pro Phe Val
595                 600                 605 agt atg atc ctg ggg cta gca aac ctg gtg ttg tac ttc cgc tgg atg      2408
Ser Met Ile Leu Gly Leu Ala Asn Leu Val Leu Tyr Phe Arg Trp Met
610                 615                 620                 625 ggt cct caa cgc ctg atg ttc ctc gtg ttg tgg aag ctc gct cgg ggg      2456
Gly Pro Gln Arg Leu Met Phe Leu Val Leu Trp Lys Leu Ala Arg Gly
                630                 635                 640 gct ttc ccg ctg gca tta ctg atg ggg att tcc gcc act cgc ggc cgc      2504
Ala Phe Pro Leu Ala Leu Leu Met Gly Ile Ser Ala Thr Arg Gly Arg
            645                 650                 655
```

```
acc tct gtg ctt ggc gcc gaa ttc tgc ttt gat gtc acc ttt gaa gtg     2552
Thr Ser Val Leu Gly Ala Glu Phe Cys Phe Asp Val Thr Phe Glu Val
        660                 665                 670 gac acg tca gtc ttg ggt tgg gtg gtt gct agt gtg gtg gct tgg gcc     2600
Asp Thr Ser Val Leu Gly Trp Val Val Ala Ser Val Val Ala Trp Ala
675                 680                 685 ata gcg ctc ctg agc tct atg agc gcg ggg ggg tgg aag cac aaa gcc     2648
Ile Ala Leu Leu Ser Ser Met Ser Ala Gly Gly Trp Lys His Lys Ala
690                 695                 700                 705 ata atc tat agg acg tgg tgt aaa ggg tac cag gcy ctt cgc cag cgc     2696
Ile Ile Tyr Arg Thr Trp Cys Lys Gly Tyr Gln Ala Leu Arg Gln Arg
        710                 715                 720 gtg gtg cgt agc ccc ctc ggg gag ggg cgg ccc acc aag ccg ctg acg     2744
Val Val Arg Ser Pro Leu Gly Glu Gly Arg Pro Thr Lys Pro Leu Thr
        725                 730                 735 ata gcc tgg tgt ctg gcc tct tac atc tgg ccg gac gct gtg atg ttg     2792
Ile Ala Trp Cys Leu Ala Ser Tyr Ile Trp Pro Asp Ala Val Met Leu
        740                 745                 750 gtg gtt gtg gcc atg gtc ctc ctc ttc ggc ctt ttc gac gcg ctc gat     2840
Val Val Val Ala Met Val Leu Leu Phe Gly Leu Phe Asp Ala Leu Asp
        755                 760                 765 tgg gcc ttg gag gag ctc ctt gtg tcg cgg cct tcg ttg cgt cgt ttg     2888
Trp Ala Leu Glu Glu Leu Leu Val Ser Arg Pro Ser Leu Arg Arg Leu
770                 775                 780                 785 gca agg gtg gtg gag tgt tgt gtg atg gcg ggc gag aag gcc act acc     2936
Ala Arg Val Val Glu Cys Cys Val Met Ala Gly Glu Lys Ala Thr Thr
                790                 795                 800 gtc cgg ctt gtg tcc aag atg tgc gcg aga ggg gcc tac ctg ttt gac     2984
Val Arg Leu Val Ser Lys Met Cys Ala Arg Gly Ala Tyr Leu Phe Asp
        805                 810                 815 cac atg ggg tcg ttc tcg cgc gcg gtc aag gag cgc ttg ctg gag tgg     3032
His Met Gly Ser Phe Ser Arg Ala Val Lys Glu Arg Leu Leu Glu Trp
            820                 825                 830 gac gcg gct ttg gag mcc ctg tca ttc act agg acg gac tgt cgc atc     3080
Asp Ala Ala Leu Glu Xaa Leu Ser Phe Thr Arg Thr Asp Cys Arg Ile
835                 840                 845 ata cga gac gcc gcc agg acc ctg agc tgc ggc caa tgc gtc atg ggc     3128
Ile Arg Asp Ala Ala Arg Thr Leu Ser Cys Gly Gln Cys Val Met Gly
850                 855                 860                 865 ttg ccc gtg gtg gct agg cgc ggc gat gag gtc ctg att ggg gtc ttt     3176
Leu Pro Val Val Ala Arg Arg Gly Asp Glu Val Leu Ile Gly Val Phe
                870                 875                 880 cag gat gtg aac cac ttg cct ccg ggg ttt gyt cct aca gcg cct gtt     3224
Gln Asp Val Asn His Leu Pro Pro Gly Phe Xaa Pro Thr Ala Pro Val
        885                 890                 895 gtc atc cgt cgg tgc gga aag ggc ttc ctc ggg gtc act aag gct gcc     3272
Val Ile Arg Arg Cys Gly Lys Gly Phe Leu Gly Val Thr Lys Ala Ala
        900                 905                 910 ttg act ggt cgg gat cct gac tta cac cca gga aac gtc atg gtt ttg     3320
Leu Thr Gly Arg Asp Pro Asp Leu His Pro Gly Asn Val Met Val Leu
        915                 920                 925 ggg acg gct acc tcg cgc agc atg gga acg tgc tta aac ggg ttg ctg     3368
Gly Thr Ala Thr Ser Arg Ser Met Gly Thr Cys Leu Asn Gly Leu Leu
930                 935                 940                 945 ttc acg aca ttc cat ggg gct tct tcc cga acc att gcg aca cct gtg     3416
Phe Thr Thr Phe His Gly Ala Ser Ser Arg Thr Ile Ala Thr Pro Val
                950                 955                 960 ggg gcc ctt aac cca agg tgg tgg tcg gcc agt gat gac gtc acg gtc     3464
Gly Ala Leu Asn Pro Arg Trp Trp Ser Ala Ser Asp Asp Val Thr Val
        965                 970                 975
```

```
tat ccc ctc ccc gat gga gct aac tcg ttg gtt ccc tgc tcg tgt cag      3512
Tyr Pro Leu Pro Asp Gly Ala Asn Ser Leu Val Pro Cys Ser Cys Gln
        980                 985                 990 gct gag tcc tgt tgg gtc aty cga tcc gat ggg gct ctt tgc cat ggc      3560
Ala Glu Ser Cys Trp Val Xaa Arg Ser Asp Gly Ala Leu Cys His Gly
        995                 1000                1005 ttg agc aag ggg gac aag gta gaa ctg gac gtg gcc atg gag gtt          3605
Leu Ser Lys Gly Asp Lys Val Glu Leu Asp Val Ala Met Glu Val
1010                1015                1020 gct gac ttt cgt ggg tcg tct ggg tct cct gtc cta tgc gac gag          3650
Ala Asp Phe Arg Gly Ser Ser Gly Ser Pro Val Leu Cys Asp Glu
1025                1030                1035 ggg cac gct gta gga atg ctc gtg tcc gtc ctt cat tcg ggg ggg          3695
Gly His Ala Val Gly Met Leu Val Ser Val Leu His Ser Gly Gly
1040                1045                1050 agg gtg acc gcg gct cga ttc act cgg ccg tgg acc caa gtc cca          3740
Arg Val Thr Ala Ala Arg Phe Thr Arg Pro Trp Thr Gln Val Pro
1055                1060                1065 aca gac gcc aag act acc act gag cca ccc ccg gtg cca gct aaa          3785
Thr Asp Ala Lys Thr Thr Thr Glu Pro Pro Pro Val Pro Ala Lys
1070                1075                1080 ggg gtt ttc aaa gag gct cct ctt ttc atg cca aca ggg gcg ggg          3830
Gly Val Phe Lys Glu Ala Pro Leu Phe Met Pro Thr Gly Ala Gly
1085                1090                1095 aaa agc aca cgc gtc cct ttg gag tat gga aac atg ggg cac aag          3875
Lys Ser Thr Arg Val Pro Leu Glu Tyr Gly Asn Met Gly His Lys
1100                1105                1110 gtc ctg att ctc aac ccg tcg gtt gcc act gtg agg gcc atg ggc          3920
Val Leu Ile Leu Asn Pro Ser Val Ala Thr Val Arg Ala Met Gly
1115                1120                1125 cct tac atg gag agg ctg gcg ggg aaa cat cct agc att ttc tgt          3965
Pro Tyr Met Glu Arg Leu Ala Gly Lys His Pro Ser Ile Phe Cys
1130                1135                1140 gga cac gac aca aca gct ttc aca cgg atc acg gac tct cca ttg          4010
Gly His Asp Thr Thr Ala Phe Thr Arg Ile Thr Asp Ser Pro Leu
1145                1150                1155 acg tac tct acc tat ggg agg ttt ctg gcc aac ccg agg cag atg          4055
Thr Tyr Ser Thr Tyr Gly Arg Phe Leu Ala Asn Pro Arg Gln Met
1160                1165                1170 ctg agg gga gtt tcc gtg gtc atc tgt gat gag tgc cac agt cat          4100
Leu Arg Gly Val Ser Val Val Ile Cys Asp Glu Cys His Ser His
1175                1180                1185 gac tca act gtg ttg ctg ggt ata ggc agg gtc agg gac gtg gcg          4145
Asp Ser Thr Val Leu Leu Gly Ile Gly Arg Val Arg Asp Val Ala
1190                1195                1200 cgg ggg tgt gga gtg caa tta gtg ctc tac gct act gcg act ccc          4190
Arg Gly Cys Gly Val Gln Leu Val Leu Tyr Ala Thr Ala Thr Pro
1205                1210                1215 ccg ggc tcg cct atg act cag cat cca tcc ata att gag aca aag          4235
Pro Gly Ser Pro Met Thr Gln His Pro Ser Ile Ile Glu Thr Lys
1220                1225                1230 ctg gac gtt ggt gag atc ccc ttt tat ggg cat ggt atc ccc ctc          4280
Leu Asp Val Gly Glu Ile Pro Phe Tyr Gly His Gly Ile Pro Leu
1235                1240                1245 gag cgt atg agg act ggt cgc cac ctt gta ttc tgc cat tcc aag          4325
Glu Arg Met Arg Thr Gly Arg His Leu Val Phe Cys His Ser Lys
1250                1255                1260 gcg gag tgc gag aga ttg gcc ggc cag ttc tcc gcg cgg ggg gtt          4370
Ala Glu Cys Glu Arg Leu Ala Gly Gln Phe Ser Ala Arg Gly Val
1265                1270                1275
```

| | | |
|---|---|---|
| aat gcc atc gcc tat tat agg ggt aag gac agt tcc atc atc aaa<br>Asn Ala Ile Ala Tyr Tyr Arg Gly Lys Asp Ser Ser Ile Ile Lys<br>1280                         1285                      1290 | 4415 |
| gac gga gac ctg gtg gtt tgt gcg aca gac gcg ctc tct acc ggg<br>Asp Gly Asp Leu Val Val Cys Ala Thr Asp Ala Leu Ser Thr Gly<br>1295                         1300                      1305 | 4460 |
| tac aca gga aac ttc gat tct gtc acc gac tgt ggg ttg gtg gtg<br>Tyr Thr Gly Asn Phe Asp Ser Val Thr Asp Cys Gly Leu Val Val<br>1310                         1315                      1320 | 4505 |
| gag gag gtc gtt gag gtg acc ctt gat ccc acc att acc att tcc<br>Glu Glu Val Val Glu Val Thr Leu Asp Pro Thr Ile Thr Ile Ser<br>1325                         1330                      1335 | 4550 |
| ttg cgg act gtc cct gct tcg gct gaa ttg tcg atg cag cgg cgc<br>Leu Arg Thr Val Pro Ala Ser Ala Glu Leu Ser Met Gln Arg Arg<br>1340                         1345                      1350 | 4595 |
| gga cgc acg ggg aga ggt cgg tcg ggc cgc tac tac tac gct ggg<br>Gly Arg Thr Gly Arg Gly Arg Ser Gly Arg Tyr Tyr Tyr Ala Gly<br>1355                         1360                      1365 | 4640 |
| gtc ggt aag gct ccc gcg ggg gtg gtg cgg tct ggt ccg gtc tgg<br>Val Gly Lys Ala Pro Ala Gly Val Val Arg Ser Gly Pro Val Trp<br>1370                         1375                      1380 | 4685 |
| tcg gca gtg gaa gct gga gtg acc tgg tat gga atg gaa cct gac<br>Ser Ala Val Glu Ala Gly Val Thr Trp Tyr Gly Met Glu Pro Asp<br>1385                         1390                      1395 | 4730 |
| ttg aca gca aac ctt ctg aga ctt tac gac gac tgc cct tac acc<br>Leu Thr Ala Asn Leu Leu Arg Leu Tyr Asp Asp Cys Pro Tyr Thr<br>1400                         1405                      1410 | 4775 |
| gca gcc gtc gca gct gac att ggt gaa gcc gcg gtg ttc ttt gcg<br>Ala Ala Val Ala Ala Asp Ile Gly Glu Ala Ala Val Phe Phe Ala<br>1415                         1420                      1425 | 4820 |
| ggc ctc gcg ccc ctc agg atg cat ccc gat gtt agc tgg gca aaa<br>Gly Leu Ala Pro Leu Arg Met His Pro Asp Val Ser Trp Ala Lys<br>1430                         1435                      1440 | 4865 |
| gtt cgc ggc gtc aat tgg ccc ctc ctg gtg ggt gtt cag cgg acg<br>Val Arg Gly Val Asn Trp Pro Leu Leu Val Gly Val Gln Arg Thr<br>1445                         1450                      1455 | 4910 |
| atg tgt cgg gaa aca ctg tct ccc ggc ccg tcg gac gac cct cag<br>Met Cys Arg Glu Thr Leu Ser Pro Gly Pro Ser Asp Asp Pro Gln<br>1460                         1465                      1470 | 4955 |
| tgg gca ggt ctg aaa ggc ccg aat cct gtc cca cta ctg ctg agg<br>Trp Ala Gly Leu Lys Gly Pro Asn Pro Val Pro Leu Leu Leu Arg<br>1475                         1480                      1485 | 5000 |
| tgg ggc aat gat ttg cca tca aaa gtg gcc ggc cac cac ata gtt<br>Trp Gly Asn Asp Leu Pro Ser Lys Val Ala Gly His His Ile Val<br>1490                         1495                      1500 | 5045 |
| gac gat ctg gtc cgt cgg ctc ggt gtg gcg gag gga tac gtg cgc<br>Asp Asp Leu Val Arg Arg Leu Gly Val Ala Glu Gly Tyr Val Arg<br>1505                         1510                      1515 | 5090 |
| tgt gat gct ggr ccc atc ctc atg gtg ggc ttg gcc ata gcg ggc<br>Cys Asp Ala Xaa Pro Ile Leu Met Val Gly Leu Ala Ile Ala Gly<br>1520                         1525                      1530 | 5135 |
| ggc atg atc tac gcc tct tac act ggg tcg cta gtg gtg gta aca<br>Gly Met Ile Tyr Ala Ser Tyr Thr Gly Ser Leu Val Val Val Thr<br>1535                         1540                      1545 | 5180 |
| gac tgg gat gtg aag gga ggt ggc aat ccc ctt tat agg agt ggt<br>Asp Trp Asp Val Lys Gly Gly Gly Asn Pro Leu Tyr Arg Ser Gly<br>1550                         1555                      1560 | 5225 |
| gac cag gcc acc cct caa ccc gtg gtg cag gtc ccc ccg gta gac<br>Asp Gln Ala Thr Pro Gln Pro Val Val Gln Val Pro Pro Val Asp<br>1565                         1570                      1575 | 5270 |

```
cat  cgg  ccg  ggg  ggg  gag  tct  gcg  cca  cgg  gat  gcc  aag  aca  gtg          5315
His  Arg  Pro  Gly  Gly  Glu  Ser  Ala  Pro  Arg  Asp  Ala  Lys  Thr  Val
1580                     1585                     1590 aca  gat  gcg  gtg  gca  gcc  atc  cag  gtg  aac  tgc  gat  tgg  tct  gtg          5360
Thr  Asp  Ala  Val  Ala  Ala  Ile  Gln  Val  Asn  Cys  Asp  Trp  Ser  Val
1595                     1600                     1605 atg  acc  ctg  tcg  atc  ggg  gaa  gtc  ctc  acc  ttg  gct  cag  gct  aag          5405
Met  Thr  Leu  Ser  Ile  Gly  Glu  Val  Leu  Thr  Leu  Ala  Gln  Ala  Lys
1610                     1615                     1620 aca  gcc  gag  gcc  tac  gca  gct  act  tcc  agg  tgg  ctc  gct  ggc  tgc          5450
Thr  Ala  Glu  Ala  Tyr  Ala  Ala  Thr  Ser  Arg  Trp  Leu  Ala  Gly  Cys
1625                     1630                     1635 tac  acg  ggg  acg  cgg  gcc  gtc  ccc  act  gta  tca  att  gtt  gac  aag          5495
Tyr  Thr  Gly  Thr  Arg  Ala  Val  Pro  Thr  Val  Ser  Ile  Val  Asp  Lys
1640                     1645                     1650 ctc  ttc  gcc  ggg  ggt  tgg  gcc  gcc  gtg  gtg  ggt  cac  tgt  cac  agc          5540
Leu  Phe  Ala  Gly  Gly  Trp  Ala  Ala  Val  Val  Gly  His  Cys  His  Ser
1655                     1660                     1665 gtc  att  gct  gcg  gcg  gtg  gct  gcc  tat  gga  gct  tct  cga  agt  cct          5585
Val  Ile  Ala  Ala  Ala  Val  Ala  Ala  Tyr  Gly  Ala  Ser  Arg  Ser  Pro
1670                     1675                     1680 cca  ctg  gcc  gcg  gcg  gcg  tcc  tac  ctc  atg  ggg  ttg  ggc  gtc  gga          5630
Pro  Leu  Ala  Ala  Ala  Ala  Ser  Tyr  Leu  Met  Gly  Leu  Gly  Val  Gly
1685                     1690                     1695 ggc  aac  gca  cag  gcg  cgc  ttg  gct  tca  gct  ctt  cta  ctg  ggg  gct          5675
Gly  Asn  Ala  Gln  Ala  Arg  Leu  Ala  Ser  Ala  Leu  Leu  Leu  Gly  Ala
1700                     1705                     1710 gct  ggt  acg  gct  ctg  ggg  acc  cct  gtc  gtg  gga  ctc  acc  atg  gcg          5720
Ala  Gly  Thr  Ala  Leu  Gly  Thr  Pro  Val  Val  Gly  Leu  Thr  Met  Ala
1715                     1720                     1725 ggg  gcc  ttc  atg  ggc  ggt  gcc  agc  gtg  tcc  ccc  tcc  ctc  gtc  act          5765
Gly  Ala  Phe  Met  Gly  Gly  Ala  Ser  Val  Ser  Pro  Ser  Leu  Val  Thr
1730                     1735                     1740 gtc  cta  ctt  ggg  gct  gtg  gga  ggt  tgg  gag  ggc  gtt  gtc  aac  gct          5810
Val  Leu  Leu  Gly  Ala  Val  Gly  Gly  Trp  Glu  Gly  Val  Val  Asn  Ala
1745                     1750                     1755 gcc  agt  ctc  gtc  ttc  gac  ttc  atg  gct  ggg  aaa  ctt  tca  aca  gaa          5855
Ala  Ser  Leu  Val  Phe  Asp  Phe  Met  Ala  Gly  Lys  Leu  Ser  Thr  Glu
1760                     1765                     1770 gac  ctt  tgg  tat  gcc  atc  ccg  gta  ctc  act  agt  cct  ggr  gcg  ggc          5900
Asp  Leu  Trp  Tyr  Ala  Ile  Pro  Val  Leu  Thr  Ser  Pro  Xaa  Ala  Gly
1775                     1780                     1785 ctc  gcg  ggg  att  gcc  ctt  ggt  ctg  gtt  ttg  tac  tca  gca  aac  aac          5945
Leu  Ala  Gly  Ile  Ala  Leu  Gly  Leu  Val  Leu  Tyr  Ser  Ala  Asn  Asn
1790                     1795                     1800 tct  ggc  act  acc  aca  tgg  ctg  aac  cgt  ctg  ctg  acg  acg  ttg  cca          5990
Ser  Gly  Thr  Thr  Thr  Trp  Leu  Asn  Arg  Leu  Leu  Thr  Thr  Leu  Pro
1805                     1810                     1815 cgg  tca  tct  tgc  ata  ccc  gac  agc  tac  ttc  caa  cag  gct  gac  tac          6035
Arg  Ser  Ser  Cys  Ile  Pro  Asp  Ser  Tyr  Phe  Gln  Gln  Ala  Asp  Tyr
1820                     1825                     1830 tgc  gac  aag  gtc  tcg  gca  atc  gtg  cgc  cgc  ctg  agc  ctt  act  cgc          6080
Cys  Asp  Lys  Val  Ser  Ala  Ile  Val  Arg  Arg  Leu  Ser  Leu  Thr  Arg
1835                     1840                     1845 acc  gtg  gtg  gcc  ctg  gtc  aac  agg  gag  cct  aag  gtg  gat  gag  gtc          6125
Thr  Val  Val  Ala  Leu  Val  Asn  Arg  Glu  Pro  Lys  Val  Asp  Glu  Val
1850                     1855                     1860 cag  gtg  ggg  tac  gtc  tgg  gat  ctg  tgg  gag  tgg  gtg  atg  cgc  cag          6170
Gln  Val  Gly  Tyr  Val  Trp  Asp  Leu  Trp  Glu  Trp  Val  Met  Arg  Gln
1865                     1870                     1875
```

```
gtg  cgc  atg  gtg  atg  tct  aga  ctc  cgg  gcc  ctc  tgc  cct  gtg  gtg         6215
Val  Arg  Met  Val  Met  Ser  Arg  Leu  Arg  Ala  Leu  Cys  Pro  Val  Val
1880                 1885                     1890 tca  ctc  ccc  ttg  tgg  cac  tgc  ggg  gag  ggg  tgg  tcc  ggt  gaa  tgg         6260
Ser  Leu  Pro  Leu  Trp  His  Cys  Gly  Glu  Gly  Trp  Ser  Gly  Glu  Trp
1895                 1900                     1905 ctt  ctc  gat  ggg  cac  gtg  gag  agt  cgt  tgt  ctg  tgc  ggg  tgt  gta         6305
Leu  Leu  Asp  Gly  His  Val  Glu  Ser  Arg  Cys  Leu  Cys  Gly  Cys  Val
1910                 1915                     1920 atc  acc  ggc  gac  gtc  ctc  aat  ggg  caa  ctc  aaa  gat  cca  gtt  tac         6350
Ile  Thr  Gly  Asp  Val  Leu  Asn  Gly  Gln  Leu  Lys  Asp  Pro  Val  Tyr
1925                 1930                     1935 tct  acc  aag  ctg  tgc  agg  cac  tac  tgg  atg  gga  act  gtg  ccg  gtc         6395
Ser  Thr  Lys  Leu  Cys  Arg  His  Tyr  Trp  Met  Gly  Thr  Val  Pro  Val
1940                 1945                     1950 aac  atg  ctg  ggc  tac  ggg  gaa  acc  tca  cct  ctt  ctc  gcc  tct  gac         6440
Asn  Met  Leu  Gly  Tyr  Gly  Glu  Thr  Ser  Pro  Leu  Leu  Ala  Ser  Asp
1955                 1960                     1965 acc  ccg  aag  gtg  gta  ccc  ttc  ggg  acg  tcg  ggg  tgg  gct  gag  gtg         6485
Thr  Pro  Lys  Val  Val  Pro  Phe  Gly  Thr  Ser  Gly  Trp  Ala  Glu  Val
1970                 1975                     1980 gtg  gtg  acc  cct  acc  cac  gtg  gtg  atc  agg  cgc  acg  tcc  tgt  tac         6530
Val  Val  Thr  Pro  Thr  His  Val  Val  Ile  Arg  Arg  Thr  Ser  Cys  Tyr
1985                 1990                     1995 aaa  ctg  ctt  cgc  cag  caa  att  ctt  tca  gca  gct  gta  gct  gag  ccc         6575
Lys  Leu  Leu  Arg  Gln  Gln  Ile  Leu  Ser  Ala  Ala  Val  Ala  Glu  Pro
2000                 2005                     2010 tac  tac  gtt  gat  ggc  att  ccg  gtc  tct  tgg  gag  gct  gac  gcg  aga         6620
Tyr  Tyr  Val  Asp  Gly  Ile  Pro  Val  Ser  Trp  Glu  Ala  Asp  Ala  Arg
2015                 2020                     2025 gcg  ccg  gcc  atg  gtc  tac  ggt  ccg  ggc  caa  agt  gtt  acc  att  gat         6665
Ala  Pro  Ala  Met  Val  Tyr  Gly  Pro  Gly  Gln  Ser  Val  Thr  Ile  Asp
2030                 2035                     2040 ggg  gag  cgc  tac  acc  ctt  ccg  cac  cag  ttg  cgg  atg  cgg  aat  gtg         6710
Gly  Glu  Arg  Tyr  Thr  Leu  Pro  His  Gln  Leu  Arg  Met  Arg  Asn  Val
2045                 2050                     2055 gcg  ccc  tct  gag  gtt  tca  tct  gag  gtc  agc  atc  gag  atc  ggg  acg         6755
Ala  Pro  Ser  Glu  Val  Ser  Ser  Glu  Val  Ser  Ile  Glu  Ile  Gly  Thr
2060                 2065                     2070 gag  act  gaa  gac  tca  gaa  ctg  act  gag  gcc  gat  ttg  cca  cca  gcg         6800
Glu  Thr  Glu  Asp  Ser  Glu  Leu  Thr  Glu  Ala  Asp  Leu  Pro  Pro  Ala
2075                 2080                     2085 gct  gct  gcc  ctc  caa  gcg  ata  gag  aat  gct  gcg  aga  att  ctc  gaa         6845
Ala  Ala  Ala  Leu  Gln  Ala  Ile  Glu  Asn  Ala  Ala  Arg  Ile  Leu  Glu
2090                 2095                     2100 ccg  cac  atc  gat  gtc  ayc  atg  gag  gat  tgc  agt  aca  ccc  tct  ctc         6890
Pro  His  Ile  Asp  Val  Xaa  Met  Glu  Asp  Cys  Ser  Thr  Pro  Ser  Leu
2105                 2110                     2115 tgt  ggt  agt  agc  cga  gag  atg  cct  gtg  tgg  gga  gaa  gac  ata  ccc         6935
Cys  Gly  Ser  Ser  Arg  Glu  Met  Pro  Val  Trp  Gly  Glu  Asp  Ile  Pro
2120                 2125                     2130 cgc  act  cca  tcg  cct  gca  ctt  atc  tcg  gtt  acg  gag  agc  agc  tca         6980
Arg  Thr  Pro  Ser  Pro  Ala  Leu  Ile  Ser  Val  Thr  Glu  Ser  Ser  Ser
2135                 2140                     2145 gat  gag  aag  acc  ctg  tcg  gtg  acc  tcc  tcg  cag  gag  gac  acc  ccg         7025
Asp  Glu  Lys  Thr  Leu  Ser  Val  Thr  Ser  Ser  Gln  Glu  Asp  Thr  Pro
2150                 2155                     2160 tcc  tca  gac  tca  ttt  gaa  gtc  atc  caa  gag  tct  gat  act  gct  gaa         7070
Ser  Ser  Asp  Ser  Phe  Glu  Val  Ile  Gln  Glu  Ser  Asp  Thr  Ala  Glu
2165                 2170                     2175
```

| | | | | | | | | | | | | | | |
|---|---|---|---|---|---|---|---|---|---|---|---|---|---|---|
| tca | gag | gaa | agc | gtc | ttc | aac | gtg | gct | ctt | tcc | gta | cta | aaa | gcc | 7115 |
| Ser | Glu | Glu | Ser | Val | Phe | Asn | Val | Ala | Leu | Ser | Val | Leu | Lys | Ala | |
| 2180 | | | | 2185 | | | | | 2190 | | | | | | |

| tta | ttt | cca | cag | agc | gat | gcc | aca | cga | aag | cta | acg | gtt | aag | atg | 7160 |
| Leu | Phe | Pro | Gln | Ser | Asp | Ala | Thr | Arg | Lys | Leu | Thr | Val | Lys | Met | |
| 2195 | | | | 2200 | | | | | 2205 | | | | | | |

| tct | tgc | tgt | gtt | gag | aag | agc | gta | aca | cgc | ttc | ttt | tct | tta | ggg | 7205 |
| Ser | Cys | Cys | Val | Glu | Lys | Ser | Val | Thr | Arg | Phe | Phe | Ser | Leu | Gly | |
| 2210 | | | | 2215 | | | | | 2220 | | | | | | |

| ttg | acc | gtg | gct | gac | gtg | gct | agc | ctg | tgt | gag | atg | gag | atc | cag | 7250 |
| Leu | Thr | Val | Ala | Asp | Val | Ala | Ser | Leu | Cys | Glu | Met | Glu | Ile | Gln | |
| 2225 | | | | 2230 | | | | | 2235 | | | | | | |

| aac | cat | aca | gcc | tat | tgt | gac | aag | gtg | cgc | act | ccg | ctc | gaa | ttg | 7295 |
| Asn | His | Thr | Ala | Tyr | Cys | Asp | Lys | Val | Arg | Thr | Pro | Leu | Glu | Leu | |
| 2240 | | | | 2245 | | | | | 2250 | | | | | | |

| caa | gtt | ggg | tgc | ttg | gtg | ggc | aat | gaa | ctt | acc | ttt | gaa | tgt | gac | 7340 |
| Gln | Val | Gly | Cys | Leu | Val | Gly | Asn | Glu | Leu | Thr | Phe | Glu | Cys | Asp | |
| 2255 | | | | 2260 | | | | | 2265 | | | | | | |

| aag | tgt | gag | gca | cgc | caa | gag | acc | ctt | gcc | tcc | ttc | tcc | tac | ata | 7385 |
| Lys | Cys | Glu | Ala | Arg | Gln | Glu | Thr | Leu | Ala | Ser | Phe | Ser | Tyr | Ile | |
| 2270 | | | | 2275 | | | | | 2280 | | | | | | |

| tgg | tcc | ggg | gtc | cca | ctt | act | cgg | gcc | act | ccg | gcc | aaa | cca | cca | 7430 |
| Trp | Ser | Gly | Val | Pro | Leu | Thr | Arg | Ala | Thr | Pro | Ala | Lys | Pro | Pro | |
| 2285 | | | | 2290 | | | | | 2295 | | | | | | |

| gtg | gtg | agg | ccg | gtg | ggg | tcc | ttg | ttg | gtg | gca | gac | acc | acc | aag | 7475 |
| Val | Val | Arg | Pro | Val | Gly | Ser | Leu | Leu | Val | Ala | Asp | Thr | Thr | Lys | |
| 2300 | | | | 2305 | | | | | 2310 | | | | | | |

| gtc | tac | gtg | acc | aat | ccg | gac | aat | gtt | ggg | agg | agg | gtt | gac | aag | 7520 |
| Val | Tyr | Val | Thr | Asn | Pro | Asp | Asn | Val | Gly | Arg | Arg | Val | Asp | Lys | |
| 2315 | | | | 2320 | | | | | 2325 | | | | | | |

| gtg | act | ttc | tgg | cgc | gct | cct | cgg | gta | cac | gac | aag | ttc | ctc | gtg | 7565 |
| Val | Thr | Phe | Trp | Arg | Ala | Pro | Arg | Val | His | Asp | Lys | Phe | Leu | Val | |
| 2330 | | | | 2335 | | | | | 2340 | | | | | | |

| gac | tcg | atc | gag | cgc | gct | cgg | aga | gct | gct | caa | ggc | tgc | cta | agc | 7610 |
| Asp | Ser | Ile | Glu | Arg | Ala | Arg | Arg | Ala | Ala | Gln | Gly | Cys | Leu | Ser | |
| 2345 | | | | 2350 | | | | | 2355 | | | | | | |

| atg | ggt | tac | act | tat | gag | gag | gca | ata | agg | act | gtt | agg | ccg | cat | 7655 |
| Met | Gly | Tyr | Thr | Tyr | Glu | Glu | Ala | Ile | Arg | Thr | Val | Arg | Pro | His | |
| 2360 | | | | 2365 | | | | | 2370 | | | | | | |

| gct | gcc | atg | ggc | tgg | gga | tct | aag | gtg | tcg | gtc | aag | gac | ttg | gcc | 7700 |
| Ala | Ala | Met | Gly | Trp | Gly | Ser | Lys | Val | Ser | Val | Lys | Asp | Leu | Ala | |
| 2375 | | | | 2380 | | | | | 2385 | | | | | | |

| acc | cct | gcg | ggg | aag | atg | gct | gtt | cat | gac | cgg | ctt | cag | gag | ata | 7745 |
| Thr | Pro | Ala | Gly | Lys | Met | Ala | Val | His | Asp | Arg | Leu | Gln | Glu | Ile | |
| 2390 | | | | 2395 | | | | | 2400 | | | | | | |

| ctt | gaa | ggg | act | ccg | gtc | cct | ttt | acc | ctg | act | gtc | aaa | aag | gag | 7790 |
| Leu | Glu | Gly | Thr | Pro | Val | Pro | Phe | Thr | Leu | Thr | Val | Lys | Lys | Glu | |
| 2405 | | | | 2410 | | | | | 2415 | | | | | | |

| gtg | ttc | ttc | aaa | gat | cgt | aag | gag | gag | aag | gcc | ccc | cgc | ctc | att | 7835 |
| Val | Phe | Phe | Lys | Asp | Arg | Lys | Glu | Glu | Lys | Ala | Pro | Arg | Leu | Ile | |
| 2420 | | | | 2425 | | | | | 2430 | | | | | | |

| gtg | ttc | ccc | ccc | ctg | gac | ttc | cgg | ata | gct | gaa | aag | ctc | att | ctg | 7880 |
| Val | Phe | Pro | Pro | Leu | Asp | Phe | Arg | Ile | Ala | Glu | Lys | Leu | Ile | Leu | |
| 2435 | | | | 2440 | | | | | 2445 | | | | | | |

| gga | gac | ccg | ggg | cgg | gtt | gca | aag | gcc | ggt | gtt | ggg | ggg | gct | tac | 7925 |
| Gly | Asp | Pro | Gly | Arg | Val | Ala | Lys | Ala | Gly | Val | Gly | Gly | Ala | Tyr | |
| 2450 | | | | 2455 | | | | | 2460 | | | | | | |

| gcc | ttc | cag | tac | acc | ccc | aac | cag | cgg | gtt | aag | gag | atg | cta | aag | 7970 |
| Ala | Phe | Gln | Tyr | Thr | Pro | Asn | Gln | Arg | Val | Lys | Glu | Met | Leu | Lys | |
| 2465 | | | | 2470 | | | | | 2475 | | | | | | |

```
ctg tgg gaa tca aag aag acc ccg tgc gcc atc tgt gtg gat gcc        8015
Leu Trp Glu Ser Lys Lys Thr Pro Cys Ala Ile Cys Val Asp Ala
2480            2485                2490 act tgc ttc gac agt agc att act gar gag gac gtg gca cta gag        8060
Thr Cys Phe Asp Ser Ser Ile Thr Glu Glu Asp Val Ala Leu Glu
2495            2500                2505 aca gag ctt tac gcc ctg gcc tcg gac cat cca gaa tgg gtg cgc        8105
Thr Glu Leu Tyr Ala Leu Ala Ser Asp His Pro Glu Trp Val Arg
2510            2515                2520 gcc ctg ggg aaa tac trt gcc tct ggc aca atg gtg acc ccg gaa        8150
Ala Leu Gly Lys Tyr Xaa Ala Ser Gly Thr Met Val Thr Pro Glu
2525            2530                2535 ggg gtg cca gtg ggc gag agg tat tgt agg tcc tcg ggt gtg ttg        8195
Gly Val Pro Val Gly Glu Arg Tyr Cys Arg Ser Ser Gly Val Leu
2540            2545                2550 acc aca agt gct agc aac tgt ttg acc tgc tac atc aaa gtg aga        8240
Thr Thr Ser Ala Ser Asn Cys Leu Thr Cys Tyr Ile Lys Val Arg
2555            2560                2565 gcc gcc tgt gag agg atc gga ctg aaa aat gtc tcg ctt ctc atc        8285
Ala Ala Cys Glu Arg Ile Gly Leu Lys Asn Val Ser Leu Leu Ile
2570            2575                2580 gcg ggc gat gac tgc tta att gtg tgc gag agg cct gta tgc gac        8330
Ala Gly Asp Asp Cys Leu Ile Val Cys Glu Arg Pro Val Cys Asp
2585            2590                2595 cct tgc gag gcc ctg ggc cga acc ctg gct tcg tac ggg tac gcg        8375
Pro Cys Glu Ala Leu Gly Arg Thr Leu Ala Ser Tyr Gly Tyr Ala
2600            2605                2610 tgt gag ccc tcg tat cac gct tca ctg gac aca gcc ccc ttc tgc        8420
Cys Glu Pro Ser Tyr His Ala Ser Leu Asp Thr Ala Pro Phe Cys
2615            2620                2625 tcc act tgg ctc gct gag tgc aat gcg gat ggg raa agg cat ttc        8465
Ser Thr Trp Leu Ala Glu Cys Asn Ala Asp Gly Xaa Arg His Phe
2630            2635                2640 ttc ctg acc acg gac ttt cgg aga cca ctc gct cgc atg tcg agc        8510
Phe Leu Thr Thr Asp Phe Arg Arg Pro Leu Ala Arg Met Ser Ser
2645            2650                2655 gag tac agt gac cct atg gct tcg gcc att ggt tac att ctc ctc        8555
Glu Tyr Ser Asp Pro Met Ala Ser Ala Ile Gly Tyr Ile Leu Leu
2660            2665                2670 tac ccc tgg crt ccc atc aca cgg tgg gtc atc atc ccg cat gtg        8600
Tyr Pro Trp Xaa Pro Ile Thr Arg Trp Val Ile Ile Pro His Val
2675            2680                2685 cta aca tgc gct tct tcc cgg ggt ggt ggc aca csg tct gat ccg        8645
Leu Thr Cys Ala Ser Ser Arg Gly Gly Gly Thr Xaa Ser Asp Pro
2690            2695                2700 gtt tgg tgt cag gtt cat ggt aac tac tac aag ttt ccc ctg gac        8690
Val Trp Cys Gln Val His Gly Asn Tyr Tyr Lys Phe Pro Leu Asp
2705            2710                2715 aaa ctg cct aac atc atc gtg gcc ctc cac gga cca gca gcg ttg        8735
Lys Leu Pro Asn Ile Ile Val Ala Leu His Gly Pro Ala Ala Leu
2720            2725                2730 agg gtt acc gca gac aca acc aaa aca aag atg gag gct ggg aag        8780
Arg Val Thr Ala Asp Thr Thr Lys Thr Lys Met Glu Ala Gly Lys
2735            2740                2745 gtt ctg agc gac ctc aag ctc cct ggt cta gcc gtc cac cgc aag        8825
Val Leu Ser Asp Leu Lys Leu Pro Gly Leu Ala Val His Arg Lys
2750            2755                2760 aag gcc ggg gca ttg cga aca cgc atg ctc cgg tcg cgc ggt tgg        8870
Lys Ala Gly Ala Leu Arg Thr Arg Met Leu Arg Ser Arg Gly Trp
2765            2770                2775
```

-continued

| | | | | | | | | | | | | | | |
|---|---|---|---|---|---|---|---|---|---|---|---|---|---|---|
| gcg | gag | ttg | gct | agg | ggc | ctg | ttg | tgg | cat | cca | gga | ctc | cgg | ctt | 8915 |
| Ala | Glu | Leu | Ala | Arg | Gly | Leu | Leu | Trp | His | Pro | Gly | Leu | Arg | Leu | |
| 2780 | | | | | 2785 | | | | | 2790 | | | | | |

| | | | | | | | | | | | | | | |
|---|---|---|---|---|---|---|---|---|---|---|---|---|---|---|
| cct | ccc | cct | gag | att | gct | ggt | atc | cca | ggg | ggt | ttc | cct | ctg | tcc | 8960 |
| Pro | Pro | Pro | Glu | Ile | Ala | Gly | Ile | Pro | Gly | Gly | Phe | Pro | Leu | Ser | |
| 2795 | | | | | 2800 | | | | | 2805 | | | | | |

| | | | | | | | | | | | | | | |
|---|---|---|---|---|---|---|---|---|---|---|---|---|---|---|
| ccc | ccc | tac | atg | ggg | gtg | gtt | cat | caa | ttg | gat | ttc | aca | gcs | cag | 9005 |
| Pro | Pro | Tyr | Met | Gly | Val | Val | His | Gln | Leu | Asp | Phe | Thr | Ala | Gln | |
| 2810 | | | | | 2815 | | | | | 2820 | | | | | |

| | | | | | | | | | | | | | | |
|---|---|---|---|---|---|---|---|---|---|---|---|---|---|---|
| cgg | agt | cgc | tgg | cgg | tgg | ttg | ggg | ttc | tta | gcc | ctg | ctc | atc | gta | 9050 |
| Arg | Ser | Arg | Trp | Arg | Trp | Leu | Gly | Phe | Leu | Ala | Leu | Leu | Ile | Val | |
| 2825 | | | | | 2830 | | | | | 2835 | | | | | |

| | | | | | | | | |
|---|---|---|---|---|---|---|---|---|
| gcg | ctc | ttt | ggg | tga | actaaattca | tctgttgcgg | caaggttgag | cggctgatca | 9105 |
| Ala | Leu | Phe | Gly | | | | | | |
| 2840 | | | | | | | | | | ccgctcaagg aggttcccgc cctccccgcc ccagggtct ccccgctggg taaaaagggc 9165 ccggccttgg gaggcatggt ggttactaac cccctggcag ggttaacgcc tgatggtgct 9225 aatgcactgc cgcttcggcg gcgggtcgct accttatagc gtaatccgtg actacgggct 9285 gctcgcagag ccctcccgg atggggcaca gtgcactgtg atctgaaggg gtgcaccccg 9345 gtaagagctc ggcccaaagg ccgggttcta ct 9377

<210> SEQ ID NO 2
<211> LENGTH: 2843
<212> TYPE: PRT
<213> ORGANISM: Hepatitis GB virus C
<220> FEATURE:
<221> NAME/KEY: misc_feature
<222> LOCATION: (30)..(30)
<223> OTHER INFORMATION: The 'Xaa' at location 30 stands for Leu, or
      Phe.
<220> FEATURE:
<221> NAME/KEY: misc_feature
<222> LOCATION: (582)..(582)
<223> OTHER INFORMATION: The 'Xaa' at location 582 stands for Gly, or
      Val.
<220> FEATURE:
<221> NAME/KEY: misc_feature
<222> LOCATION: (584)..(584)
<223> OTHER INFORMATION: The 'Xaa' at location 584 stands for Ala, or
      Pro.
<220> FEATURE:
<221> NAME/KEY: misc_feature
<222> LOCATION: (587)..(587)
<223> OTHER INFORMATION: The 'Xaa' at location 587 stands for Arg, or
      His.
<220> FEATURE:
<221> NAME/KEY: misc_feature
<222> LOCATION: (839)..(839)
<223> OTHER INFORMATION: The 'Xaa' at location 839 stands for Thr, or
      Pro.
<220> FEATURE:
<221> NAME/KEY: misc_feature
<222> LOCATION: (892)..(892)
<223> OTHER INFORMATION: The 'Xaa' at location 892 stands for Ala, or
      Val.
<220> FEATURE:
<221> NAME/KEY: misc_feature
<222> LOCATION: (1000)..(1000)
<223> OTHER INFORMATION: The 'Xaa' at location 1000 stands for Ile.
<220> FEATURE:
<221> NAME/KEY: misc_feature
<222> LOCATION: (1523)..(1523)
<223> OTHER INFORMATION: The 'Xaa' at location 1523 stands for Gly.
<220> FEATURE:
<221> NAME/KEY: misc_feature
<222> LOCATION: (1787)..(1787)
<223> OTHER INFORMATION: The 'Xaa' at location 1787 stands for Gly.

```
<220> FEATURE:
<221> NAME/KEY: misc_feature
<222> LOCATION: (2110)..(2110)
<223> OTHER INFORMATION: The 'Xaa' at location 2110 stands for Thr, or
      Ile.
<220> FEATURE:
<221> NAME/KEY: misc_feature
<222> LOCATION: (2530)..(2530)
<223> OTHER INFORMATION: The 'Xaa' at location 2530 stands for Cys, or
      Tyr.
<220> FEATURE:
<221> NAME/KEY: misc_feature
<222> LOCATION: (2641)..(2641)
<223> OTHER INFORMATION: The 'Xaa' at location 2641 stands for Glu, or
      Lys.
<220> FEATURE:
<221> NAME/KEY: misc_feature
<222> LOCATION: (2678)..(2678)
<223> OTHER INFORMATION: The 'Xaa' at location 2678 stands for Arg, or
      His.
<220> FEATURE:
<221> NAME/KEY: misc_feature
<222> LOCATION: (2701)..(2701)
<223> OTHER INFORMATION: The 'Xaa' at location 2701 stands for Arg, or
      Pro.

<400> SEQUENCE: 2

Met Ala Val Leu Leu Leu Leu Val Val Glu Ala Gly Ala Ile Leu
1               5                   10                  15

Ala Pro Ala Thr His Ala Cys Ser Ala Lys Gly Gln Tyr Xaa Leu Thr
            20                  25                  30

Asn Cys Cys Ala Leu Glu Asp Ile Gly Phe Cys Leu Glu Gly Gly Cys
        35                  40                  45

Leu Val Ala Leu Gly Cys Thr Ile Cys Thr Asp Arg Cys Trp Pro Leu
    50                  55                  60

Tyr Gln Ala Gly Leu Ala Val Arg Pro Gly Lys Ser Ala Ala Gln Leu
65                  70                  75                  80

Val Gly Glu Leu Gly Ser Leu Tyr Gly Pro Leu Ser Val Ser Ala Tyr
                85                  90                  95

Val Ala Gly Ile Leu Gly Leu Gly Glu Val Tyr Ser Gly Val Leu Thr
            100                 105                 110

Val Gly Val Ala Leu Thr Arg Arg Val Tyr Pro Val Pro Asn Leu Thr
        115                 120                 125

Cys Ala Val Glu Cys Glu Leu Lys Trp Glu Ser Glu Phe Trp Arg Trp
    130                 135                 140

Thr Glu Gln Leu Ala Ser Asn Tyr Trp Ile Leu Glu Tyr Leu Trp Lys
145                 150                 155                 160

Val Pro Phe Asp Phe Trp Arg Gly Val Met Ser Leu Thr Pro Leu Leu
                165                 170                 175

Val Cys Val Ala Ala Leu Leu Leu Glu Gln Arg Ile Val Met Val
            180                 185                 190

Phe Leu Leu Val Thr Met Ala Gly Met Ser Gln Gly Ala Pro Ala Ser
        195                 200                 205

Val Leu Gly Ser Arg Pro Phe Glu Ala Gly Leu Thr Trp Gln Ser Cys
    210                 215                 220

Ser Cys Arg Ser Asn Gly Ser Arg Val Pro Thr Gly Glu Arg Val Trp
225                 230                 235                 240

Glu Arg Gly Asn Val Thr Leu Leu Cys Asp Cys Pro Asn Gly Pro Trp
                245                 250                 255

Val Trp Val Pro Ala Leu Cys Gln Ala Ile Gly Trp Gly Asp Pro Ile
            260                 265                 270
```

```
Thr His Trp Ser His Gly Gln Asn Gln Trp Pro Leu Ser Cys Pro Gln
        275                 280                 285

Phe Val Tyr Gly Ala Val Ser Val Thr Cys Val Trp Gly Ser Val Ser
    290                 295                 300

Trp Phe Ala Ser Thr Gly Gly Arg Asp Ser Lys Val Asp Val Trp Ser
305                 310                 315                 320

Leu Val Pro Val Gly Ser Ala Ser Cys Thr Ile Ala Ala Leu Gly Ser
                325                 330                 335

Ser Asp Arg Asp Thr Val Val Glu Leu Ser Glu Trp Gly Ile Pro Cys
            340                 345                 350

Ala Thr Cys Ile Leu Asp Arg Arg Pro Ala Ser Cys Gly Thr Cys Val
        355                 360                 365

Arg Asp Cys Trp Pro Glu Thr Gly Ser Val Arg Phe Pro Phe His Arg
    370                 375                 380

Cys Gly Ala Gly Pro Arg Leu Thr Arg Asp Leu Glu Ala Val Pro Phe
385                 390                 395                 400

Val Asn Arg Thr Thr Pro Phe Thr Ile Arg Gly Pro Leu Gly Asn Gln
                405                 410                 415

Gly Arg Gly Asn Pro Val Arg Ser Pro Leu Gly Phe Gly Ser Tyr Thr
            420                 425                 430

Met Thr Lys Ile Arg Asp Ser Leu His Leu Val Lys Cys Pro Thr Pro
        435                 440                 445

Ala Ile Glu Pro Pro Thr Gly Thr Phe Gly Phe Pro Gly Val Pro
    450                 455                 460

Pro Leu Asn Asn Cys Met Leu Leu Gly Thr Glu Val Ser Glu Val Leu
465                 470                 475                 480

Gly Gly Ala Gly Leu Thr Gly Gly Phe Tyr Glu Pro Leu Val Arg Arg
                485                 490                 495

Cys Ser Glu Leu Met Gly Arg Arg Asn Pro Val Cys Pro Gly Phe Ala
            500                 505                 510

Trp Leu Ser Ser Gly Arg Pro Asp Gly Phe Ile His Val Gln Gly His
        515                 520                 525

Leu Gln Glu Val Asp Ala Gly Asn Phe Ile Pro Pro Arg Trp Leu
    530                 535                 540

Leu Leu Asp Phe Val Phe Val Leu Leu Tyr Leu Met Lys Leu Ala Glu
545                 550                 555                 560

Ala Arg Leu Val Pro Leu Ile Leu Leu Leu Trp Trp Trp Val Asn
                565                 570                 575

Gln Leu Ala Val Leu Xaa Val Xaa Ala Ala Xaa Ala Ala Val Ala Gly
            580                 585                 590

Glu Val Phe Ala Gly Pro Ala Leu Ser Trp Cys Leu Gly Leu Pro Phe
        595                 600                 605

Val Ser Met Ile Leu Gly Leu Ala Asn Leu Val Leu Tyr Phe Arg Trp
    610                 615                 620

Met Gly Pro Gln Arg Leu Met Phe Leu Val Leu Trp Lys Leu Ala Arg
625                 630                 635                 640

Gly Ala Phe Pro Leu Ala Leu Leu Met Gly Ile Ser Ala Thr Arg Gly
                645                 650                 655

Arg Thr Ser Val Leu Gly Ala Glu Phe Cys Phe Asp Val Thr Phe Glu
            660                 665                 670

Val Asp Thr Ser Val Leu Gly Trp Val Val Ala Ser Val Ala Trp
        675                 680                 685

Ala Ile Ala Leu Leu Ser Ser Met Ser Ala Gly Gly Trp Lys His Lys
    690                 695                 700
```

-continued

Ala Ile Ile Tyr Arg Thr Trp Cys Lys Gly Tyr Gln Ala Leu Arg Gln
705                 710                 715                 720

Arg Val Val Arg Ser Pro Leu Gly Glu Gly Arg Pro Thr Lys Pro Leu
            725                 730                 735

Thr Ile Ala Trp Cys Leu Ala Ser Tyr Ile Trp Pro Asp Ala Val Met
            740                 745                 750

Leu Val Val Val Ala Met Val Leu Leu Phe Gly Leu Phe Asp Ala Leu
            755                 760                 765

Asp Trp Ala Leu Glu Glu Leu Leu Val Ser Arg Pro Ser Leu Arg Arg
            770                 775                 780

Leu Ala Arg Val Val Glu Cys Cys Val Met Ala Gly Glu Lys Ala Thr
785                 790                 795                 800

Thr Val Arg Leu Val Ser Lys Met Cys Ala Arg Gly Ala Tyr Leu Phe
            805                 810                 815

Asp His Met Gly Ser Phe Ser Arg Ala Val Lys Glu Arg Leu Leu Glu
            820                 825                 830

Trp Asp Ala Ala Leu Glu Xaa Leu Ser Phe Thr Arg Thr Asp Cys Arg
            835                 840                 845

Ile Ile Arg Asp Ala Ala Arg Thr Leu Ser Cys Gly Gln Cys Val Met
850                 855                 860

Gly Leu Pro Val Val Ala Arg Arg Gly Asp Glu Val Leu Ile Gly Val
865                 870                 875                 880

Phe Gln Asp Val Asn His Leu Pro Pro Gly Phe Xaa Pro Thr Ala Pro
            885                 890                 895

Val Val Ile Arg Arg Cys Gly Lys Gly Phe Leu Gly Val Thr Lys Ala
            900                 905                 910

Ala Leu Thr Gly Arg Asp Pro Asp Leu His Pro Gly Asn Val Met Val
            915                 920                 925

Leu Gly Thr Ala Thr Ser Arg Ser Met Gly Thr Cys Leu Asn Gly Leu
            930                 935                 940

Leu Phe Thr Thr Phe His Gly Ala Ser Ser Arg Thr Ile Ala Thr Pro
945                 950                 955                 960

Val Gly Ala Leu Asn Pro Arg Trp Trp Ser Ala Ser Asp Asp Val Thr
            965                 970                 975

Val Tyr Pro Leu Pro Asp Gly Ala Asn Ser Leu Val Pro Cys Ser Cys
            980                 985                 990

Gln Ala Glu Ser Cys Trp Val Xaa Arg Ser Asp Gly Ala Leu Cys His
            995                 1000                1005

Gly Leu Ser Lys Gly Asp Lys Val Glu Leu Asp Val Ala Met Glu
    1010                1015                1020

Val Ala Asp Phe Arg Gly Ser Ser Gly Ser Pro Val Leu Cys Asp
    1025                1030                1035

Glu Gly His Ala Val Gly Met Leu Val Ser Val Leu His Ser Gly
    1040                1045                1050

Gly Arg Val Thr Ala Ala Arg Phe Thr Arg Pro Trp Thr Gln Val
    1055                1060                1065

Pro Thr Asp Ala Lys Thr Thr Thr Glu Pro Pro Val Pro Ala
    1070                1075                1080

Lys Gly Val Phe Lys Glu Pro Leu Phe Met Pro Thr Gly Ala
    1085                1090                1095

Gly Lys Ser Thr Arg Val Pro Leu Glu Tyr Gly Asn Met Gly His
    1100                1105                1110

Lys Val Leu Ile Leu Asn Pro Ser Val Ala Thr Val Arg Ala Met
    1115                1120                1125

```
Gly Pro Tyr Met Glu Arg Leu Ala Gly Lys His Pro Ser Ile Phe
    1130                1135                1140

Cys Gly His Asp Thr Thr Ala Phe Thr Arg Ile Thr Asp Ser Pro
    1145                1150                1155

Leu Thr Tyr Ser Thr Tyr Gly Arg Phe Leu Ala Asn Pro Arg Gln
    1160                1165                1170

Met Leu Arg Gly Val Ser Val Val Ile Cys Asp Glu Cys His Ser
    1175                1180                1185

His Asp Ser Thr Val Leu Leu Gly Ile Gly Arg Val Arg Asp Val
    1190                1195                1200

Ala Arg Gly Cys Gly Val Gln Leu Val Leu Tyr Ala Thr Ala Thr
    1205                1210                1215

Pro Pro Gly Ser Pro Met Thr Gln His Pro Ser Ile Ile Glu Thr
    1220                1225                1230

Lys Leu Asp Val Gly Glu Ile Pro Phe Tyr Gly His Gly Ile Pro
    1235                1240                1245

Leu Glu Arg Met Arg Thr Gly Arg His Leu Val Phe Cys His Ser
    1250                1255                1260

Lys Ala Glu Cys Glu Arg Leu Ala Gly Gln Phe Ser Ala Arg Gly
    1265                1270                1275

Val Asn Ala Ile Ala Tyr Tyr Arg Gly Lys Asp Ser Ser Ile Ile
    1280                1285                1290

Lys Asp Gly Asp Leu Val Val Cys Ala Thr Asp Ala Leu Ser Thr
    1295                1300                1305

Gly Tyr Thr Gly Asn Phe Asp Ser Val Thr Asp Cys Gly Leu Val
    1310                1315                1320

Val Glu Glu Val Val Glu Val Thr Leu Asp Pro Thr Ile Thr Ile
    1325                1330                1335

Ser Leu Arg Thr Val Pro Ala Ser Ala Glu Leu Ser Met Gln Arg
    1340                1345                1350

Arg Gly Arg Thr Gly Arg Gly Arg Ser Gly Arg Tyr Tyr Tyr Ala
    1355                1360                1365

Gly Val Gly Lys Ala Pro Ala Gly Val Val Arg Ser Gly Pro Val
    1370                1375                1380

Trp Ser Ala Val Glu Ala Gly Val Thr Trp Tyr Gly Met Glu Pro
    1385                1390                1395

Asp Leu Thr Ala Asn Leu Leu Arg Leu Tyr Asp Asp Cys Pro Tyr
    1400                1405                1410

Thr Ala Ala Val Ala Ala Asp Ile Gly Glu Ala Ala Val Phe Phe
    1415                1420                1425

Ala Gly Leu Ala Pro Leu Arg Met His Pro Asp Val Ser Trp Ala
    1430                1435                1440

Lys Val Arg Gly Val Asn Trp Pro Leu Leu Val Gly Val Gln Arg
    1445                1450                1455

Thr Met Cys Arg Glu Thr Leu Ser Pro Gly Pro Ser Asp Asp Pro
    1460                1465                1470

Gln Trp Ala Gly Leu Lys Gly Pro Asn Pro Val Pro Leu Leu Leu
    1475                1480                1485

Arg Trp Gly Asn Asp Leu Pro Ser Lys Val Ala Gly His His Ile
    1490                1495                1500

Val Asp Asp Leu Val Arg Arg Leu Gly Val Ala Glu Gly Tyr Val
    1505                1510                1515
```

```
Arg Cys Asp Ala Xaa Pro Ile Leu Met Val Gly Leu Ala Ile Ala
1520                1525                1530

Gly Gly Met Ile Tyr Ala Ser Tyr Thr Gly Ser Leu Val Val Val
1535                1540                1545

Thr Asp Trp Asp Val Lys Gly Gly Gly Asn Pro Leu Tyr Arg Ser
1550                1555                1560

Gly Asp Gln Ala Thr Pro Gln Pro Val Val Gln Val Pro Pro Val
1565                1570                1575

Asp His Arg Pro Gly Gly Glu Ser Ala Pro Arg Asp Ala Lys Thr
1580                1585                1590

Val Thr Asp Ala Val Ala Ala Ile Gln Val Asn Cys Asp Trp Ser
1595                1600                1605

Val Met Thr Leu Ser Ile Gly Glu Val Leu Thr Leu Ala Gln Ala
1610                1615                1620

Lys Thr Ala Glu Ala Tyr Ala Ala Thr Ser Arg Trp Leu Ala Gly
1625                1630                1635

Cys Tyr Thr Gly Thr Arg Ala Val Pro Thr Val Ser Ile Val Asp
1640                1645                1650

Lys Leu Phe Ala Gly Gly Trp Ala Ala Val Val Gly His Cys His
1655                1660                1665

Ser Val Ile Ala Ala Ala Val Ala Ala Tyr Gly Ala Ser Arg Ser
1670                1675                1680

Pro Pro Leu Ala Ala Ala Ser Tyr Leu Met Gly Leu Gly Val
1685                1690                1695

Gly Gly Asn Ala Gln Ala Arg Leu Ala Ser Ala Leu Leu Leu Gly
1700                1705                1710

Ala Ala Gly Thr Ala Leu Gly Thr Pro Val Val Gly Leu Thr Met
1715                1720                1725

Ala Gly Ala Phe Met Gly Gly Ala Ser Val Ser Pro Ser Leu Val
1730                1735                1740

Thr Val Leu Leu Gly Ala Val Gly Gly Trp Glu Gly Val Val Asn
1745                1750                1755

Ala Ala Ser Leu Val Phe Asp Phe Met Ala Gly Lys Leu Ser Thr
1760                1765                1770

Glu Asp Leu Trp Tyr Ala Ile Pro Val Leu Thr Ser Pro Xaa Ala
1775                1780                1785

Gly Leu Ala Gly Ile Ala Leu Gly Leu Val Leu Tyr Ser Ala Asn
1790                1795                1800

Asn Ser Gly Thr Thr Thr Trp Leu Asn Arg Leu Leu Thr Thr Leu
1805                1810                1815

Pro Arg Ser Ser Cys Ile Pro Asp Ser Tyr Phe Gln Gln Ala Asp
1820                1825                1830

Tyr Cys Asp Lys Val Ser Ala Ile Val Arg Arg Leu Ser Leu Thr
1835                1840                1845

Arg Thr Val Val Ala Leu Val Asn Arg Glu Pro Lys Val Asp Glu
1850                1855                1860

Val Gln Val Gly Tyr Val Trp Asp Leu Trp Glu Trp Val Met Arg
1865                1870                1875

Gln Val Arg Met Val Met Ser Arg Leu Arg Ala Leu Cys Pro Val
1880                1885                1890

Val Ser Leu Pro Leu Trp His Cys Gly Glu Gly Trp Ser Gly Glu
1895                1900                1905

Trp Leu Leu Asp Gly His Val Glu Ser Arg Cys Leu Cys Gly Cys
1910                1915                1920
```

-continued

Val Ile Thr Gly Asp Val Leu Asn Gly Gln Leu Lys Asp Pro Val
1925                1930                1935

Tyr Ser Thr Lys Leu Cys Arg His Tyr Trp Met Gly Thr Val Pro
1940                1945                1950

Val Asn Met Leu Gly Tyr Gly Glu Thr Ser Pro Leu Leu Ala Ser
1955                1960                1965

Asp Thr Pro Lys Val Val Pro Phe Gly Thr Ser Gly Trp Ala Glu
1970                1975                1980

Val Val Val Thr Pro Thr His Val Val Ile Arg Arg Thr Ser Cys
1985                1990                1995

Tyr Lys Leu Leu Arg Gln Gln Ile Leu Ser Ala Ala Val Ala Glu
2000                2005                2010

Pro Tyr Tyr Val Asp Gly Ile Pro Val Ser Trp Glu Ala Asp Ala
2015                2020                2025

Arg Ala Pro Ala Met Val Tyr Gly Pro Gly Gln Ser Val Thr Ile
2030                2035                2040

Asp Gly Glu Arg Tyr Thr Leu Pro His Gln Leu Arg Met Arg Asn
2045                2050                2055

Val Ala Pro Ser Glu Val Ser Ser Glu Val Ser Ile Glu Ile Gly
2060                2065                2070

Thr Glu Thr Glu Asp Ser Glu Leu Thr Glu Ala Asp Leu Pro Pro
2075                2080                2085

Ala Ala Ala Ala Leu Gln Ala Ile Glu Asn Ala Ala Arg Ile Leu
2090                2095                2100

Glu Pro His Ile Asp Val Xaa Met Glu Asp Cys Ser Thr Pro Ser
2105                2110                2115

Leu Cys Gly Ser Ser Arg Glu Met Pro Val Trp Gly Glu Asp Ile
2120                2125                2130

Pro Arg Thr Pro Ser Pro Ala Leu Ile Ser Val Thr Glu Ser Ser
2135                2140                2145

Ser Asp Glu Lys Thr Leu Ser Val Thr Ser Ser Gln Glu Asp Thr
2150                2155                2160

Pro Ser Ser Asp Ser Phe Glu Val Ile Gln Glu Ser Asp Thr Ala
2165                2170                2175

Glu Ser Glu Glu Ser Val Phe Asn Val Ala Leu Ser Val Leu Lys
2180                2185                2190

Ala Leu Phe Pro Gln Ser Asp Ala Thr Arg Lys Leu Thr Val Lys
2195                2200                2205

Met Ser Cys Cys Val Glu Lys Ser Val Thr Arg Phe Phe Ser Leu
2210                2215                2220

Gly Leu Thr Val Ala Asp Val Ala Ser Leu Cys Glu Met Glu Ile
2225                2230                2235

Gln Asn His Thr Ala Tyr Cys Asp Lys Val Arg Thr Pro Leu Glu
2240                2245                2250

Leu Gln Val Gly Cys Leu Val Gly Asn Glu Leu Thr Phe Glu Cys
2255                2260                2265

Asp Lys Cys Glu Ala Arg Gln Glu Thr Leu Ala Ser Phe Ser Tyr
2270                2275                2280

Ile Trp Ser Gly Val Pro Leu Thr Arg Ala Thr Pro Ala Lys Pro
2285                2290                2295

Pro Val Val Arg Pro Val Gly Ser Leu Leu Val Ala Asp Thr Thr
2300                2305                2310

```
Lys Val Tyr Val Thr Asn Pro Asp Asn Val Gly Arg Arg Val Asp
2315                2320                2325

Lys Val Thr Phe Trp Arg Ala Pro Arg Val His Asp Lys Phe Leu
2330                2335                2340

Val Asp Ser Ile Glu Arg Ala Arg Arg Ala Ala Gln Gly Cys Leu
2345                2350                2355

Ser Met Gly Tyr Thr Tyr Glu Glu Ala Ile Arg Thr Val Arg Pro
2360                2365                2370

His Ala Ala Met Gly Trp Gly Ser Lys Val Ser Val Lys Asp Leu
2375                2380                2385

Ala Thr Pro Ala Gly Lys Met Ala Val His Asp Arg Leu Gln Glu
2390                2395                2400

Ile Leu Glu Gly Thr Pro Val Pro Phe Thr Leu Thr Val Lys Lys
2405                2410                2415

Glu Val Phe Phe Lys Asp Arg Lys Glu Lys Ala Pro Arg Leu
2420                2425                2430

Ile Val Phe Pro Pro Leu Asp Phe Arg Ile Ala Glu Lys Leu Ile
2435                2440                2445

Leu Gly Asp Pro Gly Arg Val Ala Lys Ala Gly Val Gly Gly Ala
2450                2455                2460

Tyr Ala Phe Gln Tyr Thr Pro Asn Gln Arg Val Lys Glu Met Leu
2465                2470                2475

Lys Leu Trp Glu Ser Lys Lys Thr Pro Cys Ala Ile Cys Val Asp
2480                2485                2490

Ala Thr Cys Phe Asp Ser Ser Ile Thr Glu Glu Asp Val Ala Leu
2495                2500                2505

Glu Thr Glu Leu Tyr Ala Leu Ala Ser Asp His Pro Glu Trp Val
2510                2515                2520

Arg Ala Leu Gly Lys Tyr Xaa Ala Ser Gly Thr Met Val Thr Pro
2525                2530                2535

Glu Gly Val Pro Val Gly Glu Arg Tyr Cys Arg Ser Ser Gly Val
2540                2545                2550

Leu Thr Thr Ser Ala Ser Asn Cys Leu Thr Cys Tyr Ile Lys Val
2555                2560                2565

Arg Ala Ala Cys Glu Arg Ile Gly Leu Lys Asn Val Ser Leu Leu
2570                2575                2580

Ile Ala Gly Asp Asp Cys Leu Ile Val Cys Glu Arg Pro Val Cys
2585                2590                2595

Asp Pro Cys Glu Ala Leu Gly Arg Thr Leu Ala Ser Tyr Gly Tyr
2600                2605                2610

Ala Cys Glu Pro Ser Tyr His Ala Ser Leu Asp Thr Ala Pro Phe
2615                2620                2625

Cys Ser Thr Trp Leu Ala Glu Cys Asn Ala Asp Gly Xaa Arg His
2630                2635                2640

Phe Phe Leu Thr Thr Asp Phe Arg Arg Pro Leu Ala Arg Met Ser
2645                2650                2655

Ser Glu Tyr Ser Asp Pro Met Ala Ser Ala Ile Gly Tyr Ile Leu
2660                2665                2670

Leu Tyr Pro Trp Xaa Pro Ile Thr Arg Trp Val Ile Ile Pro His
2675                2680                2685

Val Leu Thr Cys Ala Ser Ser Arg Gly Gly Gly Thr Xaa Ser Asp
2690                2695                2700

Pro Val Trp Cys Gln Val His Gly Asn Tyr Tyr Lys Phe Pro Leu
2705                2710                2715
```

| | | | | | | | | | | | |
|---|---|---|---|---|---|---|---|---|---|---|---|
| Asp | Lys | Leu | Pro | Asn | Ile | Ile | Val | Ala | Leu | His | Gly | Pro | Ala | Ala |
| | 2720 | | | | 2725 | | | | 2730 | | |

Leu Arg Val Thr Ala Asp Thr Thr Lys Thr Lys Met Glu Ala Gly
   2735                2740               2745

Lys Val Leu Ser Asp Leu Lys Leu Pro Gly Leu Ala Val His Arg
   2750                2755               2760

Lys Lys Ala Gly Ala Leu Arg Thr Arg Met Leu Arg Ser Arg Gly
   2765                2770               2775

Trp Ala Glu Leu Ala Arg Gly Leu Leu Trp His Pro Gly Leu Arg
   2780                2785               2790

Leu Pro Pro Pro Glu Ile Ala Gly Ile Pro Gly Gly Phe Pro Leu
   2795                2800               2805

Ser Pro Pro Tyr Met Gly Val Val His Gln Leu Asp Phe Thr Ala
   2810                2815               2820

Gln Arg Ser Arg Trp Arg Trp Leu Gly Phe Leu Ala Leu Leu Ile
   2825                2830               2835

Val Ala Leu Phe Gly
   2840

```
<210> SEQ ID NO 3
<211> LENGTH: 936
<212> TYPE: DNA
<213> ORGANISM: Hepatitis GB virus C
<220> FEATURE:
<221> NAME/KEY: CDS
<222> LOCATION: (1)..(936)

<400> SEQUENCE: 3
``` acc ata gcc gca ctg gga tct tcg gat cgc gac aca gtg gtt gag ctc    48
Thr Ile Ala Ala Leu Gly Ser Ser Asp Arg Asp Thr Val Val Glu Leu
1               5                   10                  15 tcc gag tgg gga att ccc tgc gcc act tgt atc ctg gac agg cgg cct    96
Ser Glu Trp Gly Ile Pro Cys Ala Thr Cys Ile Leu Asp Arg Arg Pro
            20                  25                  30 gcc tcg tgt ggc acc tgt gtg agg gac tgc tgg ccc gag acc ggg tcg   144
Ala Ser Cys Gly Thr Cys Val Arg Asp Cys Trp Pro Glu Thr Gly Ser
        35                  40                  45 gta cgt ttc cca ttc cac agg tgt ggc gcg gga ccg agg ctg acc aga   192
Val Arg Phe Pro Phe His Arg Cys Gly Ala Gly Pro Arg Leu Thr Arg
    50                  55                  60 gac ctt gag gct gtg ccc ttc gtc aat agg aca act ccc ttc acc ata   240
Asp Leu Glu Ala Val Pro Phe Val Asn Arg Thr Thr Pro Phe Thr Ile
65                  70                  75                  80 agg ggg ccc ctg ggc aac cag ggg cga ggc aac ccg gtg cgg tcg ccc   288
Arg Gly Pro Leu Gly Asn Gln Gly Arg Gly Asn Pro Val Arg Ser Pro
                85                  90                  95 ttg ggt ttt ggg tcc tac acc atg acc aag atc cga gac tcc tta cac   336
Leu Gly Phe Gly Ser Tyr Thr Met Thr Lys Ile Arg Asp Ser Leu His
            100                 105                 110 ttg gtg aaa tgt ccc acc cca gcc att gag cct ccc acc gga acg ttt   384
Leu Val Lys Cys Pro Thr Pro Ala Ile Glu Pro Pro Thr Gly Thr Phe
        115                 120                 125 ggg ttc ttc cca gga gtc ccc ccc ctt aac aac tgc atg ctt ctc ggc   432
Gly Phe Phe Pro Gly Val Pro Pro Leu Asn Asn Cys Met Leu Leu Gly
    130                 135                 140 act gag gtg tca gag gta ttg ggt ggg gcg ggc ctc act ggg ggg ttt   480
Thr Glu Val Ser Glu Val Leu Gly Gly Ala Gly Leu Thr Gly Gly Phe
145                 150                 155                 160

```
tac gaa cct ctg gtg cgg cgg tgt tca gag ctg atg ggt cgg cgg aat    528
Tyr Glu Pro Leu Val Arg Arg Cys Ser Glu Leu Met Gly Arg Arg Asn
                165                 170                 175 ccg gtc tgc ccg ggg ttt gca tgg ctc tct tcg gga cgg cct gat ggg    576
Pro Val Cys Pro Gly Phe Ala Trp Leu Ser Ser Gly Arg Pro Asp Gly
            180                 185                 190 ttc ata cat gtt cag ggc cac ttg cag gag gtg gat gcg ggc aac ttc    624
Phe Ile His Val Gln Gly His Leu Gln Glu Val Asp Ala Gly Asn Phe
        195                 200                 205 att ccg ccc cca cgc tgg ttg ctc ttg gac ttt gta ttt gtc ctg tta    672
Ile Pro Pro Pro Arg Trp Leu Leu Leu Asp Phe Val Phe Val Leu Leu
    210                 215                 220 tac ctg atg aag ctg gca gag gca cgg ttg gtc ccg ctg atc ctc ctc    720
Tyr Leu Met Lys Leu Ala Glu Ala Arg Leu Val Pro Leu Ile Leu Leu
225                 230                 235                 240 ctg cta tgg tgg tgg gtg aac cag ttg gcg gtc ctt gkt gtg scg gct    768
Leu Leu Trp Trp Trp Val Asn Gln Leu Ala Val Leu Xaa Val Xaa Ala
                245                 250                 255 gck crc gcc gcc gtg gct gga gag gtg ttt gcg ggc cct gcc ttg tcc    816
Ala Xaa Ala Ala Val Ala Gly Glu Val Phe Ala Gly Pro Ala Leu Ser
            260                 265                 270 tgg tgt ctg ggc cta ccc ttc gtg agt atg atc ctg ggg cta gca aac    864
Trp Cys Leu Gly Leu Pro Phe Val Ser Met Ile Leu Gly Leu Ala Asn
        275                 280                 285 ctg gtg ttg tac ttc cgc tgg atg ggt cct caa cgc ctg atg ttc ctc    912
Leu Val Leu Tyr Phe Arg Trp Met Gly Pro Gln Arg Leu Met Phe Leu
    290                 295                 300 gtg ttg tgg aag ctc gct cgg ggg                                    936
Val Leu Trp Lys Leu Ala Arg Gly
305                 310

<210> SEQ ID NO 4
<211> LENGTH: 312
<212> TYPE: PRT
<213> ORGANISM: Hepatitis GB virus C
<220> FEATURE:
<221> NAME/KEY: misc_feature
<222> LOCATION: (253)..(253)
<223> OTHER INFORMATION: The 'Xaa' at location 253 stands for Gly, or
      Val.
<220> FEATURE:
<221> NAME/KEY: misc_feature
<222> LOCATION: (255)..(255)
<223> OTHER INFORMATION: The 'Xaa' at location 255 stands for Ala, or
      Pro.
<220> FEATURE:
<221> NAME/KEY: misc_feature
<222> LOCATION: (258)..(258)
<223> OTHER INFORMATION: The 'Xaa' at location 258 stands for Arg, or
      His.

<400> SEQUENCE: 4

Thr Ile Ala Ala Leu Gly Ser Ser Asp Arg Asp Thr Val Val Glu Leu
1               5                   10                  15

Ser Glu Trp Gly Ile Pro Cys Ala Thr Cys Ile Leu Asp Arg Arg Pro
            20                  25                  30

Ala Ser Cys Gly Thr Cys Val Arg Asp Cys Trp Pro Glu Thr Gly Ser
        35                  40                  45

Val Arg Phe Pro Phe His Arg Cys Gly Ala Gly Pro Arg Leu Thr Arg
    50                  55                  60

Asp Leu Glu Ala Val Pro Phe Val Asn Arg Thr Thr Pro Phe Thr Ile
65                  70                  75                  80

Arg Gly Pro Leu Gly Asn Gln Gly Arg Gly Asn Pro Val Arg Ser Pro
                85                  90                  95
```

```
Leu Gly Phe Gly Ser Tyr Thr Met Thr Lys Ile Arg Asp Ser Leu His
            100                 105                 110

Leu Val Lys Cys Pro Thr Pro Ala Ile Glu Pro Pro Thr Gly Thr Phe
        115                 120                 125

Gly Phe Phe Pro Gly Val Pro Pro Leu Asn Asn Cys Met Leu Leu Gly
    130                 135                 140

Thr Glu Val Ser Glu Val Leu Gly Gly Ala Gly Leu Thr Gly Gly Phe
145                 150                 155                 160

Tyr Glu Pro Leu Val Arg Arg Cys Ser Glu Leu Met Gly Arg Arg Asn
                165                 170                 175

Pro Val Cys Pro Gly Phe Ala Trp Leu Ser Ser Gly Arg Pro Asp Gly
        180                 185                 190

Phe Ile His Val Gln Gly His Leu Gln Glu Val Asp Ala Gly Asn Phe
    195                 200                 205

Ile Pro Pro Pro Arg Trp Leu Leu Leu Asp Phe Val Phe Val Leu Leu
210                 215                 220

Tyr Leu Met Lys Leu Ala Glu Ala Arg Leu Val Pro Leu Ile Leu Leu
225                 230                 235                 240

Leu Leu Trp Trp Trp Val Asn Gln Leu Ala Val Leu Xaa Val Xaa Ala
                245                 250                 255

Ala Xaa Ala Ala Val Ala Gly Glu Val Phe Ala Gly Pro Ala Leu Ser
        260                 265                 270

Trp Cys Leu Gly Leu Pro Phe Val Ser Met Ile Leu Gly Leu Ala Asn
            275                 280                 285

Leu Val Leu Tyr Phe Arg Trp Met Gly Pro Gln Arg Leu Met Phe Leu
        290                 295                 300

Val Leu Trp Lys Leu Ala Arg Gly
305                 310

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Leu Thr Gly Gly Phe Tyr Glu Pro Leu
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 6

Gly Gly Ala Gly Leu Thr Gly Gly Phe Tyr Glu Pro Leu Val Arg Arg
1               5                   10                  15

Cys

<210> SEQ ID NO 7
<211> LENGTH: 13
<212> TYPE: PRT
<213> ORGANISM: Artificial Sequence
<220> FEATURE:
<223> OTHER INFORMATION: Synthetic Peptide
```

```
<400> SEQUENCE: 7

Leu Thr Gly Gly Phe Tyr Glu Pro Leu Val Arg Arg Cys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 8

Phe Tyr Glu Pro Leu Val Arg Arg Cys
1               5

<210> SEQ ID NO 9
<211> LENGTH: 415
<212> TYPE: PRT
<213> ORGANISM: Hepatitis GB virus C

<400> SEQUENCE: 9

Val Gly Tyr Val Trp Asp Leu Trp Glu Trp Ile Met Arg Gln Val Arg
1               5                   10                  15

Met Val Met Ala Arg Leu Arg Ala Leu Cys Pro Val Val Ser Leu Pro
                20                  25                  30

Leu Trp His Cys Gly Glu Gly Trp Ser Gly Glu Trp Leu Leu Asp Gly
            35                  40                  45

His Val Glu Ser Arg Cys Leu Cys Gly Cys Val Ile Thr Gly Asp Val
        50                  55                  60

Leu Asn Gly Gln Leu Lys Glu Pro Val Tyr Ser Thr Lys Leu Cys Arg
65                  70                  75                  80

His Tyr Trp Met Gly Thr Val Pro Val Asn Met Leu Gly Tyr Gly Glu
                85                  90                  95

Thr Ser Pro Leu Leu Ala Ser Asp Thr Pro Lys Val Val Pro Phe Gly
                100                 105                 110

Thr Ser Gly Trp Ala Glu Val Val Val Thr Pro Thr His Val Val Ile
            115                 120                 125

Arg Arg Thr Ser Ala Tyr Lys Leu Leu Arg Gln Gln Ile Leu Ser Ala
        130                 135                 140

Ala Val Ala Glu Pro Tyr Tyr Val Asp Gly Ile Pro Val Ser Trp Asp
145                 150                 155                 160

Ala Asp Ala Arg Ala Pro Ala Met Val Tyr Gly Pro Gly Gln Ser Val
                165                 170                 175

Thr Ile Asp Gly Glu Arg Tyr Thr Leu Pro His Gln Leu Arg Leu Arg
            180                 185                 190

Asn Val Ala Pro Ser Glu Val Ser Ser Glu Val Ser Ile Asp Ile Gly
        195                 200                 205

Thr Glu Thr Glu Asp Ser Glu Leu Thr Glu Ala Asp Leu Pro Pro Ala
    210                 215                 220

Ala Ala Ala Leu Gln Ala Ile Glu Asn Ala Ala Arg Ile Leu Glu Pro
225                 230                 235                 240

His Ile Asp Val Ile Met Glu Asp Cys Ser Thr Pro Ser Leu Cys Gly
                245                 250                 255

Ser Ser Arg Glu Met Pro Val Trp Gly Glu Asp Ile Pro Arg Thr Pro
            260                 265                 270

Ser Ser Pro Ala Leu Ile Ser Val Thr Glu Ser Pro Ser Asp Glu Lys
        275                 280                 285
```

```
Thr Pro Ser Val Ser Ser Gln Glu Asp Thr Pro Ser Ser Asp Ser
    290                 295                 300

Phe Glu Val Ile Gln Glu Ser Glu Thr Ala Glu Gly Glu Glu Ser Val
305                 310                 315                 320

Phe Asn Val Ala Leu Ser Val Leu Lys Ala Leu Phe Pro Gln Ser Asp
                325                 330                 335

Ala Thr Arg Lys Leu Thr Val Lys Met Ser Cys Cys Val Glu Lys Ser
            340                 345                 350

Val Thr Arg Phe Phe Ser Leu Gly Leu Thr Val Ala Asp Val Ala Ser
        355                 360                 365

Leu Cys Glu Met Glu Ile Gln Asn His Thr Ala Tyr Cys Asp Lys Val
    370                 375                 380

Arg Thr Pro Leu Glu Leu Gln Val Gly Cys Leu Val Gly Asn Glu Leu
385                 390                 395                 400

Thr Phe Glu Cys His Asn Cys Glu Ala Arg Gln Glu Thr Leu Ala
                405                 410                 415

<210> SEQ ID NO 10
<211> LENGTH: 16
<212> TYPE: PRT
<213> ORGANISM: Hepatitis GB virus C

<400> SEQUENCE: 10

Val Asp Gly Ile Pro Val Ser Trp Asp Ala Asp Ala Arg Ala Pro Ala
1               5                   10                  15

<210> SEQ ID NO 11
<211> LENGTH: 15
<212> TYPE: PRT
<213> ORGANISM: Hepatitis GB virus C

<400> SEQUENCE: 11

Asp Gly Ile Pro Val Ser Trp Asp Ala Asp Ala Arg Ala Pro Ala
1               5                   10                  15

<210> SEQ ID NO 12
<211> LENGTH: 14
<212> TYPE: PRT
<213> ORGANISM: Hepatitis GB virus C

<400> SEQUENCE: 12

Gly Ile Pro Val Ser Trp Asp Ala Asp Ala Arg Ala Pro Ala
1               5                   10

<210> SEQ ID NO 13
<211> LENGTH: 15
<212> TYPE: PRT
<213> ORGANISM: Hepatitis GB virus C

<400> SEQUENCE: 13

Val Asp Gly Ile Pro Val Ser Trp Asp Ala Asp Ala Arg Ala Pro
1               5                   10                  15

<210> SEQ ID NO 14
<211> LENGTH: 14
<212> TYPE: PRT
<213> ORGANISM: Hepatitis GB virus C

<400> SEQUENCE: 14

Val Asp Gly Ile Pro Val Ser Trp Asp Ala Asp Ala Arg Ala
1               5                   10
```

```
<210> SEQ ID NO 15
<211> LENGTH: 16
<212> TYPE: PRT
<213> ORGANISM: Hepatitis GB virus C

<400> SEQUENCE: 15

Val Asp Gly Ile Pro Val Ser Trp Glu Ala Asp Ala Arg Ala Pro Ala
1               5                   10                  15

<210> SEQ ID NO 16
<211> LENGTH: 21
<212> TYPE: PRT
<213> ORGANISM: Hepatitis C virus

<400> SEQUENCE: 16

Leu Asp Gly Val Arg Leu His Arg Phe Ala Pro Pro Cys Lys Pro Leu
1               5                   10                  15

Leu Arg Glu Glu Val
            20

<210> SEQ ID NO 17
<211> LENGTH: 21
<212> TYPE: PRT
<213> ORGANISM: Hepatitis C virus

<400> SEQUENCE: 17

Val Asp Gly Val Arg Leu His Arg Tyr Ala Pro Ala Cys Arg Pro Leu
1               5                   10                  15

Leu Arg Glu Glu Val
            20

<210> SEQ ID NO 18
<211> LENGTH: 21
<212> TYPE: PRT
<213> ORGANISM: Hepatitis C virus

<400> SEQUENCE: 18

Val Asp Gly Val Gln Ile His Arg Phe Ala Pro Ile Pro Lys Pro Phe
1               5                   10                  15

Phe Arg Asp Glu Val
            20

<210> SEQ ID NO 19
<211> LENGTH: 21
<212> TYPE: PRT
<213> ORGANISM: Hepatitis C virus

<400> SEQUENCE: 19

Val Asp Gly Val Arg Leu His Arg Tyr Ala Pro Pro Cys Lys Pro Leu
1               5                   10                  15

Leu Arg Glu Glu Ile
            20

<210> SEQ ID NO 20
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 20

Asp Val Ile Arg Ala Gly Pro Ala Trp Asp Ser Val Ala Pro Ala Asp
1               5                   10                  15
```

-continued

<210> SEQ ID NO 21
<211> LENGTH: 16
<212> TYPE: PRT
<213> ORGANISM: Hepatitis GB virus C

<400> SEQUENCE: 21

Val Asp Gly Ile Pro Val Ala Trp Asp Ala Asp Ala Arg Ala Pro Ala
1 5 10 15

<210> SEQ ID NO 22
<211> LENGTH: 16
<212> TYPE: PRT
<213> ORGANISM: Hepatitis GB virus C

<400> SEQUENCE: 22

Val Asp Gly Ile Pro Val Gly Trp Asp Ala Asp Ala Arg Ala Pro Ala
1 5 10 15

<210> SEQ ID NO 23
<211> LENGTH: 16
<212> TYPE: PRT
<213> ORGANISM: Hepatitis GB virus C

<400> SEQUENCE: 23

Val Asp Gly Ile Pro Val Glu Trp Asp Ala Asp Ala Arg Ala Pro Ala
1 5 10 15

<210> SEQ ID NO 24
<211> LENGTH: 16
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: The 'Xaa' at location 7 stands for Ser or Glu
<220> FEATURE:
<221> NAME/KEY: MISC_FEATURE
<222> LOCATION: (11)..(11)
<223> OTHER INFORMATION: The 'Xaa' at location 11 stands for Asp or Glu

<400> SEQUENCE: 24

Val Asp Gly Ile Pro Val Xaa Trp Asp Ala Xaa Ala Arg Ala Pro Ala
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: The 'Xaa' at location 1 stands for Val or Leu
<220> FEATURE:
<221> NAME/KEY: MISC_FEATURE
<222> LOCATION: (4)..(4)
<223> OTHER INFORMATION: The 'Xaa' at location 4 stands for Ile or Val
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: The 'Xaa' at location 6 stands for Ser or His
<220> FEATURE:
<221> NAME/KEY: MISC_FEATURE
<222> LOCATION: (7)..(7)
<223> OTHER INFORMATION: The 'Xaa' at location 7 stands for Trp or Arg

```
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: The 'Xaa' at location 10 stands for Asp or Pro
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 25

Xaa Asp Gly Xaa Xaa Xaa Xaa Xaa Ala Xaa Xaa Xaa Xaa Pro Xaa
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 26

Ala Val Pro Asp Ala Gly Arg Ile Ala Pro Asp Val Ala Ser Asp Trp
1               5                   10                  15
```

FLAVIVIRUS NS5A PROTEINS FOR THE TREATMENT OF HIV

This application is a national phase application under 35 U.S.C. §371 of International Patent Application No. PCT/US2008/057719 filed Mar. 20, 2008 which claims priority to U.S. Provisional Application 60/896,454, filed Mar. 22, 2007, and U.S. Provisional Application 60/947,836, filed Jul. 3, 2007, the entire contents are incorporated herein by reference.

This invention was made with government support under grant number AI 58740 awarded by the National Institute of Health. The government has certain rights in the invention.

BACKGROUND OF THE INVENTION

I. Field of the Invention

The present invention relates generally to the fields of molecular biology and virology. More particularly, it concerns methods and compositions to treat, inhibit or prevent HIV infection.

II. Description of Related Art

A. GB Virus Type C

GB virus type C (GBV-C), also known as hepatitis G virus (HGV), is a virus whose genomic organization and nucleotide sequence places it in the Flavivirus family (Robertson et al., 1998). It is the most closely related human virus to hepatitis C virus (HCV) (Leary et al., 1996; Linnen et al., 1996; Simons et al., 1995). It has been suggested that these viruses should be classified together with non-human GB-hepatitis agents as the hepacivirus genus. Although GBV-C was originally associated with post-transfusion hepatitis in humans (Linnen et al., 1996), subsequent epidemiological studies indicated that it does not cause acute or chronic hepatitis (Alter et al., 1997a; Alter et al., 1997b). In addition, experimental GBV-C infection of chimpanzees was not associated with acute hepatitis (Bukh et al., 1998).

Persistent GBV-C viremia (as detected by RT-PCR) is common, with 0.9% to 3% of healthy U.S. blood donors and approximately 20%-30% of patients with HCV infection persistently infected with GBV-C (Dawson et al., 1996; Feucht et al., 1997; Simons et al., 1995a; Simons et al., 1995b; Tacke et al., 1997). Following infection, about 80% of people clear their viremia, concomitantly developing antibody to the GBV-C E2 protein (Feucht et al., 1997; Thomas et al., 1998). Thus, it is estimated that approximately 20% of infected people remain viremic for long periods of time. GBV-C appears to be transmitted primarily by parenteral exposure (Simons et al., 1995), although there are data suggesting that sexual and/or household transmission of GBV-C infection may occur (Akiyoshi et al., 1999; de Martino et al., 1998; Nerurkar et al., 1998; Tanaka et al., 1997; Wu et al., 1997).

B. GBV-C and HIV

During progressive human immunodeficiency virus type 1 (HIV-1) infection, the virus-specific immune responses of an infected subject gradually deteriorate, leading to the development of acquired immunodeficiency syndrome (AIDS). Most infected patients do not exhibit overt clinical manifestations of the disease for six to ten years following initial infection, however, most individuals infected with HIV eventually die from conditions or infections; that the individual's immune system is no longer equipped to fight. While treatment for AIDS has been forthcoming, no effective cure has been reported. Thus, preventative and treatment options against HIV infection and the development of AIDS remain highly desirable.

GBV-C has been investigated in the context of HIV infection. The course of HIV-1 infection is extremely variable among infected individuals, although the reasons for this observation are not fully understood. Individuals whose HIV disease progresses slowly are often called long-term non-progressors (LTNPs). The prevalence of LTNPs varies from 1% to 25% of infected people, depending upon the definition used (reviewed in Easterbrook, 1999). There are no specific clinical criteria for LTNP. However, non-progression generally implies the absence of HIV-related clinical disease 10 or more years following infection and an absolute CD4 count of $\geq 500$ cells/mm$^3$ (Easterbrook, 1999). Evaluation of LTNP's has identified HIV isolates with deletions in key replicative genes (Deacon et al., 1995) and host genetic factors, including specific HLA haplotypes (reviewed in reference Rowland-Jones, 1999). In some individuals, polymorphisms that result in absent or reduced expression of HIV co-receptors have been identified (Huang et al., 1996). However, these findings are uncommon and thought to account for no more than one-third of LTNP's (Rowland-Jones, 1999).

Persistent GBV-C infection is common in humans, with infection rates of approximately 0.9% to 3% in healthy blood donors, 20-30% in HCV-positive people (Dawson et al., 1996), and 35%-40% in HIV-positive individuals (Stapleton et al., 2004; Xiang et al., 2001). GBV-C infection can persist for decades in the absence of any clinical morbidity or mortality. Among immune-competent individuals, it is estimated that 60% to 75% of GBV-C-infected people clear the infection, concomitantly developing antibodies to the envelope glycoprotein E2 (Thomas et al., 1998). It is also known that GBV-C can be propagated in cultures of peripheral blood mononuclear cells (PBMC's) (Fogeda et al., 1999).

In 1998, Toyoda et al. found that hemophiliacs co-infected with HIV and GBV-C had a lower plasma HIV RNA concentration and a lower incidence of AIDS diagnoses compared to those infected with HIV alone (Toyoda et al., 1998), although the differences were not statistically significant. In contrast, Sabin and colleagues found an increased rate of AIDS and death in hemophiliacs "exposed" to GBV-C (Sabin et al., 1998) compared to non-exposed individuals. This study included HIV-positive subjects who were either GBV-C viremic as determined by detection of GBV-C RNA in plasma, or HIV-infected people who were not viremic but were anti-GBV-C E2 antibody-positive. Although the mortality rate was higher among the GBV-C "exposed" individuals, the results were not statistically significant. Looking at HIV-infected persons, Lefrère and colleagues reported a significant delay in the rate of CD4+ T cell decline, development of AIDS, and death in 23 HIV-positive individuals with GBV-C viremia compared to 72 HIV-infected people without GBV-C viremia (Lefrère et al., 1999). In that study, HIV-infected individuals who were also GBV-C-positive were compared to HIV-infected individuals who were GBV-C-negative. When these subjects were matched by age, sex, baseline HIV RNA load, and baseline CD4 T cell count, HIV disease progression appeared to be worse in GBV-C-negative subjects.

The interrelationship between HIV and GBV-C continues to be explored, with possible therapeutic aspects of GBV-C infection being examined.

SUMMARY OF THE INVENTION

Embodiments of the invention include composition or pharmaceutical compositions comprising an isolated NS5A peptide comprising an at most 10, 11, 12, 13, 14, 15, 16, 17, 18, 19, 20, 25, 30, 35, 40, 45, 50, 60, 65, 70, 75, 80, or 84 contiguous amino acid sequence of an NS5A polypeptide that comprise the sequence VDGIPV(S/E)WDA(D/E)ARAPA (SEQ ID NO: 24) or (V/L)DG(I/V)X(S/H)(W/R)XA(D/P)XXXPX (SEQ ID NO: 25), wherein in X is any amino acid, or a derivative or analog thereof. The composition may comprise 2, 3, 4, 5, 6 or more peptides or analogs. In certain aspects of the invention a composition can include a mimic or analog of a peptide described herein. In a further aspect, a peptide or mimic thereof can be a fusion peptide, modified peptide or molecular conjugate. The fusion peptide, modified peptide or molecular conjugate may include a targeting or localization domain. The targeting domain may target or localize a molecule to a cell surface receptor or a particular cell or cell type, e.g., T cell. In certain embodiments the cell surface receptor is the CD4 receptor.

In other aspects, a peptide or peptide mimetic can be formulated in a lipid vehicle, in particular a liposome. The peptide can also be formulated with an amphipathic peptide, an insect peptide, or pyrrhocoricin.

A peptide of the invention typically comprises residues 1-181, 152-181, 152-167, or 152-165 of GBV-C NS5A, or the corresponding sequences from other flavivirus NS5A proteins. In certain aspects the structure of such a peptide can be mimicked by a non-peptide containing molecule wherein the structural determinants of the NS5A peptide remain intact and maintain activity, e.g., HIV modulatory activity and CD4 expression modulatory activity. Peptides of the invention can be derived from various flaviviruses, the flavivirus can include DEN1, DEN2, DEN3, DEN4, YFV, TBEV, WNV, CSFV, BVDV, GBV-A, GBV-B, GBV-C, HGV, HCV2a, HCV3a, HCV2b, HCV1a and HCV1b.

In a further embodiment, methods of the invention are described for preventing, ameliorating, or treating HIV infection comprising administering to a subject a composition comprising an isolated peptide or peptide mimetic of the invention. In certain embodiments the peptide is a GBV-C NS5A peptide or a fusion peptide. The peptide further comprises a targeting domain, in particular a targeting domain for a cell surface receptor, such as but not limited to a CD4 receptor. The peptide can be formulated in a lipid vehicle, such as a liposome. The peptide can also be formulated with an amphipathic peptide, an insect peptide, or pyrrhocoricin. In certain aspects the peptide comprises residues 1-181, 152-181, 152-167, or 152-165 of GBV-C NS5A, or the corresponding equivalent sequences from other flavivirus NS5A proteins or an analog or mimetic thereof. Methods of the invention may further comprise administration of at least a second anti-HIV therapy. The second anti-HIV therapy may be administered before, during or after administration of a peptide. A second anti-HIV therapy includes HAART therapy, AZT therapy, and other anti-retroviral or anti-HIV therapies. The composition(s) of the invention may be administered at least or at most 2, 3, 4, 5, 6, 7, 8, 9, 10, or more times. Over 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more hours, days, weeks, or years.

Other embodiments of the invention include methods for preventing or treating HIV infection comprising administering to a subject a composition comprising an expression construct encoding a peptide of the invention. The expression construct can be a viral expression construct, such as but not limited to an adenovirus, a retrovirus, a lentivirus, an adeno-associated virus, a polyoma virus, a herpesvirus, or a pox virus. In certain aspects the expression construct is a non-viral expression construct. The expression construct may be dispersed in a lipid vehicle.

In still a further embodiment, the invention includes methods for modulating CD4 expression in a cell of a subject comprising administering to a subject a flavivirus NS5A peptide or polypeptide of the invention.

In yet another embodiment, there is provided a method for modulating T cell function comprising contacting a T cell with a flavivirus NS5A peptide or polypeptide. The peptide or polypeptide may be encoded by an expression construct, for example, a viral expression construct (e.g., an adenovirus, a retrovirus, a lentivirus, an adeno-associated virus, a polyoma virus, a herpesvirus, or a pox virus). The expression construct may also be a non-viral expression construct, and may be dispersed in a lipid vehicle. The expression construct may encode a full-length NS5A polypeptide, or a fusion polypeptide including NS5A. The flavivirus NS5A peptide or polypeptide may further comprises a targeting signal, such as a nuclear targeting signal. The T cell may be in a subject, such as a human subject. The subject may suffer from or be at risk of an allergic reaction, or suffer from or be at risk of an autoimmune disease. The subject may also be or will be a transplant recipient.

The flavivirus NS5A peptide or polypeptide may inhibit expression of a T cell surface receptor, for example, the CD4 receptor. The NS5A peptide or polypeptide may comprise an amino acid sequence of VDGIPV(S/E)WDA(D/E)ARAPA (SEQ ID NO: 24) or (V/L)DG(I/V)X(S/H)(W/R)XA(D/P)XXXPX (SEQ ID NO: 25). Alternatively, the flavivirus NS5A peptide or polypeptide comprises residues 1-181, 152-181, 152-167, or 152-165 of GBV-C NS5A, or the equivalent corresponding sequences thereto from other flavivirus NS5A proteins. The flavivirus may be selected from the group consisting of DEN1, DEN2, DEN3, DEN4, YFV, TBEV, WNV, CSFV, GBV-A, GBV-C, HGV, HCV2a, HCV3a, HCV2b, HCV1a and HCV1b.

Other embodiments include a method for modulating chemokine product by a T cell comprising contacting said T cell with a flavivirus NS5A peptide or polypeptide; and a method for inhibiting apoptosis in a T cell comprising contacting said T cell with a flavivirus NS5A peptide or polypeptide.

The terms "mimic, mimetic or peptidomimetic" are used interchangeably herein to refer to a peptide derivative comprising a portion, segment, or domain of the NS5A protein, alone or in combination with another molecule, which will produce a biological effect, namely the effect of modulating HIV replication, CD4 expression and/or immune response in a subject. More specifically, a peptidomimetic is a compound containing non-peptidic structural elements capable of mimicking or antagonizing (meaning neutralizing or counteracting) the biological action(s) of a natural parent peptide. Particularly useful for the present invention is a peptidomimetic incorporating the portion of NS5A mediating activity, such as modulating HIV or CD4 expression. Likewise, a NS5A agonist is a compound capable of interacting and modulating the activity of cellular components and/or downstream effectors and modulating HIV or CD4 expression in a subject.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are cited, it is understood that the steps are not required to be performed in the particular order recited unless one of skill in the art is not be able to practice the method in a different order.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 3A-3C. Expression of full-length NS5A in CD4+ Jurkat cells. The complete NS5A coding region was ligated into a pTRE2 vector. Stop codons were placed at the 3' end of the NS5A coding sequences, and these were followed by the EMC IRES directing translation of GFP (FIG. 3A). Jurkat cells were transfected, and after incubation in hygromycin, clonal cell lines were selected that stably expressed GFP (FIG. 3B). These cell lines were then tested for expression of NS5A by immunoblot (FIG. 3C). NS5A expression was diminished by growing the cells in doxycycline (Xiang et al. 2006).

FIG. 7. Chemokine-related gene expression in NS5A expressing Jurkat cells compared to vector control cells. Thirteen genes were significantly down-regulated, and 3 upregulated. Relevant genes are shown.

FIG. 12. Th1,2,3 cytokine-related gene expression in NS5A expressing Jurkat cells compared to vector control cells. Nineteen genes were significantly down-regulated (including IL-4, IL-10, IL-13 and ICOS), and 10 genes were upregulated. Genes of interest are shown. IL-2 expression was not detected in NS5A or control Jurkat cells.

FIG. 13. Apoptosis-related gene expression in NS5A expressing Jurkat cells compared to vector control cells. Six genes were significantly down-regulated and 9 genes were upregulated. Relevant genes are shown.

FIG. 16. Flavivirus NS5A proteins expressed in Jurkat cells have variable effects on HIV replication.

FIG. 17. Amino acid sequence alignment of GBV-C and HCV NS5A peptides that inhibit HIV replication. Sequences and identifiers are as follows: VDGIPVSWDADARAPA (SEQ ID NO: 10); VDGIPVSWEADARAPA (SEQ ID NO: 15); LDGVRLHRFAPPCKPLLREEV (SEQ ID NO: 16); VDGVRLHRYAPACRPLLREEV (SEQ ID NO: 17); VDGVQIHRFAPIPKPFFRDEV (SEQ ID NO: 18); VDGVRLHRYAPPCKPLLREEI (SEQ ID NO: 19).

(FIG. 22A) Infection of cells with YFV (vaccine strain 17D) prior to HIV decreased production of HIV gp120/160 as detected by immunoblot. The YFV multiplicity of infection (MOI) is shown, and HIV NIH AIDS (Reference Reagent program catalog #1073) was used to infect cells as described in FIG. 21. Negative control cells (NC) infected only with HIV are shown. (FIG. 22B) Production of HIV p24 antigen as a marker of HIV replication.

(FIG. 23A) Effect of HIV and YFV timing on HIV replication. (FIG. 23B) Dose-related inhibition of HIV by YFV.

FIGS. 24A-B. (FIG. 24A) YFV infection of primary human CD4+ T cells inhibits replication of a CXCR4-tropic HIV isolate. Primary human T cells enriched for CD4+ cells (>95% CD4+) were grown in media containing PHA and IL-2 as previously described (Xiang et al., 2004). Cells were infected with YFV (vaccine strain 17D; or negative control preparation) for 24 hrs prior to HIV infection (CXCR4-tropic, isolate 1073) as described in FIG. 21. HIV replication (measured by p24 antigen release into culture supernatant fluids was completely abrogated in YFV infected cells. (FIG. 24B) YFV infection of primary human CD4+ T cells inhibits replication of a CCR5-tropic HIV isolate. Primary human T cells enriched for CD4+ cells (>95% CD4+) were grown in media containing PHA and IL-2 as previously described (Xiang et al., 2004). Cells were infected with YFV (vaccine strain 17D; or negative control preparation) for 24 hrs prior to HIV infection (CXCR4-tropic, isolate 1741) as described in FIG. 21. HIV replication (measured by p24 antigen release into culture supernatant fluids) was completely abrogated in YFV infected cells.

FIG. 25. Summary of GBV-C NS5A proteins stably expressed in Jurkat-Tet-off cells. Boxes represent the amino acid region of GBV-C NS5A expressed in cloned Jurkat cell lines. Full length NS5A is 414 amino acids in length (1-414). The 126 frame-shift 237 contains GBV-C NS5A sequences that encode this region in the NS5A protein; however, a plus 1 frame shift was introduced so that the cells encode 26 missense amino acids. The amino acid sequence is shown for the 16mer peptide (152-167) and mutant peptides. Shaded boxes indicate cell lines in which HIV replication was inhibited compared to vector controls. Hatched boxes represent cell lines that inhibited HIV replication compared to controls, but significantly less than full-length NS5A. Cell lines noted by "*" were described previously. Sequences and identifiers are as follows: VDGIPVSWDADARAPA (SEQ ID NO: 10); DVIRAGPAWDSVAPAD (SEQ ID NO: 20); VDGIPVAWDADARAPA (SEQ ID NO: 21); VDGIPVGWDADARAPA (SEQ ID NO: 22); VDGIPVEWDADARAPA (SEQ ID NO: 23); VDGIPVSWDADARA (SEQ ID NO: 14).

FIG. 26. HIV growth characteristics in selected Jurkat cell lines expressing the GBV-C NSSA sequences. HIV replication in selected cell lines expressing various GBV-C NS5A peptides summarized in FIG. 25 was assessed by monitoring HIV p24 antigen release into culture supernatants. FS=the 126 frame-shift 237 construct. HIV replication curves notated by "*" had significantly greater HIV p24 antigen (area under the curve, see methods) than the four cell lines that included NS5A amino acids 152-165 ($P<0.01$).

FIGS. 27A-C. Mutational analysis of GBV-C 152-167 NSSA peptide. Clonal cell lines stably transfected with NS5A peptides were selected by hygromycin resistance and clonal lines established that expressed GFP (FIG. 27A). Peptide constructs included the native NS5A protein (amino acids 152-167), the same amino acids scrambled (152-167scr), or peptides in which the serine (position 158) was replaced with alanine (S158A), glycine (S158G) or glutamic acid (S158E). HIV replication in these cell lines was compared to that in vector control cells (VC) or cells containing the frame-shift GBV-C sequences (FS) (FIG. 27B). The S158E cell line had significantly less HIV replication than all other cell lines (*; $P<0.01$ vs. all other cell lines). The S158A and S158G cell lines had significantly less HIV replication than FS and VC (†; $P=0.041$), but significantly more HIV replication than the S158E cells (†; $P=0.014$). The HIV inhibition was specific for HIV, as mumps virus titers released from Jurkat cells expressing full-length GBV-C NS5A (1-414) and the 152-181 NS5A peptide were not inhibited compared to the VC or parent Jurkat cells (FIG. 27C; *$p=0.029$).

FIG. 28. GBV-C NS5A peptides downregulate CXCR4 expression. Cells expressing the S158E peptide had significantly less CXCR4 expressed than did the S158A, S158G, and 152-167scr cell lines (A). Background fluorescence is shown, and the mean fluorescent intensity values of CXCR4 detection are shown in parentheses.

FIGS. 29A-B. GBV-C NS5A peptides increase the release of stromal derived factor 1 (SDF-1). SDF-1 release into culture supernatants was significantly greater in cell lines expressing GBV-C NS5A peptides 152-165, 152-167 and 152-181 compared to the vector control (VC) or frame shift (FS) cell lines (*$p<0.01$ for all; FIG. 29A). Jurkat cells expressing full-length NS5A (1-414), the 152-167 peptide and the S158E mutant peptide also induced significantly more SDF-1 than did cells expressing VC, FS or the S158A and S158G peptides (FIG. 29B; *$p<0.02$ for all).

FIGS. 30A-B. GBV-C NS5A synthetic peptides inhibit HIV replication. Addition of a synthetic peptide representing GBV-C NS5A amino acids 152-191 (P1) to Jurkat cells 1 hour before HIV infection resulted in a dose-dependent inhibition of HIV replication (concentration of peptide=10, 25, or 50 μg/ml; FIG. 30A). By comparison, overlapping peptides including GBV-C NS5A amino acids 172 to 211 (P2) or amino acids 197 to 236 (P3) did not inhibit HIV replication at 50 μg/mL nor did a peptide containing amino acids from a region in the GBV-C envelope glycoprotein E2 (E2). All HIV replication was compared to cells incubated with no peptide (NP). Addition of peptide 1 (amino acids 152-191) to cells 24 hrs prior to HIV infection [(1) HIV] resulted in inhibition of HIV on day 4 († $p<0.05$; FIG. 30B). In cells in which peptide was not included after HIV infection (−P), HIV inhibition was lost on day 5. When HIV and the peptides were added to cells simultaneously (HIV+P), inhibition was not observed on day 4; however, when the peptide was included in the media (+P), HIV replication was inhibited by day 5 (*$p<0.05$ compared to the NP control).

FIGS. 31A-C. Dose dependent inhibition of HIV replication by the S158E mutant. MT-2 cells were incubated with three concentrations (10, 25, and 50 μg/ml) of synthetic peptides containing GBV-C S158E (FIG. 31A) or 152-167scr (FIG. 31B) amino acid sequences in which an FITC labeled N-terminal Tat-protein transduction domain was included. Cells were washed one hour later and FITC was monitored by flow cytometry. Cells were infected with HIV 24 hrs after incubation, and dose related inhibition of HIV replication was observed for the S158E peptide, but not the 152-167scr peptide compared to the no peptide control (NP). *HIV p24 antigen area under the curve was less than controls ($p<0.01$).

DESCRIPTION OF ILLUSTRATIVE EMBODIMENTS

Anti-retroviral medications suppress viral replication in HIV disease, yet they have failed to eradicate the virus from the body due to the multi-faceted nature of HIV infection, as well as the complexities of the immune system. Methods are being developed that both prevent infection and boost the immune system to keep it functioning at a level where it can assist in fighting HIV infection.

The present inventors have previously reported on methods and compositions for therapeutic and/or prophylactic treatment of HIV infection, including GBV-C envelope proteins, in particular GBV-C envelope protein E2 (E2). More specifically, the inventors have shown that HIV-infected subjects that are co-infected with GB virus C (GBV-C) typically have reduced mortality and slower progression to AIDS as compared to HIV-infected subjects without GBV-C co-infection (PCT/US2004/017706). Infection of peripheral blood mononuclear cells (PBMCs) with GBV-C and HIV results in inhibition of HIV-1 replication. GBV-C infection typically inhibits HIV by inducing β-chemokines and reducing expression of the HIV co-receptor CCR5, explaining part of the beneficial clinical findings of GBV-C on HIV disease progression. The inventors also described a therapeutic use for antibodies and/or binding agents that bind GBV-C proteins (e.g., envelope proteins), in particular, the E2 protein, and similar antigens used for producing these antibodies or binding agents (PCT/US03/33925).

Figure 1:
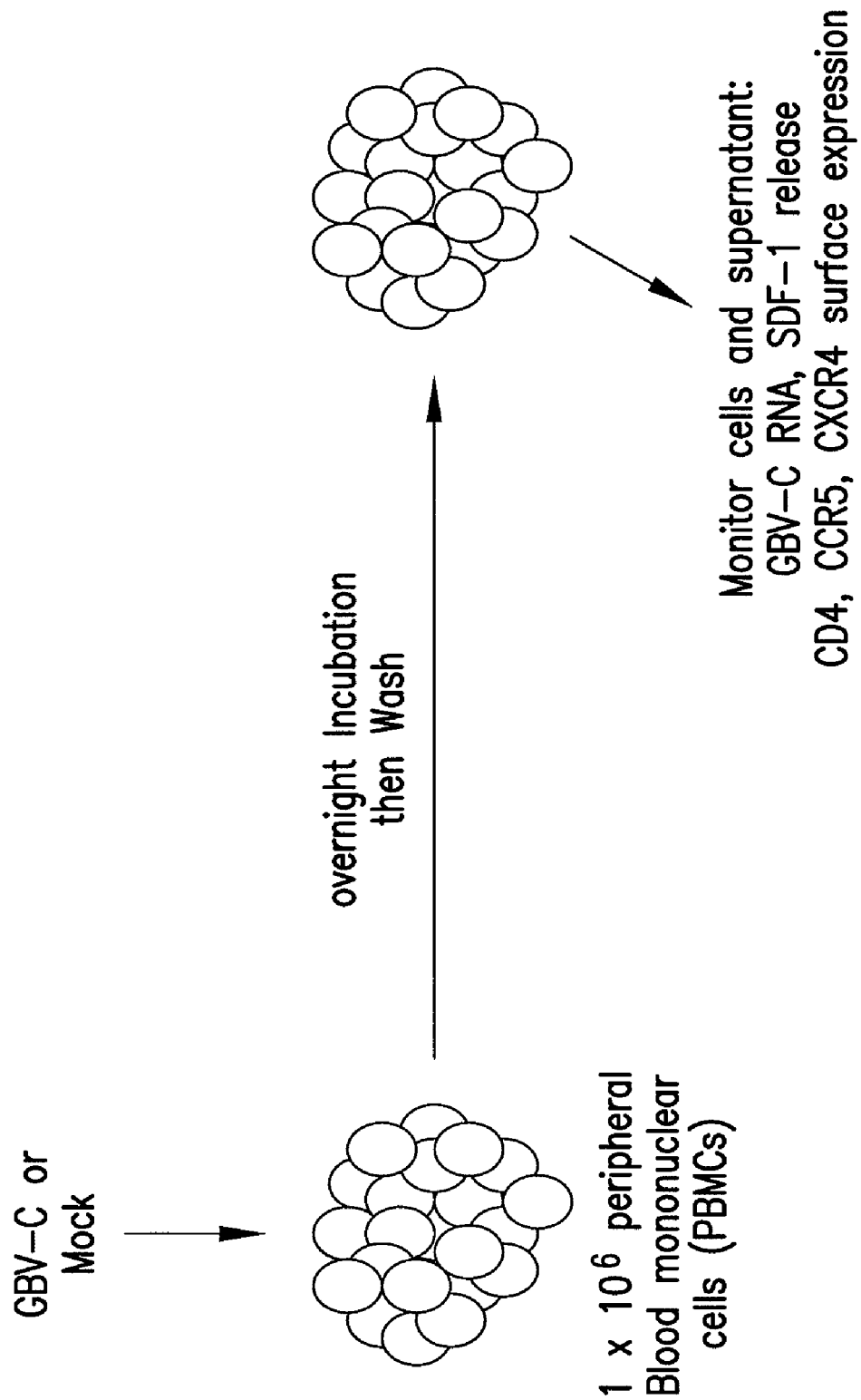
FIG. 1. GBV-C in vitro replication model.

The inventors now demonstrate a unique role for the NS5A protein of GBV-C, as well as NS5A's from other flaviviruses, in the inhibition of HIV replication, particularly peptides related to amino acids 152-167 of GBV-C and similar NS5A regions of other flaviviruses. Various aspects of the invention are described below.

I. FLAVIVIRUSES

A. Family

With a total of 69 pathogens in its ranks, Flaviviridae contains a myriad of viruses that cause disease in humans. Foremost among these is Yellow Fever Virus from which the family begets its name (flavus in Latin means "yellow"). Flaviviruses have been subdivided by the ICTV into three genera: Flavivirus, Pestivirus and Hepacivirus.

The Flavivirus genus contains several dangerous viruses including yellow fever virus, dengue fever virus, and Japanese encephalitis (JE) virus. The Pestivirus genus is home to the three serotypes of bovine viral diarrhea, but no known human pathogens. The genus Hepacivirus consists of hepatitis C virus and its relatives.

Flavivirus genomes consist of a monopartite (i.e., one piece of) linear, single-stranded, positive sense RNA. Because the RNA is positive sense, the nucleic acid itself is capable of instigating an infection in the appropriate host cells. The total genome can range from 10 to 11 kilobase pairs. The genome 3' terminus is not polyadenylated. The 5' end has a methylated nucleotide cap (allows for translation) or a genome-linked protein (VPg). Pestivirus genomes are reported to be 12.5 kb in length. Like the Flavivirus genus, no poly-A tail exists on the 3' end of the RNA, however, Pestivirus genus members lack a 5' cap. In both genera, structural genes are found towards the 5' end of the RNA. Both the Pestivirus and Hepacivirus genera contain internal ribosomal entry sites (IRES) that provide a site of translation initiation for host ribosomes. This is in contrast to the Flavivirus genus that uses the technique of ribosomal scanning to commence protein synthesis.

Under the EM, virions appear roughly as spheres, 40-65 nm in diameter. What can be seen under the microscope is the virus's lipid envelope, which it obtains from host cells during egress (leaving the cell). Underneath the envelope can be found an icosahedral capsid coat approximately 25-30 nm in diameter.

All members of the Flavivirus genus are transmitted by arthropods (i.e., mosquitoes and ticks) while Hepatitis C is spread parenterally (i.e., through contaminated bodily fluids). A key feature for viral transmission in Flaviviruses is that they are capable of reproducing in their vector. Without the ability to replicate in the vector, they would not remain viable to be passed from one host to the next.

B. GBV-C

Like other members of the Flaviviridae, GBV-C is a positive-strand RNA virus that encodes a single long open reading frame (Leary et al., 1996). GBV-C does not cause acute or chronic hepatitis, yet it is the family member most closely related to HCV, the cause of hepatitis C. Sequences of GBV-C have been previously reported, for example in U.S. Pat. No. 5,874,563, which is specifically incorporated by reference. In particular, an infectious GBV-C clone has been described in the PCT application WO 01/77157, which is incorporated herein by reference.

The GBV-C polyprotein is predicted to be cleaved into two envelope proteins (E1 and E2, referred to collectively as GBV-C envelope protein), an RNA helicase, a trypsin-like serine protease, and an RNA-dependent RNA polymerase. A major difference between GBV-C and HCV is in the amino terminus of the polyprotein. In many isolates, this region is truncated, and no core (or nucleocapsid) protein is present (Simons et al., 1995; Xiang et al., 1999). In vitro translation experiments suggest that the AUG immediately upstream of the putative E1 protein is preferentially used to initiate translation, although there may be as many as four AUG's in frame with the polyprotein upstream of this AUG (Simons et al., 1996).

The site of GBV-C replication has not been clearly identified, but it appears that replication in the hepatocyte, if it occurs, is not the primary source of virus in infected individuals (Laskus et al., 1998; Pessoa et al., 1998; Seipp et al., 1999). Recently, there were reports that human peripheral blood mononuclear cells (PBMC's) and interferon-resistant Daudi cells are permissive for GBV-C replication (Fogeda et al., 1999; Shimizu, 1999). In addition, transient replication of GBV-C was described in MT-2 cells (a human T-cell line), and PH5CH (a human hepatocyte line immortalized with simian virus 40 large T antigen) (Seipp et al., 1999).

C. Other Flavivirus

Other Flaviviruses are structurally similar to GBV-C and can be used in accordance with the present invention. These viruses include DEN1-4, YFV, TBEV, WNV, CSFV, BVDV, GBV-A, GBV-B, HGV, HCV2a, HCV3a, HCV2b, HCV1a, HCV1c and HCV1b.

II. GBV-C POLYPEPTIDES

In certain aspects, the invention is directed to the NS5A polypeptide of a flavivirus, e.g., GBV-C virus, or a peptide or polypeptide derived there from. SEQ ID NO:2 shows the translated product of SEQ ID NO:1 (cDNA of GBV-C). It is contemplated that the compositions and methods disclosed herein may be utilized to express all or part of SEQ ID NO:2 and derivatives thereof, particularly the NS5A region as depicted in SEQ ID NO:9. In certain embodiments, compositions of the invention may include the nucleic acids encoding the peptides as set forth in SEQ ID NO:1, 3, or 9. Determination of which protein or DNA molecules inhibit HIV may be achieved using functional assays measuring HIV replication and infectivity, which are familiar to those of skill in the art. The structure of the various polypeptides or peptides can be modeled or resolved by computer modeling, NMR, or x-ray crystallography. Such structures may be used to engineer derivatives of the various NS5A protein.

Exemplary accession nos. for other NS5A's are as follows and are incorporated herein by reference in there entirety:

| Virus | Accession No. |
|---|---|
| West Nile | DQ318019 |
| Yellow fever | NC002031 |
|  | AY603338 |
| BVDV | AF502399 |
| Dengue 1-4 | M878512 |
| Dengue 1-4 | AY66269 |
| HCV 1a | AF011753 |
| 1b | AF333324 |
| 1c | D14853 |
| 2a | D00944 |
| M14931 2b | D10988 |
| M20558 3a | AF046866 |

A. Variants of GBV-C NS5A Polypeptides

Embodiments of the invention include various GBV-C NS5A polypeptides, peptides, and derivatives thereof. Amino acid sequence variants of a polypeptide can be substitutional, insertional, or deletion variants. Deletion variants lack one or more residues of the native protein that are not essential for function or immunogenic activity. Insertional mutants typically involve the addition of material at a non-terminal point in the polypeptide. This may include the insertion of an immunoreactive epitope or simply a single residue. Terminal additions, called fusion proteins, are discussed below.

In determining which region(s) of NS5A were required for HIV inhibition, the inventors created a series of cell lines expressing GBV-C NS5A deletion mutants. All cell lines demonstrated GFP expression, linkage of NS5A sequence with GFP by cellular DNA PCR, and when antibodies available, by NS5A western blotting. HIV Infection in these cell lines demonstrated that the HIV inhibitory region requires only amino acids 152 and 167 (VDGIPVSWDADARAPA (SEQ ID NO:10)). This region is highly conserved between GBV-C isolates from all 5 genotypes (only variant amino acid is E161D). Although full-length NS5A induced SDF-1 release from cells, the deletion mutant 152-167 does not, thus SDF-1 release does not account for all of the HIV inhibitory effect. These data indicate that the serine is critical for the HIV inhibitory effect, and that substitution of a glutamic acid (phosphomimetic substitution) maintains it's phenotype. This suggests that phosphorylation of the serine may be required for the HIV inhibitory effect.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of GBV-C NS5A polypeptides, for example SEQ ID NO:2 or SEQ ID NO:10, provided the biological activity of the protein or peptide is maintained.

The term "functionally equivalent codon" is used herein to refer to codons that encode the same amino acid, such as the six codons for arginine or serine, and also refers to codons that encode biologically equivalent amino acids (see Table 1, below).

Certain embodiments of the invention include various peptides or polypeptides of the NS5A protein. For example, all or part of a GBV-C NS5A protein as set forth in SEQ ID NO:9 or 10 may be used in various embodiments of the invention. In certain embodiments, a fragment of the NS5A protein may comprise, but is not limited to about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 415, and any range derivable therein.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of an NS5A polypeptide or peptide to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA or RNA coding sequence, and nevertheless produce a protein with like properties. It is thus contemplated by the inventors that various changes may be made in the DNA or RNA sequences of genes or coding regions without appreciable loss of their biological utility or activity, as discussed herein. Table 1 shows the codons that encode particular amino acids.

TABLE 1

CODON TABLE

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

It is understood that an amino acid substituted for another having a similar hydrophilicity value still produces a biologically equivalent and immunologically equivalent protein.

In certain embodiments, an NS5A polypeptide may be a fusion protein. Fusion proteins may alter the characteristics of a given polypeptide, such cellular uptake and/or permeability, antigenicity or purification characteristics. A fusion protein is a specialized type of insertional variant. This molecule generally has all or a substantial portion of the native molecule or peptide, linked at the N- or C-terminus, to all or a portion of a second polypeptide. For example, fusions typically employ leader or targeting sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals, or transmembrane regions.

B. Peptides

In this application, the products of the present invention are referred to by various terms, including "analogs," "mimetics," "peptidomimetics," and "derivatives." These terms are used interchangeably and denote equivalent compounds. Mimetics of the present invention comprise a structure which comprises a sequence or mimics the structure of a sequence set forth as SEQ ID NO:9, and thus may comprise additional elements such as R-group substituents and a linker selected from the possibilities set forth in the instant invention.

As defined by the present invention, biological activity refers to the biological activity of NS5A and its segments. Aspects of biological activity include, but are not limited to, modulation of HIV, modulation of immune response, and modulation of CD4 expression, and modulation of T cell activity, along with other activities recognized by those of skill in the art.

Mimetics of the invention may include peptide derivatives or peptide analogs and their derivatives, such as C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal residue is replaced with a phenethylamide analogue, glycosylated peptide derivatives, polyethylene glycol modified derivatives, or biotinylated derivatives. Peptide analogs of the invention include pharmaceutically acceptable salts of an analog.

In one aspect of the invention, the peptide analogs of the invention may be coupled directly or indirectly to at least one modifying group. In some aspects of the invention, the term "modifying group" is intended to include structures that are directly attached to the peptidic structure (e.g., by covalent bonding or covalent coupling), as well as those that are indirectly attached to the peptidic structure (e.g., by a stable non-covalent bond association or by covalent coupling through a linker to additional amino acid residues). In other aspects of the invention the term "modifying group" may also refer to mimetics, analogues or derivatives thereof. Alternatively, the modifying group can be coupled to a side chain of at least one amino acid residue of a NS5A peptide, or a peptidic or a peptidomimetic (e.g., through the epsilon amino group of a lysyl residue(s); through the carboxyl group of an aspartic acid residue(s) or a glutamic acid residue(s); through a hydroxy group of a tyrosyl residue(s), a serine residue(s) or a threonine residue(s); or any other suitable reactive group on an amino acid side chain). In other aspects, modifying groups covalently coupled to the peptidic structure can be attached by means and using methods well known in the art for linking chemical structures, including, for example, amide, alkylamino, sulfide, carbamate or urea bonds.

In some embodiments, the modifying group may comprise a cyclic, heterocyclic or polycyclic group. The term "cyclic group," as used herein, includes cyclic saturated or unsaturated (i.e., aromatic) group having from 3 to 10; from 4 to 8; or 5, 6, or 7 carbon atoms. Exemplary non-aromatic cyclic groups include cyclopropyl, cyclobutyl, cyclopentyl, cyclohexyl, and cyclooctyl. The term "heterocyclic group" includes optionally substituted, saturated or unsaturated, three- to eight-membered cyclic structures in which one or more skeletal atoms is oxygen, nitrogen, sulfur, or combinations thereof. Cyclic groups may be unsubstituted or substituted at one or more ring positions. A cyclic group may for example be substituted with halogens, alkyls, cycloalkyls, alkenyls, alkynyls, aryls, arylalkyls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN. The cyclic group may also be linked to a substituent, such as halogens, alkyls, cycloalkyls, alkenyls, alkynyls, aryls, arylalkyls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, or —CN, by means of a saturated or unsaturated chain of 1, 2, 3, 4, 5, 6, 7, 8, or more carbon atoms; additionally one or more of the carbon atoms may be replaced with an oxygen, nitrogen, or sulfur atom. Other means of linking these groups are also possible.

In one embodiment of the invention, peptides and peptide analogs are designed by replacing all or part of a structural domain with a linker or a compound that mimic such structure. In a different embodiment, all or a portion of the amino-terminal domain and all or a portion of the carboxy-terminal domain of a peptide or peptide analog are connected with a linker. In another embodiment, the peptide and peptide analogs are designed so that there are cyclized by covalent modification between residues of the peptide.

Modifying groups may also include groups comprising biochemical labels or structures, such as biotin, fluorescent-label-containing groups, light scattering or plasmon resonant particle, a diethylene-triaminepentaacetyl group, a (O)-menthoxyacetyl group, a N-acetylneuraminyl group, a cholyl structure or an iminobiotinyl group. A peptide analog or peptide mimetic compound may be modified at its carboxy terminus with a cholyl group according to methods known in the art. Cholyl derivatives and analogs may also be used as modifying groups. For example, a preferred cholyl derivative is Aic (3-(O-aminoethyl-iso)-cholyl), which has a free amino group that can be used to further modify a peptide mimetic compound. A modifying group may be a "biotinyl structure," which includes biotinyl groups and analogues and derivatives thereof (such as a 2-iminobiotinyl group). In another embodiment, the modifying group may comprise a fluorescent-label group, e.g., a fluorescein-containing group, such as a group derived from reacting an peptidic structure with 5-(and 6-)-carboxyfluorescein, succinimidyl ester or fluorescein isothiocyanate. Peptide analogs may also be modified by attaching other fluorescent labels including rhodamine, dichlorotriazinylamine fluorescein, dansyl chloride or phycoerythrin and energy transfer fluorescent dyes or fluorescent ion-indicators. In various other embodiments, the modifying group(s) may comprise an N-acetylneurarninyl group, a trans 4-cotininecarboxyl group, a 2-imino-1-imidazolidineacetyl group, an (S)-(−)-indoline-2-carboxyl group, a (−)-menthoxyacetyl group, a 2-norbornaneacetyl group, a γ-oxo-5-acenaphthenebutyryl, a (−)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group. In other embodiments, light scattering groups, magnetic groups, nanogold, other proteins, a solid matrix, radiolabels, or carbohydrates may be attached.

In still other aspects, the modifying group may be an oligomer, for example, polyethylene glycol, an oligonucleotide, a polypeptide (which may or may not be derived from GBV-C peptide).

A peptide analog compound of the invention may be further modified to alter the specific properties of the compound while retaining the desired functionality of the compound. For example, in one embodiment, the compound may be modified to alter a pharmacokinetic property of the compound, such as in vivo stability, solubility, bioavailability or half-life. The compound may be modified to label the compound with a detectable substance. The compound may be modified to couple the compound to an additional therapeutic moiety. To further chemically modify the compound, such as to alter its pharmacokinetic properties, reactive groups can be derivatized. For example, when the modifying group is attached to the amino-terminal end of a peptide, the carboxy-terminal end of the compound may be further modified. Potential C-terminal modifications include those that reduce the ability of the compound to act as a substrate for carboxypeptidases. Examples of C-terminal modifiers include an amide group, an ethylamide group and various non-natural amino acids, such as D-amino acids, β-alanine, C-terminal decarboxylation, and a C-terminal alcohol.

Peptide and peptide analogs of the invention may be modified by the addition of polyethylene glycol (PEG). PEG modification may lead to improved circulation time, improved solubility, improved resistance to proteolysis, reduced antigenicity and immunogenicity, improved bioavailability, reduced toxicity, improved stability, and easier formulation.

In an alternative chemical modification, a peptide analog compound of the invention may be prepared in a "prodrug" form, wherein the compound itself does not act as a peptide analog agonist, but rather is capable of being transformed, upon metabolism in vivo, into a peptide analog agonist or antagonist compound.

Mimetics of the invention may be prepared by standard techniques known in the art. A peptide or polypeptide component of an analog may comprise, at least in part, a peptide synthesized using standard techniques (such as those described by Clark-Lewis et al., 1994). Automated peptide synthesizers are commercially available (e.g., Advanced ChemTech Model 396; Milligen/Biosearch 9600, Applied Biosystems/Pioneer). Peptides and polypeptides may be assayed for activity in accordance with methods exemplified herein. Peptides and polypeptides may be purified by HPLC and analyzed by mass spectrometry.

The analogs of the invention include peptide or polypeptide sequences wherein one or more of the amino acids have been replaced by a conservative amino acid substitution. The term "conservative amino acid substitution" refers to a peptide chain in which one of the amino acid residues is replaced with an amino acid residue having a side chain with similar properties. Families of amino acid residues having side chains with similar properties are well known in the art. These families include amino acids with acidic side chains (e.g., aspartic acid, glutamic acid), basic side chains (e.g., lysine, arginine, histidine), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, an amino acid residue in a chemokine is replaced with another amino acid residue from the same side chain family.

C. In Vitro Production of NS5A Polypeptides or Peptides

Various types of expression vectors are known in the art that can be used for the production of protein products. Following transfection with a expression vector, a cell in culture, e.g., a primary mammalian cell, a recombinant product may be prepared in various ways. A host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented (for exemplary methods see Freshney, 1992).

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large-scale production of cells and cell products. However, suspension cultured cells have limitations, such as tumorigenic potential and lower protein production than adherent cells.

In further aspects of the invention, other protein production methods known in the art may be used, including but not limited to prokaryotic, yeast, and other eukaryotic hosts such as insect cells and the like.

Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to 16 to about 35 to 50 amino acids, which correspond to the selected regions described herein, can be readily synthesized and then screened in screening assays designed to identify reactive peptides.

D. Protein Purification

It may be desirable to purify NS5A polypeptides and peptides, or variants and derivatives thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, hydrophobic interaction chromatography, exclusion chromatography; polyacrylamide gel electrophoresis; isoelectric focusing. A particularly efficient method of purifying peptides is fast protein liquid chromatography (FPLC).

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme.

III. FLAVIVIRUS POLYNUCLEOTIDES

Certain embodiments of the invention include Flavivirus NS5A polynucleotides or nucleic acid molecules and fragments thereof. The polynucleotides of the invention may be isolated and purified from Flavivirus or cells infected or transfected with Flavivirus polynucleotides. The term isolated indicating they are free or substantially free from total viral or cellular genomic RNA or DNA, and proteins. It is contemplated that an isolated and purified Flavivirus nucleic acid molecule may take the form of RNA or DNA. A Flavivirus nucleic acid molecule refers to an RNA or DNA molecule that is capable of yielding all or part of a Flavivirus NS5A from a transfected cell, particularly a peptide such as that provided in SEQ ID NO:10 or a related Flavivirus peptide.

When the present application refers to the function or activity of an infectious Flavivirus that is encoded by a Flavivirus polynucleotide, it is meant that the polynucleotide encodes a molecule that has the ability to propagate an infectious Flavivirus virus particle from a cell. It is contemplated that a Flavivirus polynucleotide may refer to a Flavivirus RNA transcript that is able to propagate an infectious Flavivirus virus particle after introduction to a cell or to a Flavivirus expression construct, clone, or vector composed of double-stranded DNA or DNA/RNA hybrid that is similarly capable, or a double-stranded DNA that is similarly capable following in vitro transcription.

The term "cDNA" is intended to refer to DNA prepared using RNA as a template. The advantage of using a cDNA, as opposed to genomic RNA or an RNA transcript is stability and the ability to manipulate the sequence using recombinant DNA technology (see Maniatis, 1990; Ausubel, 1996). There may be times when the full or partial genomic sequence is preferred.

It also is contemplated that a given Flavivirus may be represented by natural variants or strains that have slightly different nucleic acid sequences but, nonetheless, encode the same viral polypeptides (see Table 1 above). Consequently, the present invention also encompasses derivatives of Flavivirus with minimal amino acid changes in its viral proteins, but that possesses the same activities.

The term "gene" is used for simplicity to refer to the nucleic acid giving rise to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding Flavivirus may contain a contiguous nucleic acid sequence encoding one or more Flavivirus genes and regulatory regions and be of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 10,000 or more nucleotides, nucleosides, or base pairs. Such sequences may be identical or complementary to all or part of SEQ ID NO:1.

In particular embodiments, the invention concerns isolated nucleic acid segments and recombinant vectors incorporating DNA sequences that encode Flavivirus NS5A polypeptides or peptides. Such vectors used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

In a non-limiting example, one or more nucleic acid constructs may be prepared that include a contiguous stretch of nucleotides identical to or complementary to a Flavivirus genome, particularly a nucleic acid sequence encoding the protein of SEQ ID NO:9 or a peptide having a sequence similar to SEQ ID NO:10. A nucleic acid construct may be about 50, 60, 70, 80, 90, 100, 200, 300, 400, 500, 600, 700, 800, 900, 1,000, 2,000, 3,000, 4,000, 5,000, 6,000, 7,000, 8,000, 9,000, and 9,400, nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.

The nucleic acid segments used in the present invention encompass biologically functional and/or immunogenically equivalent Flavivirus NS5A proteins and peptides. Such sequences may arise as a consequence of codon redundancy and functional equivalency that are known to occur naturally within nucleic acid sequences and the proteins thus encoded. Alternatively, functionally and immunologically equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein.

A. Vectors Encoding Flavivirus

The present invention encompasses the use of vectors to encode for all or part of one or more Flavivirus NS5A polypeptides, including an infectious Flavivirus. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). In particular embodiments, gene therapy or immunization vectors are contemplated. One of skill in the art would be well equipped to construct a vector through standard recombinant techniques, which are described in Maniatis et al. (1990) and Ausubel et al. (1996), both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra. It is contemplated that an infectious Flavivirus particle of the present invention may arise from a vector containing Flavivirus sequence or RNA encoding Flavivirus sequence into a cell. Either of these, or any other nucleic acid molecules of the present invention may be constructed with any of the following nucleic acid control sequences. Thus, the full-length RNA transcript may contain the benefit of recombinant DNA technology such that it contains exogenous control sequences or genes.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" means that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202 and U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (2001), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or exogenous, i.e., from a different source the Flavivirus sequence. In some examples, a prokaryotic promoter is employed for use with in vitro transcription of a desired sequence. Prokaryotic promoters for use with many commercially available systems include T7, T3, and Sp6.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al, 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |

TABLE 2-continued

Promoter and/or Enhancer

| Promoter/Enhancer | References |
|---|---|
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), DIA dopamine receptor gene (Lee, et al., 1997), insulin-like growth factor II (Wu et al., 1997), human platelet endothelial cell adhesion molecule-1 (Almendro et al., 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome-scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see Carbonelli et al., 1999, Levenson et al., 1998, and Cocea, 1997, incorporated herein by reference). "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

5. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively, an autonomously replicating sequence (ARS) can be employed if the host cell is yeast.

7. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials. An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

C. Expression Systems

Numerous expression systems exist that comprise at least all or part of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986 and 4,879,236, both herein incorporated by reference, and which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

D. Introduction of Nucleic Acids into Cells

In certain embodiments, a nucleic acid may be introduce into a cell in vitro for production of polypeptides or in vivo for immunization purposes. There are a number of ways in which nucleic acid molecules such as expression vectors may be introduced into cells. In certain embodiments of the invention, the expression vector comprises a Flavivirus infectious particle or engineered vector derived from a Flavivirus genome. In other embodiments, an expression vector known to one of skill in the art may be used to express a segment of a Flavivirus nucleic, which may be translated into a Flavivirus polypeptide or peptide. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986).

"Viral expression vector" is meant to include those vectors containing sequences of that virus sufficient to (a) support packaging of the vector and (b) to express a polynucleotide that has been cloned therein. In this context, expression may require that the gene product be synthesized. A number of such viral vectors have already been thoroughly researched, including adenovirus, adeno-associated viruses, retroviruses, herpesviruses, and vaccinia viruses.

Delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), liposome (Ghosh and Bachhawat, 1991; Kaneda et al., 1989) and receptor-mediated transfection (Wu and Wu, 1987; Wu and Wu, 1988). Some of these techniques may be successfully adapted for in vivo or ex vivo use.

In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro, but it may be applied to in vivo use as well.

IV. ANTI-HIV THERAPIES

In certain embodiments, therapeutic methods will include administering to a patient or subject a composition comprising an antigen or an antibody derived from a Flavivirus NS5A peptide or polypeptide, such as human or humanized animal derived antibodies. In various embodiments, the treatment methods of the invention may be used in combination with other anti-HIV treatments, such as Flavivirus infection as a therapeutic or preventative treatment for AIDS. For exemplary compositions and methods see PCT application WO 01/77157, which is incorporated herein by reference.

As a therapeutic measure, a Flavivirus NS5A agent can be used to reduce the severity or progression of AIDS, including the prevention of AIDS in HIV-infected individuals. A reduction in severity or progression of AIDS includes, but is not limited to, prevention of or a reduction in the severity, duration, or discomfort associated with the following conditions: prolonged and unexplained fatigue; swollen glands; prolonged fever; chills; excessive sweating; swollen gums and mouth lesions; sore throat; cough; shortness of breath; constipation; diarrhea; symptoms of well-known opportunistic infections; Kaposi sarcomas; skin rashes or lesions; loss of appetite or weight loss; malaise; headaches; speech impairment; muscle atrophy; memory loss; reduced cognitive functioning; swelling of the joints; joint stiffness or pain; cold intolerance; pain or tenderness in bones; energy level; anxiety, stress, and tension; groin lump; pruritus; genital sores; blurred or decreased vision; diplopia; light sensitivity; pain in chest, sides, back, muscle or stomach; and seizures.

As a preventative measure, a patient may be administered a pharmaceutically acceptable composition comprising a Flavivirus NS5A peptide or polypeptide. This agent may be used in conjunction with infection of CD4+ T cells with Flavivirus or a recombinant version of Flavivirus to inhibit infection of these cells by HIV. Alternatively, treatment with the Flavivirus NS5A compositions of the present invention may effect a combination of preventative and therapeutic treatments insofar as infection of other cells in an HIV-infected subject's body is prevented or attenuated.

Inhibition of AIDS progression may be demonstrated by reduction of detectable HIV in the HIV-infected subject; maintaining a CD4 count above 200 for a longer than average period of time; maintaining a normal T cell count; or maintaining normal p24 antigen. The term "therapeutic benefit" or "therapeutic effect" used throughout this application refers to anything that promotes or enhances the well-being of the subject with respect to the medical treatment of his/her condition, which includes treatment of HIV-infection (before the onset of AIDS), AIDS, as well as treatment of Hepatitis C. A list of nonexhaustive examples of this includes extension of the subject's life by any period of time; decrease or delay in the progression of AIDS (HIV, as described above) or Hepatitis C; decrease in viral load of HIV or HCV; decrease in HIV replication; clearance of HIV or HCV viremia reduced transmission of HCV or HIV; decrease in liver damage or complications; and a decrease in pain to the subject that can be attributed to the subject's condition.

V. IMMUNE MODULATION

T helper cells are a sub-group of lymphocytes that play an important role in establishing and maximizing the capabilities of the immune system. These cells are unusual in that they have no cytotoxic or phagocytic activity; they cannot kill infected host cells or pathogens, and without other immune cells they would usually be considered useless against an infection. T helper cells are involved in activating and directing other immune cells, and are particularly important in the immune system. They are essential in determining B cell antibody class switching, in the activation and growth of cytotoxic T cells, and in maximizing bactericidal activity of phagocytes such as macrophages. It is this diversity in function and their role in influencing other cells that gives T helper cells their name.

Mature Th cells are believed to always express the surface protein CD4. T cells expressing CD4 are also known as CD4+ T cells. CD4+ T cells are generally treated as having a predefined role as helper T cells within the immune system, although there are known rare exceptions. For example, there are sub-groups of suppressor T cells, natural killer T cells, and cytotoxic T cells that are known to express CD4. All of the latter CD4+ T cell groups are not considered T helper cells.

The importance of helper T cells can be seen from HIV, a virus that infects cells that are CD4+ (including helper T cells). Towards the end of an HIV infection the number of functional CD4+ T cells falls, which leads to the symptomatic stage of infection known as the acquired immune deficiency syndrome (AIDS). There are rare disorders, probably genetic in etiology, that result in the absence or dysfunction of CD4+ T cells. These disorders produce similar symptoms, and many of these are fatal (see CD4+ lymphocytopenia). However, in some circumstances the down modulation of CD4 may be beneficial in modulating the immune response, particularly those immune responses that are pathogenic or potentially pathogenic, as well as those responses that accompany tissue, organ, or graft rejection.

In accordance with the present invention, flavivirus NS5A proteins have now been shown to have immune modulatory functions on T cells, particularly CD4 T cells. For example, modulating CD4 expression may be used to also modulate the activity or CD4 and the resultant immune responses associated with T cells expressing CD4. In various embodiments, the polypeptides and peptides of the invention can be used to attenuate, modulated, and/or suppress an immune response in a subject. The particular aspects of modulating T cell function may include one or more of altering CD4 expression, altering chemokine production, and inhibiting apoptosis in the T cell.

Therapeutic formulations provided herein, which include a peptide composition as described, are used to treat or alleviate a symptom associated with an immune-related disorder, such as, for example, an autoimmune disease or an inflammatory disorder. Autoimmune diseases include, for example, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus (Type I diabetes), juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

The compositions of the invention are administered to a subject suffering from an immune-related disorder, such as an autoimmune disease or an inflammatory disorder. A subject suffering from an autoimmune disease or an inflammatory disorder is identified by methods known in the art. For example, subjects suffering from an autoimmune disease such as Crohn's disease, ulcerative colitis or inflammatory bowel disease, are identified using any of a variety of clinical and/or laboratory tests such as, physical examination, radiologic examination, and blood, urine and stool analysis to evaluate immune status. For example, patients suffering from multiple sclerosis are identified, e.g., by using magnetic resonance imaging the presence of central nervous system (CNS) lesions that are disseminated in time and space (i.e., occur in different parts of the CNS at least three months apart). Patients suffering from rheumatoid arthritis are identified using, e.g., blood tests and/or x-ray or other imaging evaluation. Patients suffering from Type I diabetes are identified, e.g., when any three of these tests is positive, followed by a second positive test on a different day: (1) fasting plasma glucose of greater than or equal to 126 mg/dl with symptoms of diabetes; (2) casual plasma glucose (taken at any time of the day) of greater than or equal to 200 mg/dl with the symptoms of diabetes; or (3) oral glucose tolerance test (OGTT) value of greater than or equal to 200 mg/dl measured at a two-hour interval (the OGTT is given over a three-hour time span).

Administration of a peptide or peptide mimetic to a patient suffering from an immune-related disorder such as an autoimmune disease or an inflammatory disorder is considered successful if any of a variety of laboratory or clinical results is achieved. For example, administration of a peptide or peptide mimetic formulation to a patient suffering from an immune-related disorder such as an autoimmune disease or an inflammatory disorder is considered successful if one or more of the symptoms associated with the disorder is alleviated, reduced, inhibited or does not progress to a further, i.e., worse, state. Administration of a composition to a patient suffering from an immune-related disorder such as an autoimmune disease or an inflammatory disorder is considered successful if the disorder, e.g., an autoimmune disorder, enters remission or does not progress to a further, i.e., worse, state.

The compositions provided herein may be administered in a dosage between 0.1 mg/day to 5.0 mg/day to 500 mg/day, or administered in a dosage between 0.5 mg/day to 3.0 mg/day to 300 mg/day. For example, the composition may be administered in a dosage selected from 0.5 mg/day, 0.6 mg/day, 0.7 mg/day, 0.8 mg/day, 0.9 mg/day, 1.0 mg/day, 1.1 mg/day, 1.2 mg/day, 1.3 mg/day, 1.4 mg/day, 1.5 mg/day, 1.6 mg/day, 1.7 mg/day, 1.8 mg/day, 1.9 mg/day, 2.0 mg/day, 2.1 mg/day, 2.2 mg/day, 2.3 mg/day, 2.4 mg/day, 2.5 mg/day, 2.6 mg/day, 2.7 mg/day, 2.8 mg/day, 2.9 mg/day, and 3.0 mg/day.

In another embodiment, these immunosuppressive compositions are administered in combination with any of a variety of known anti-inflammatory and/or immunosuppressive compounds. Suitable anti-inflammatory and/or immunosuppressive compounds for use with the compositions used herein include, but are not limited to, methotrexate, cyclosporin A (including, for example, cyclosporin microemulsion), tacrolimus, corticosteroids and statins.

VI. COMBINATION THERAPIES

Of course it is understood that the method of the present invention, particularly administration of NS5A agents as treatment for an HIV-infected subject, may also be used in combination with the administration of traditional therapies. Alternatively, the compositions of the present invention may be given in combination with treatment or prevention of hepatitis C, such as α-interferon. Some such therapies are described below.

In many clinical situations, it is advisable to use a combination of distinct therapies. Thus, it is envisioned that, in addition to the therapies described herein, one would also wish to provide to the patient more "standard" pharmaceutical anti-retroviral therapies. Examples of standard therapies are provided below.

Combinations may be achieved by administering to a patient a single composition or pharmacological formulation that includes both agents, or by administering to a patient two distinct compositions or formulations, at the same time, wherein one composition may include a Flavivirus NS5A, or expression construct encoding such, and the other includes the standard anti-retroviral therapy. Alternatively, a Flavivirus-based therapeutic may precede or follow the other treatment by intervals ranging from minutes to weeks. In embodiments where the other agent and NS5A are administered separately to the patient, one would generally ensure that a significant period of time did not expire between the time of each delivery, such that the agent and NS5A would still be able to exert an advantageously combined effect on the patient. In such instances, it is contemplated that one would administer to the patient both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6, or 7) to several weeks (1, 2, 3, 4, 5, 6, 7, or 8) lapse between the respective administrations.

It also is conceivable that more than one administration of a NS5A-based therapeutic agent will be desired. Various combinations may be employed, where a NS5A is "A" and the other agent is "B," as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are contemplated as well.

A. AZT

A well known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

B. HAART

New combination drug therapy has shown promising results in the treatment of HIV-infected patients. Treatment with potent anti-HIV drug combinations is referred to as "highly active anti-retroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

In many instances, it will be desirable to have multiple administrations of the inventive compositions and/or a vaccines, usually not exceeding six administrations or vaccinations, more usually not exceeding four vaccinations. In certain embodiments, one or more, usually at least about three administrations or vaccinations may be provided. The administrations or vaccinations will normally be at from two to twelve week intervals, more usually from three to five week intervals. Periodic boosters at intervals of 1-5 years, usually three years, will be desirable to maintain protective levels of the antibodies. The course of the immunization or treatment may be followed by standard antibody assays. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

The manner of application may be varied widely. Any of the conventional methods for administration of an antibody or vaccine are applicable. These are believed to include oral application on a solid physiologically acceptable base or in a physiologically acceptable dispersion, parenterally, by injection or the like. The dosage of the NS5A agent will depend on the route of administration and will vary according to the size of the host.

The NS5A agents and flavivirus nucleic acids of the invention may be formulated into a pharmaceutically acceptable composition, see below, or vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparation of flavivirus NS5A agents as active ingredients is generally well understood in the art by analogy, as exemplified by U.S. Pat. Nos. 6,479,243, 6,399,763, 5,714,153, 5,582,981, and 4,833,077, all incorporated herein by reference. The preparation of vaccines that contain flavivirus sequences as active ingredients is generally well understood in the art by analogy, as exemplified by U.S. Pat. Nos. 5,958,895, 6,004,799, and 5,620,896, all incorporated herein by reference.

VII. PHARMACEUTICAL COMPOSITIONS AND ROUTES OF ADMINISTRATION

Pharmaceutical compositions including NS5A peptides and polypeptides will be formulated along the line of typical pharmaceutical drug and biological preparations. A discussion of formulations may be found in Remington's Pharmaceutical Sciences (1990). The percentage of active compound in any pharmaceutical preparation is dependent upon both the activity of the compound, in this case ability of NS5A agents to inhibit HIV replication. Typically, such compositions should contain at least 0.1% active compound. The percentage of the compositions and preparations may, of course, be varied and may conveniently be between about 2 to about 60% of the weight of the unit. The amount of active compounds in such therapeutically useful compositions is such that a suitable dosage will be obtained.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injection is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, phenylmecuric nitrate, m-cresol, and the like. In many cases, it will be preferable to use isotonic solutions, for example, sugars or sodium chloride. Prolonged absorption of the injectable compositions can be brought about by the use in the compositions of agents delaying absorption, for example, aluminum monostearate, and gelatin.

Sterile injectable solutions are prepared by incorporating the active compounds in the required amount in the appropriate solvent with various of the other ingredients enumerated above, as required, followed by sterile filtration. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques that yield a powder of the active ingredient plus any additional desired ingredient from a previously sterile-filtered solution thereof.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

The active compounds of the present invention can be formulated for parenteral administration, e.g., formulated for injection via the intravenous, intramuscular, intrathoracic, sub-cutaneous, or even intraperitoneal routes. Administration by i.v. or i.m. are specifically contemplated. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In certain embodiments, it may be desirable to provide a continuous supply of therapeutic compositions to the patient. For intravenous or intraarterial routes, this is accomplished by drip system. For various approaches, delayed release formulations could be used that provided limited but constant amounts of the therapeutic agent over and extended period of time. For internal application, continuous perfusion may be preferred. This could be accomplished by catheterization followed by continuous administration of the therapeutic agent. The time period for perfusion would be selected by the clinician for the particular patient and situation, but times could range from about 1-2 hours, to 2-6 hours, to about 6-10 hours, to about 10-24 hours, to about 1-2 days, to about 1-2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Peptides or polypeptides may be administered in a dose that can vary from 0.01, 0.05, 0.1, 0.5, 1, 5, 10, 20, 30, 40, 50, 60, 70, 80, 90, 100 mg/kg of weight to 50, 60, 70, 80, 90, 100, 110, 120, 130, 140, 150, 160, 170, 180, 190, 200 mg/kg of weight in one or more daily, weekly, monthly, or yearly administrations during one or various days, weeks, months, or years. The antibodies can be administered by parenteral injection (intravenous, intraperitoneal, intramuscular, subcutaneous, intracavity or transdermic). For viral vectors, one generally will prepare a viral vector stock. Depending on the kind of virus and the titer attainable, one will deliver 1 to 100, 10 to 50, 100-1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

In many instances, it will be desirable to have multiple administrations of the NS5A agent. The compositions of the invention may be administered 1, 2, 3, 4, 5, 6, 7, 8, 9, 10, or more times. The administrations will normally be at from one to twelve week intervals, more usually from one to four week intervals. Periodic re-administration will be desirable with recurrent exposure to the pathogen (e.g., HIV). For example, an HIV positive mother would be re-inoculated prior to parturition from a second pregnancy.

Precise amounts and delivery regimen for the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

In a particular embodiment of the invention, the NS5A agent may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Current in vivo lipid delivery methods use subcutaneous, intradermal, intratumoral, or intracranial injection to avoid the toxicity and stability problems associated with cationic lipids in the circulation. The DOTAP:cholesterol lipid formulation is said to form a unique structure termed a "sandwich liposome." This formulation is reported to "sandwich" DNA between an invaginated bi-layer or 'vase' structure. Beneficial characteristics of these lipid structures include a positive p, colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990).

VIII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Background. HIV survival is associated with low surface expression of CCR5, high circulating levels of RANTES, SDF-1, a Th 1 cytokine profile and slow CD4 decline. T cell death is associated with Fas-mediated apoptosis. GBV-C in vitro infection was shown to increase release of chemokines and to decrease surface expression of CCR5. Nunnari et al. found a Th1 polarized cytokine profile relative to Th2 cytokines among HIV-infected people with GBV-C infection compared to those without, and several studies found prolonged survival and preserved CD4 counts. The molecular mechanisms for the in vitro effects of GBV-C are not well understood.

Infection with GB virus type C is associated with prolonged survival in all studies of HIV-infected people that were conducted prior to the availability of HAART (Zhang et al., 2006; Toyoda et al., 1998; Lefrère et al., 1999; Bjorkman et al., 2004), although some of the studies were not statistically significant (Williams et al., 2004; Van der Bij et al., 2005). Persistent infection appears necessary for this beneficial association (Zhang et al., 2006), and clearance of viremia, which frequently occurs, is associated with a poor prognosis (Toyoda et al., 1998; Lefrère et al., 1999; Williams et al., 2004). In a Sicilian HIV-infected cohort, GBV-C infection was associated with maintenance of Th1 cytokines (IL-2, IL-12), and low levels of Th2 cytokines (IL-4, IL-10) over time (Nunnari et al., 2003). In contrast, those without GBV-C had falling Th1 and rising Th2 cytokines over time (Nunnari et al., 2003), suggesting that GBV-C may promote a Th1 cytokine profile. The GBV-C nonstructural phosphoprotein NS5A is a potent inhibitor of HIV replication in CD4+ T cell lines, in part by down-regulating the HIV co-receptor CXCR4 and inducing the release of SDF-1 (Xiang et al., 2006). Similar to the related HCV NS5A, GBV-C NS5A inhibits PKR function (Xiang et al., 2005). The HCV NS5A has been shown to inhibit apoptosis, although this has not been studied in GBV-C NS5A. The inventors have utilized an in vitro replication model (PBMCs) to examine the effect of GBV-C replication on expression for chemokine receptors, chemokines, Th1 and Th2 cytokines-related genes. The effect of GBV-C NS5A protein on these genes was also examined. In addition, the effect of GBV-C replication in PBMCs and NS5A expression in Jurkat cells on the surface expression of chemokine receptors, release of chemokines and response to Fas-mediated apoptosis was studied by flow cytometry.

Figure 2A:
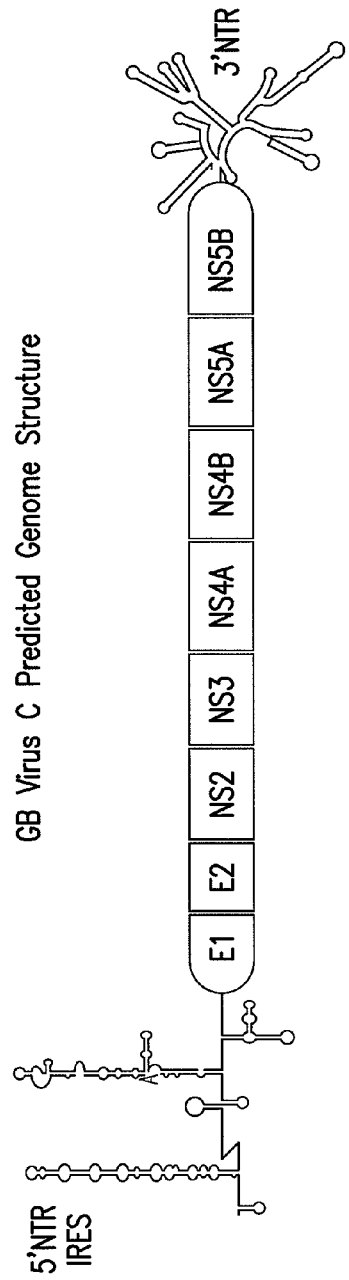
FIG. 2A-2B. Schematic illustration of the predicted GBV-C genome organization (FIG. 2A) and the HCV polyprotein translation processing scheme, which GBV-C is thought to resemble (FIG. 2B; Penin et al. 2004).
Figure 2B:
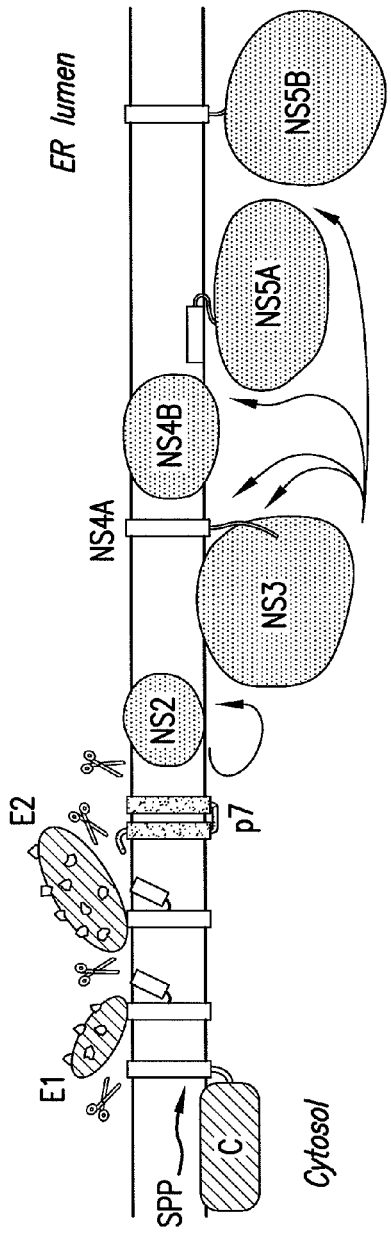
Figure 4:
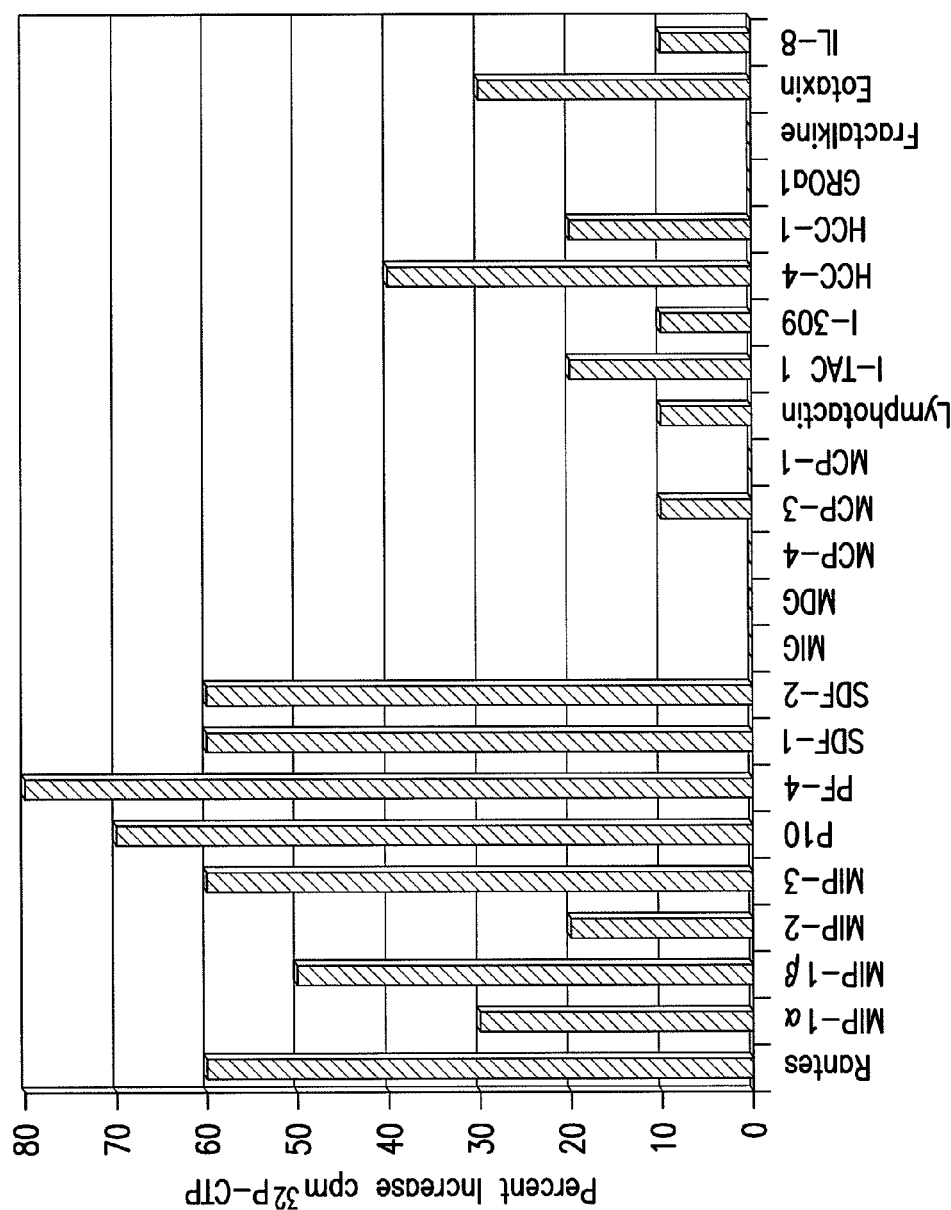
FIG. 4. Effects of GBV-C infection on PBMC chemokine gene expression. Chemokine genes upregulated in GBV-C infected PBMCs relative to mock-infected PBMCs (percent increase) using differential hybridization as described in methods. Data represent results from 4 individual experiments FIG. 5. GBV-C infection down-regulates CCR5 surface expression in PBMC cultures.
Figure 5:
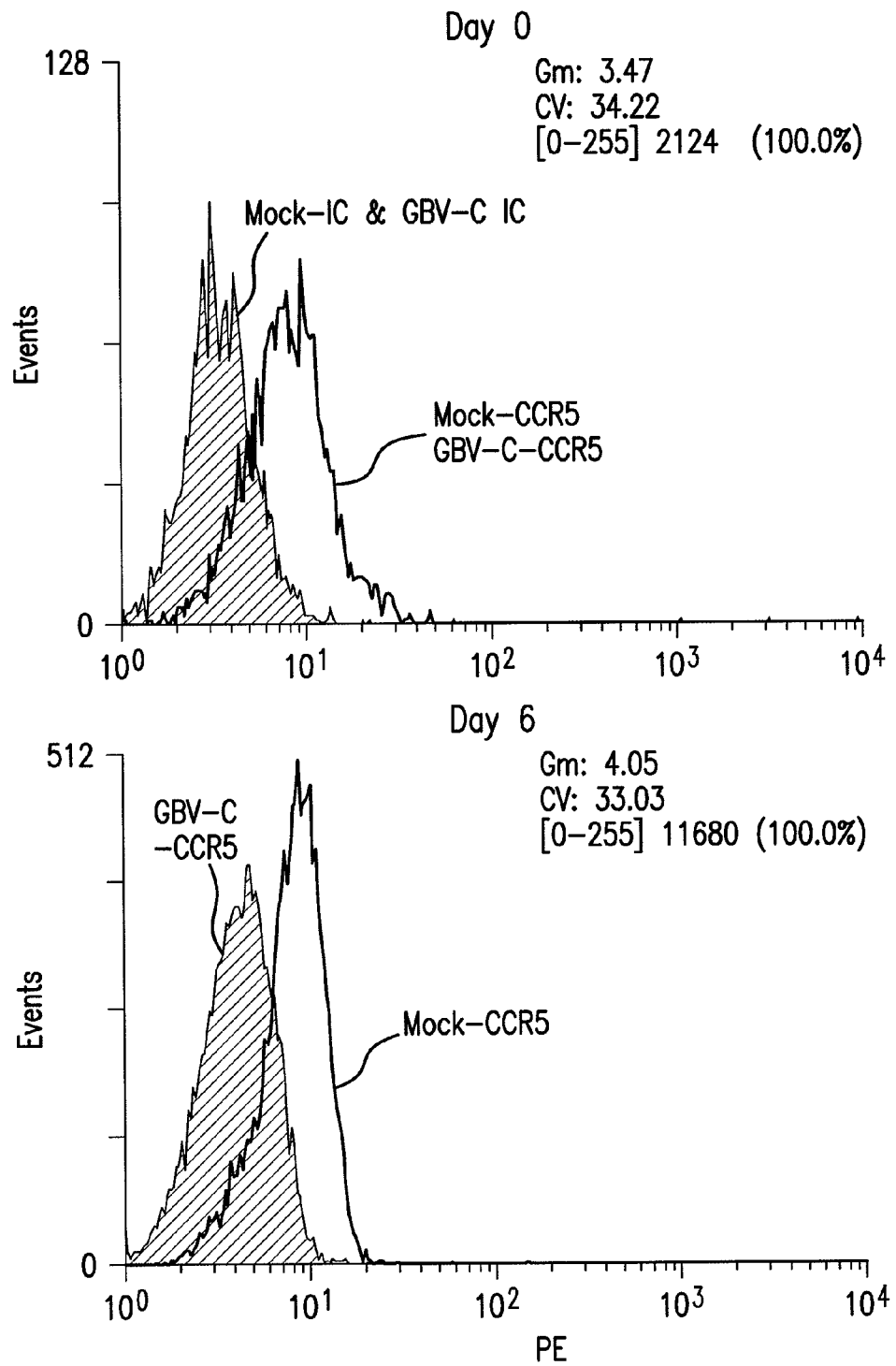
Figure 6:
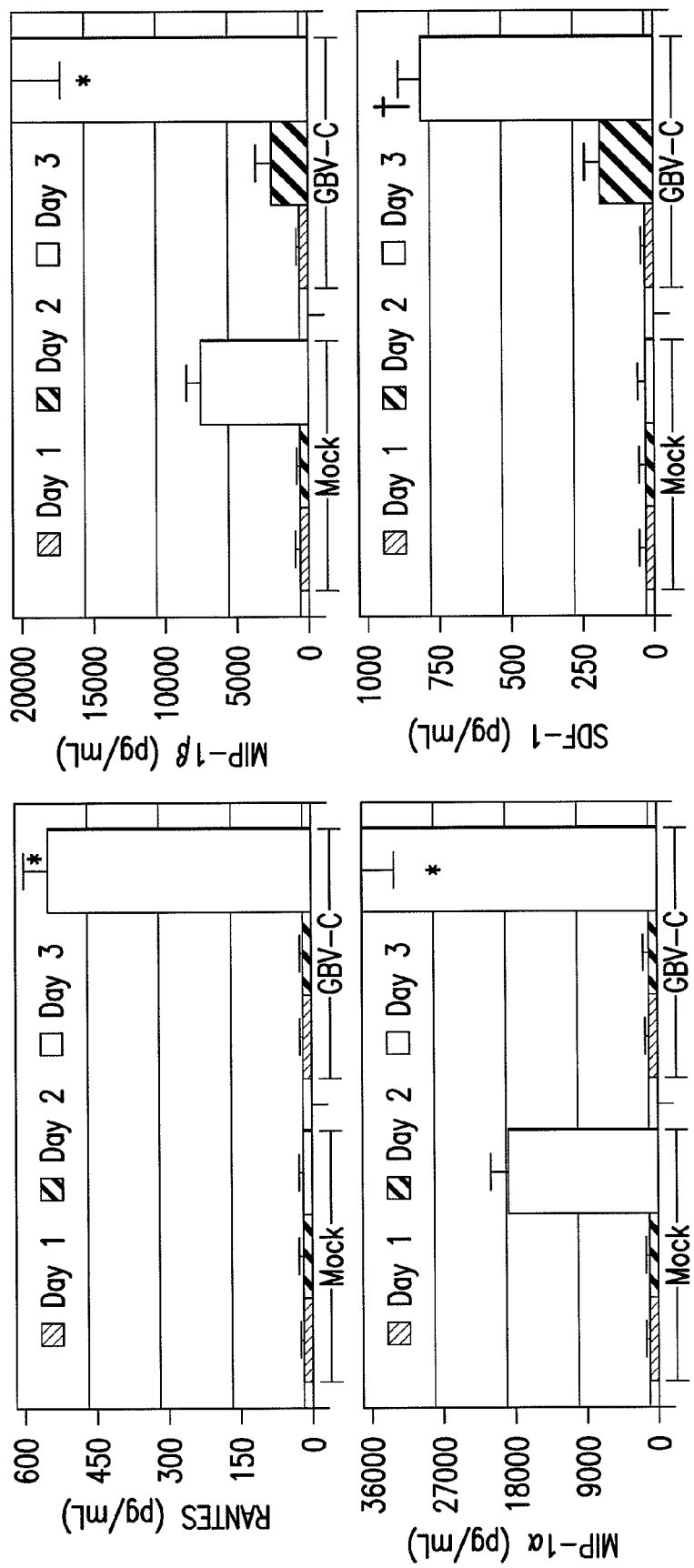
FIG. 6. Chemokine release into culture supernatants in GBV-C versus mock infected PBMCs on days 1, 2, and 3 post-infection.
Figure 8:
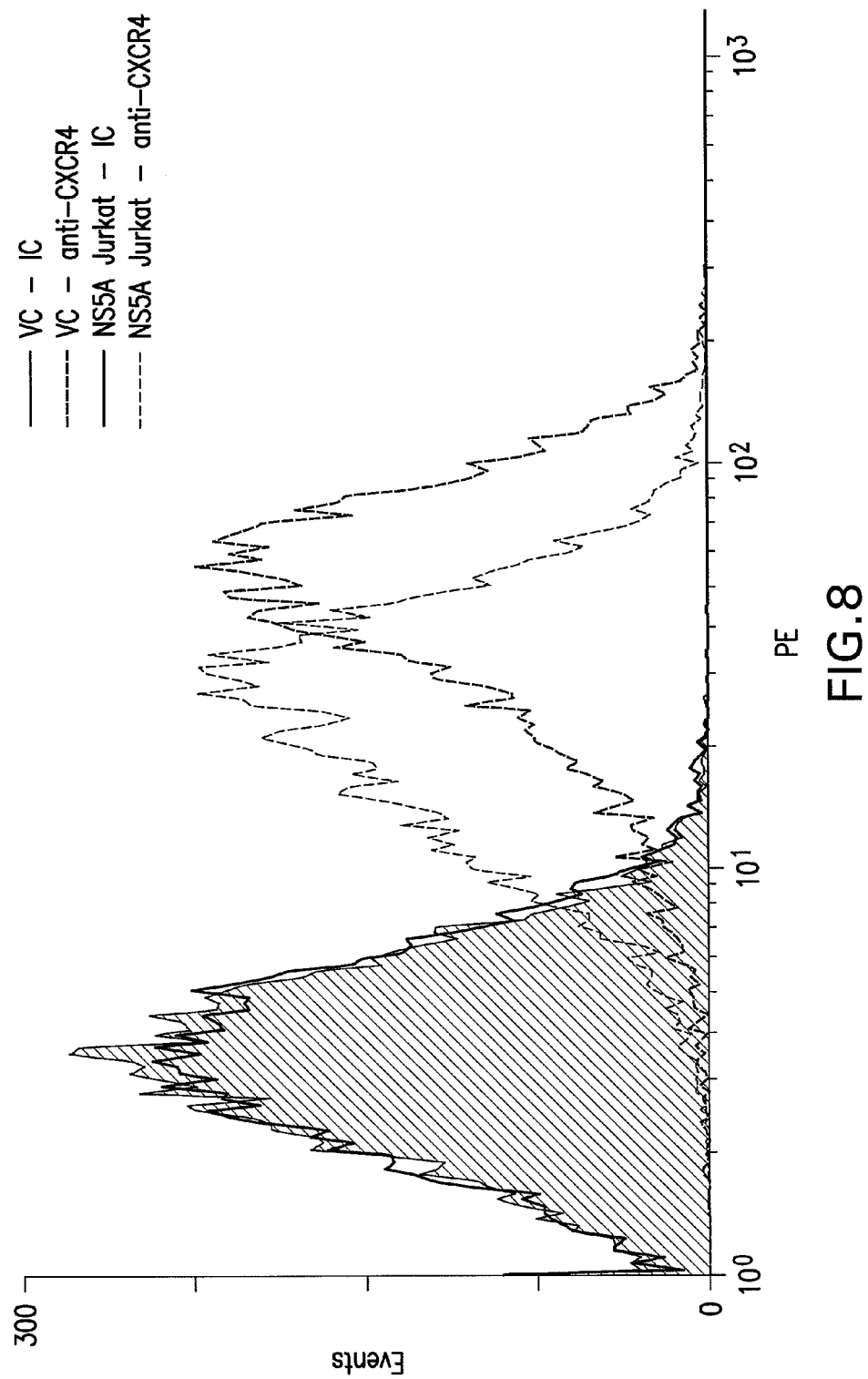
FIG. 8. Consistent with mRNA data, NS5A down-regulates surface expression of CXCR4 on Jurkat cells relative to vector control cells (VC). IC=isotype control antibody.
Figure 9:
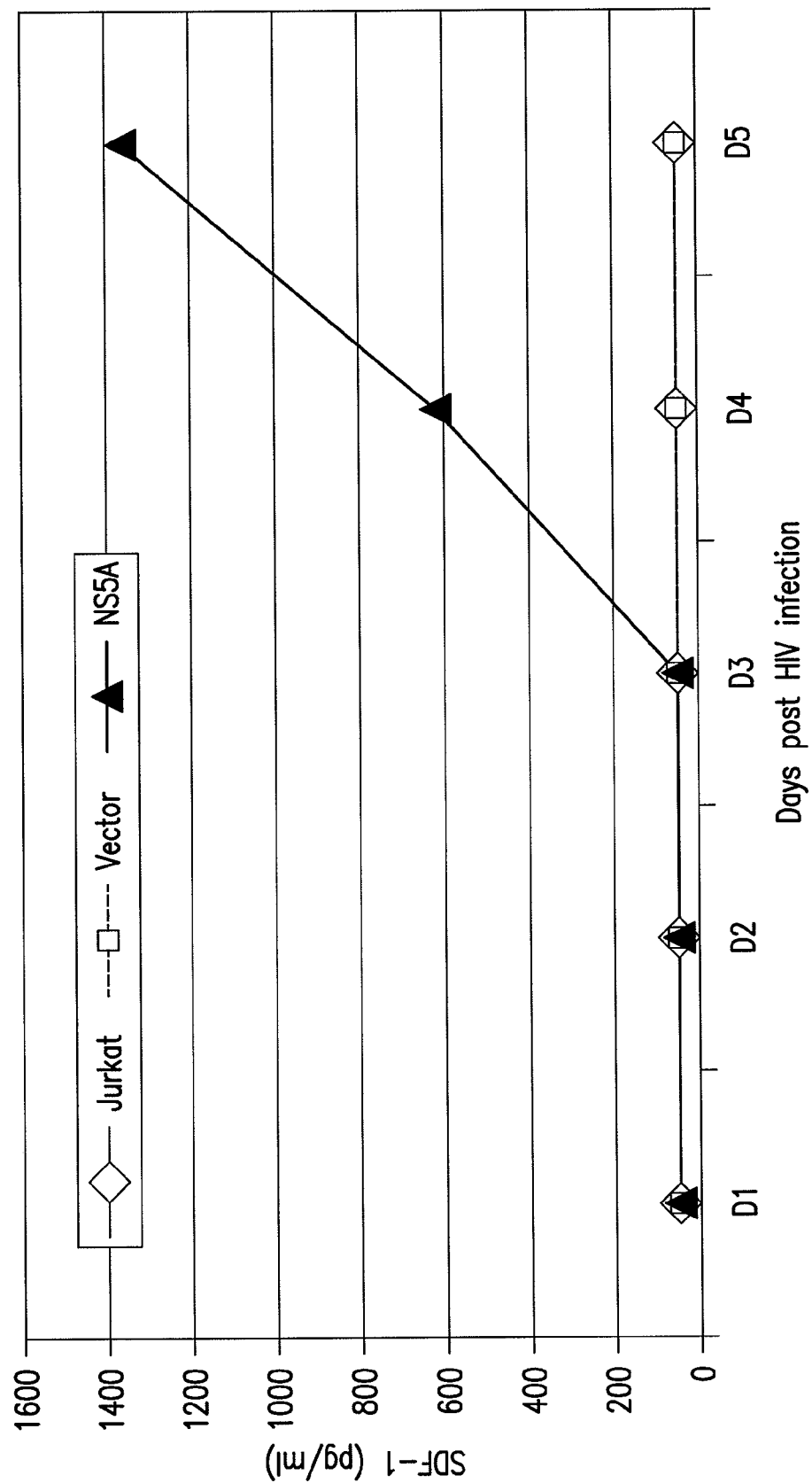
FIG. 9. Consistent with mRNA data, NS5A expression caused significantly increased levels of SDF-1 to be released into culture supernatants FIG. 10. GBV-C infection is associated with maintenance of a serum Th1 cytokine profile. Data represent serum IL-2, IL-12, IL-4, and IL-10 levels measured in stored serum from HIV-infected Sicilians over an 8 year period.

Methods. GBV-C infected PBMCs or Jurkat cells expressing GBV-C NS5A protein were examined for chemokine receptor expression and Fas-mediated apoptosis (flow cytometry), chemokine release (EIA), and cytokine gene expression compared to control cells. NS5A expressing cells were also examined for cytokine, chemokine and apoptosis-related gene expression by real-time profiling (compared to control cells). mRNA levels were normalized by housekeeping genes and studies performed in triplicate. (1) PBMCs were infected with GBV-C or mock virus preparations as previously described (Xiang et al., 2004). Replication was monitored by viral RNA in culture supernatants and NS5A protein expression in cell lysates (FIG. 1). (2) GBV-C NS5A is thought to be part of the replication complex that assembles on the ER membrane (FIG. 2). Jurkat cells stably expressing GBV-C NS5A in a Tet-Off plasmid containing GFP were constructed and characterized (FIG. 3). (3) Gene expression profiling utilized two "SuperArray" methods. Total cellular RNA was prepared from GBV-C- and Mock-infected PBMCs, and differential expression of cytokine and chemokine genes was measured by comparing labeled cDNA in each cell population as previously described (Xiang et al., 2004). For NS5A and vector control Jurkat cells, mRNA levels were monitored by real-time PCR assessing chemokine-, Th1,2,3 cytokine- and apoptosis-related genes. Each plate contains 84 relevant genes that are normalized against 5 housekeeping genes. Plates were done in triplicate with 3 independent RNA preparations for sample and controls. (5) CCR5 and CXCR4 were analyzed by flow cytometry as previously described (Xiang et al., 2006). Chemokine release into culture supernatants was assessed by ELISA as described (Xiang et al., 2006). (6) Apoptosis in GBV-C- and mock-infected PBMCs was measured by Annexin V staining and in Jurkat cells, by measuring pan-caspase activity, both by flow cytometry. Apoptosis was induced by PBS, CH11 (anti-Fas Mab, 50 µg/ml), or TNF (100 ng/ml)

Results: GBV-C infection down-regulated CCR5 expression and chemokine release. Infection also resulted in resistance to Fas-mediated apoptosis and downregulation of Th2 cytokine genes relative to control cells. GBV-C NS5A protein demonstrated a complex effect of GBV-C NS5A protein expression on cytokine, chemokine, and apoptosis related gene expression. Significant up- or down-regulation occurred in 25 and 34 genes respectively. CXCR4 and CCR2 mRNAs were significantly down-regulated, supporting HIV replication inhibition. Genes promoting Th1 cytokines were upregulated (CCR7, TNF, TBX21) and Th2 genes were down-regulated (IL-4, IL-10, IL-13, ICOS). The gene for the anti-apoptotic protein BCL2 was increased 6-fold (p=0.00002) and Casp 1 mRNA was down 17-fold (p=0.017).

GBV-C infection and expression of GBV-C NS5A protein have pleotropic effects on cellular chemokine, chemokine receptor, cytokine and apoptosis-related genes. The results of GBV-C chemokine gene expression include HIV replication inhibition, and Th cytokine profiles mimic those of slow/non-progressors. The effect on Fas-mediated apoptosis of CD4+ T cells is consistent with slower CD4+ T cell decline. Further understanding of the complex interactions between GBV-C infection and NS5A protein may identify novel approaches for HIV inhibition and methods to delay CD4 decline.

Chemokines. GBV-C infection alters chemokine-related mRNA expression in PBMCs resulting in induction of release of relevant chemokines and downregulation of CCR5

GBV-C NS5A expressed in Jurkat cells upregulates SDF-1 (CXCL12) gene expression and induces the release of SDF-1 from Jurkat cells. NS5A also down-regulates CXCR4 mRNA expression with resultant decreased surface expression of CXCR4.

Th Cytokines. GBV-C infection upregulates Th1 cytokine mRNA levels (IL2 and IL12) and down regulates IL-4, IL-10 and IL-13 in PBMCs.

GBV-C NS5A expression in Jurkat cells down-regulates IL-4, IL-10, IL-13, ICOS and IL-18 mRNA expression.

Figure 10:
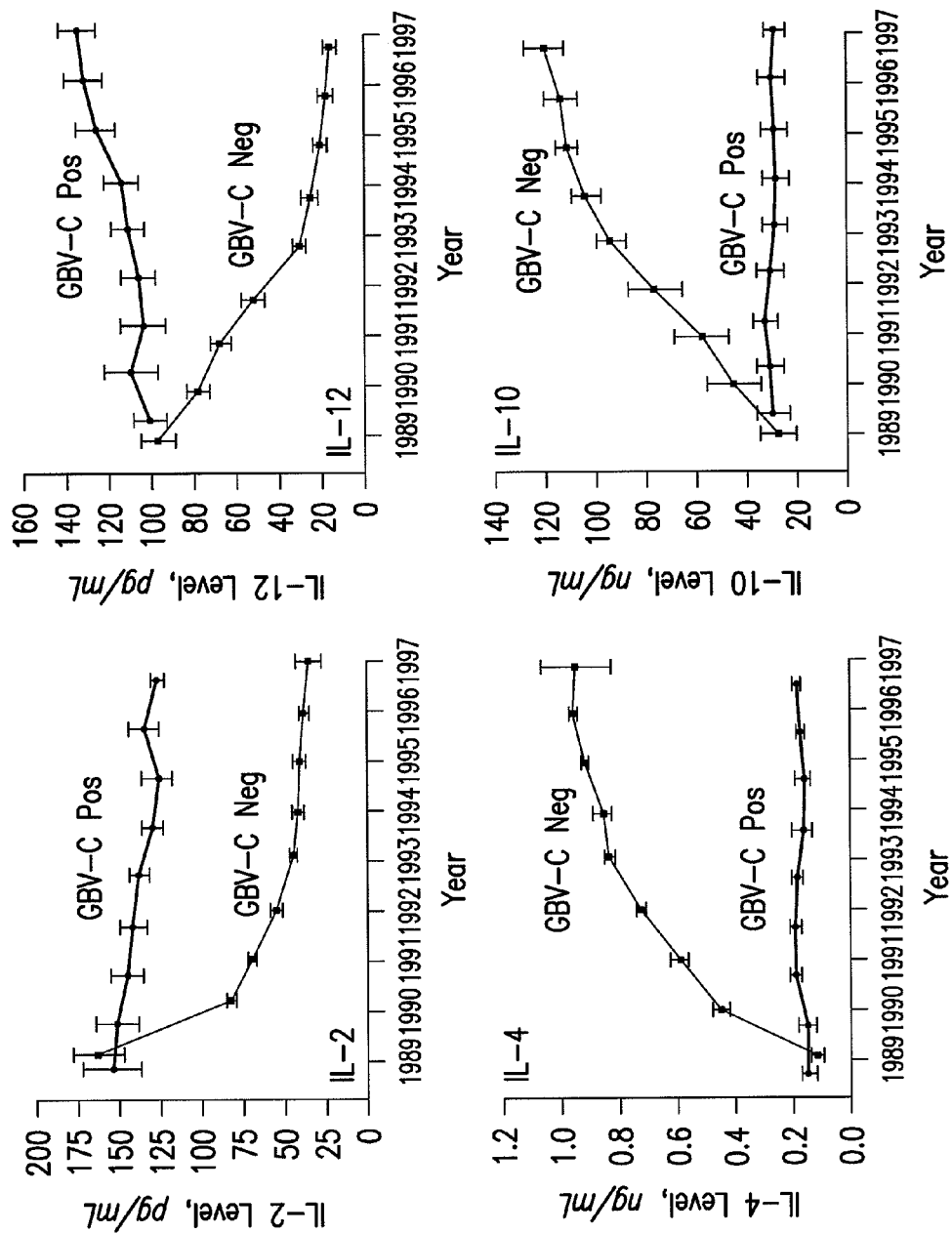
Figure 11:
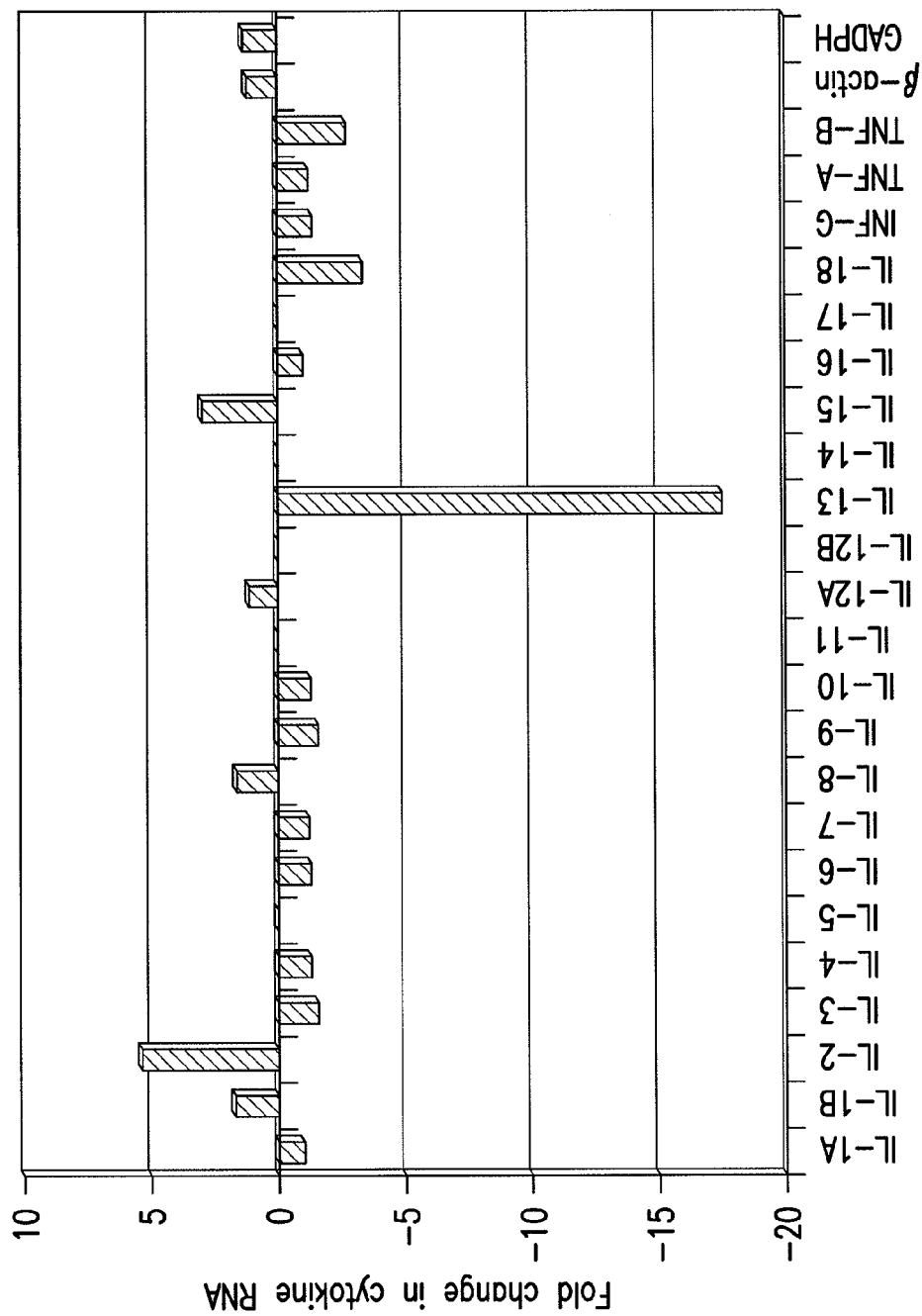
FIG. 11. Cytokine gene expression in GBV-C infected PBMCs. mRNA levels in GBV-C infected PBMCs relative to mock-infected (by "fold-change") using differential hybridization as described in methods. Data represent results from 4 individual experiments. Note downregulation of IL-4, IL-10, IL-13 and IL-18.

These data are consistent with GBV-C infection and NS5A protein promoting a Th1 cytokine profile as observed in a clinical study (FIG. 10), and may have relevance for HIV disease progression and potentially the natural history of other diseases.

Figure 14:
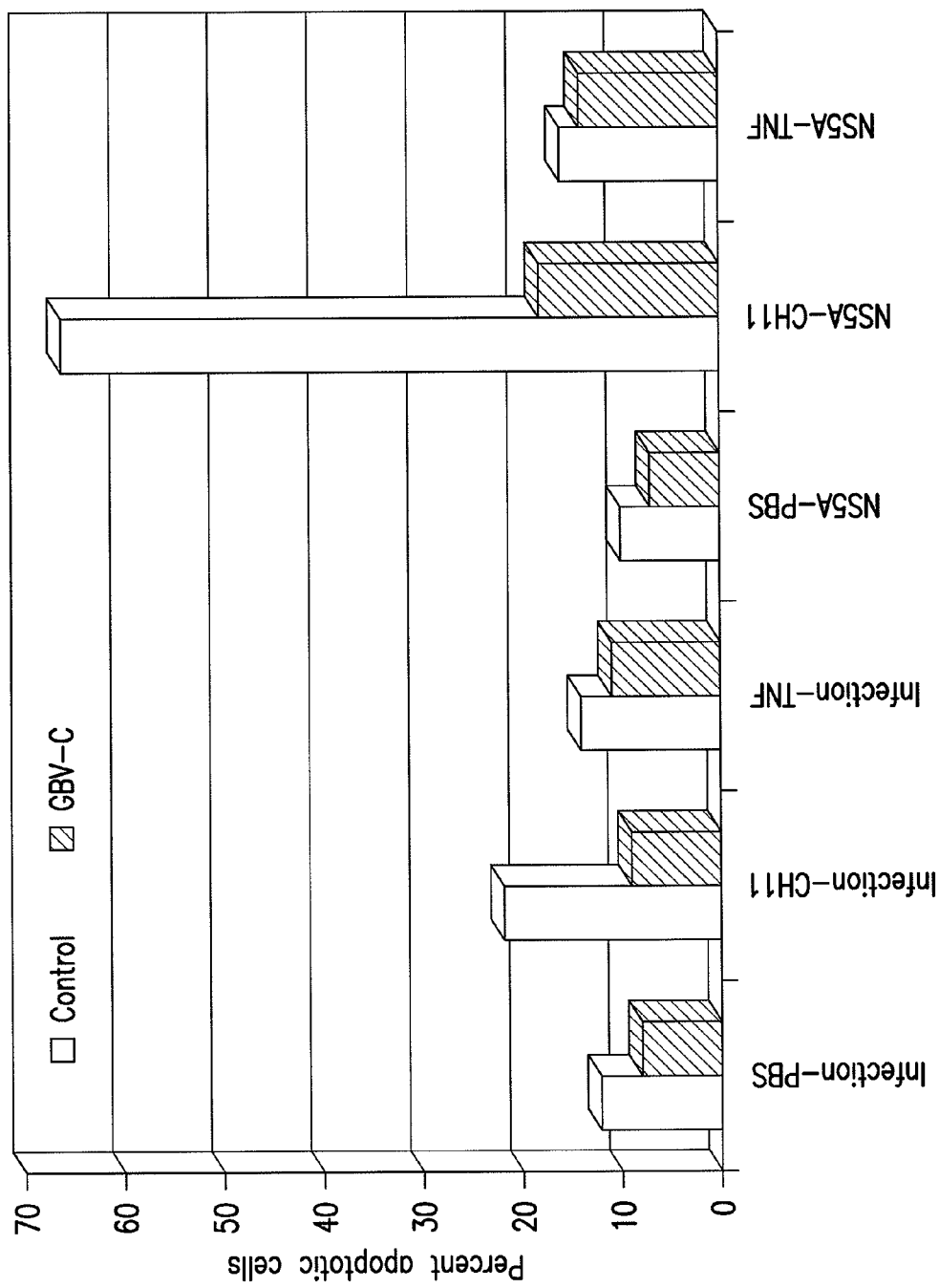
FIG. 14. GBV-infection (PBMCs) and NS5A protein expression (Jurkat cells) renders cells relatively resistant to Fas-mediated but not TNF-induced apoptosis. Cells were incubated with either PBS, CH11 (anti-Fas Mab), or TNF. Apoptosis in infected cells was measured Annexin V staining and in Jurkat cells by activated caspase (pan-caspase), both by flow cytometry.
Figure 15:
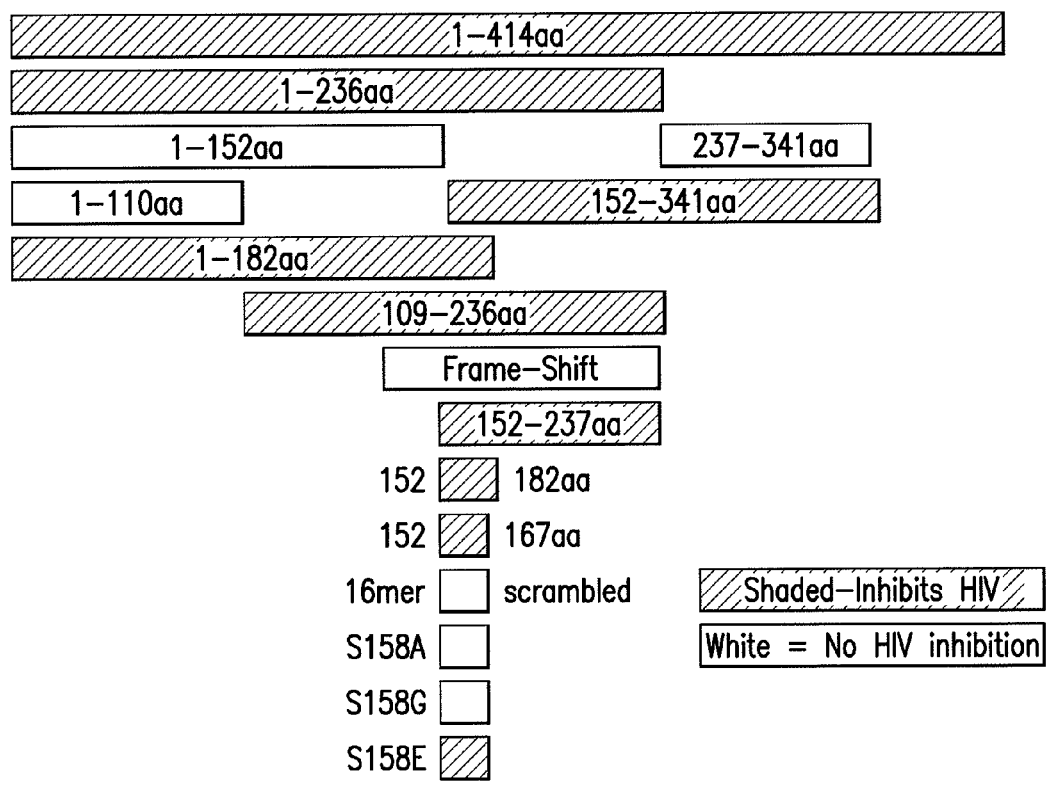
FIG. 15. Jurkat cell lines stably expressing NS5A deletion mutants as indicated. Full length NS5A (1-414) and mutants with various deletions are shown. "Frame Shift" is a control sequence in which a +1 frame shift inserted at NS5A aa #126, leading to a missense peptide expression. The FS has the entire RNA transcript of 152-237, but does not translate the NS5A protein. Shaded boxes indicate cell lines that inhibit HIV replication, and open boxes are cells that do not inhibit HIV replication. 16-mer scrambled=amino acids from 152-167 out of order AVPDAGRIAPDVASDW (SEQ ID NO: 26). The serine at 158 was mutated to an alanine, glycine or glutamic acid as noted.

Apoptosis. GBV-C infection leads to relative resistance to Fas-mediated apoptosis in PBMCs (FIG. 14).

GBV-C NS5A protein expression results in up-regulation of BCL2 mRNA and TNF mRNA in Jurkat cells. NS5A expressing cells were relatively resistant to FAS-mediated apoptosis, but not TNF-mediated apoptosis (data not shown).

Conclusions. Both GBV-C infection and NS5A protein expression modulate cellular chemokine and chemokine receptor expression resulting in HIV replication inhibition. GBV-C infection and NS5A expression promotes a Th1 cytokine profile, predominantly by down-regulating Th2 cytokines GBV-C infection and NS5A protein expression render PBMCs and CD4+ T cell lines relatively resistant to Fas-mediated apoptosis. All of these effects may potentially result in delayed HIV disease progression and prolonged survival. These biological data support a causal relationship for the epidemiological association between GBV-C and prolonged survival.

Example 2

GBV-C NS5A and HIV inhibition. After demonstrating that GBV-C co-infection of PBMCs with HIV results in inhibition of HIV replication, and that GBV-C induces the chemokines that are the ligands for CCR5 and CXCR4 (Xiang et al., 2004), the inventors began to investigate specific viral proteins to see if they might be the reason for these findings. The inventors studied a GBV-C polyprotein and the NS5A phosphoprotein and, using a yeast genetic system that shares some features with yeast two-hybrid systems, found that NS5A inhibited PKR function (Xiang et al. 2005). Using the clones containing full-length IFN-R (resistant to interferon) and IFN-S (sensitive to interferon therapy) GBV-C NS5A sequences, CD4+ Jurkat T cell lines were generated expressing these proteins in a modified "Tet-Off" expression system that allows negative selection (hygromycin), and positive selection (GFP) as a single (bicistronic) message. Using Amaxa nucleofectin technology, the inventors have had considerable success in generating a series of stable, clonal Jurkat cell lines expressing heterologous proteins. Negative control cell lines were also generated containing the vector expressing hygromycin without (VC) or with GFP (VC-GFP).

The inventors were surprised to find that expression of both IFN-S and IFN-R NS5A led to potent inhibition of HIV replication (>98%) in these cells compared to control cell lines (Xiang et al., 2006). A dose-response was observed when varying the concentration of doxycycline in NS5A expressing cells, and all HIV isolates tested were inhibited (Xiang et al., 2006). Cells were maintained in doxycycline (5 μg/ml) for ≧3 passages to ensure that NS5A expression was minimal, then doxy was removed to turn on NS5A expression. Three days after removal of doxycycline, SDF-1 release into culture supernatants was significantly higher in NS5A cells than either VC-GFP cells or cells maintained in doxycycline suggesting that this may partly explain the mechanism of action of NS5A. However, incubation of cells in neutralizing anti-SDF-1 antibodies did not completely block the effect of NS5A on HIV, thus this did not appear to completely explain the HIV inhibition (Xiang et al., 2006). CXCR4 expression on the cell surface of Jurkats was lower in NS5A expressing cells, even when maintained in anti-SDF-1 antibodies, suggesting that intracellular expression of NS5A leads to decreased surface expression of CXCR4 independently from the NS5A-induction in SDF-1. To ensure that the effect was due to NS5A protein expression and not a result of RNA structural effects on cells, Jurkat cells were selected that contained a frame-shift mutation leading to expression of 26 missense amino acids followed by all of the NS5A RNA in the inhibitory vector, followed by the GFP.

There was a concern that the NS5A effect would be limited to GBV-C infected cells, as the protein is only expressed during active replication, is anchored in the ER, and is not part of the virion. However, SDF-1 is released from NS5A expressing cells and from GBV-C infected cells. When culture supernatants from GBV-C infected cells were added to uninfected cells, and challenged with HIV, the SDF-1 and beta chemokines present inhibited both R5 and X4 HIV isolates (Jung et al., 2005), thus demonstrating that there is a "bystander" effect on HIV replication, and the GBV-C effect is not only at the level of the individual infected cell.

Mapping functional regions of GBV-C NS5A. To determine which region(s) of NS5A inhibit HIV, the inventors created a series of cell lines expressing GBV-C NS5A deletion mutants. All cell lines demonstrated GFP expression, linkage of NS5A sequence with GFP by cellular DNA PCR, and when antibodies available, by NS5A western blotting. HIV Infection in these cell lines demonstrated that the HIV inhibitory region requires only amino acids 152-167 (VDG-IPVSWDADARAPA (SEQ ID NO:10)). This region is highly conserved between GBV-C isolates from all 5 genotypes (only variant amino acid is E161D). Although full-length NS5A induced SDF-1 release from cells, the deletion mutant having only 152-167 does not, thus SDF-1 release does not account for all of the HIV inhibitory effect. These data indicate that the serine is critical for the HIV inhibitory effect, and that substitution of a glutamic acid (phosphomimetic substitution (Maciejewski et al., 1995)) maintains the phenotype. This suggests that phosphorylation of the serine is required for the HIV inhibitory effect.

HCV and GBV-B NS5A and inhibition of HIV replication. Because GBV-C shares ~30% overall amino acid identity with HCV and because the Flaviviridae all contain NS5-membrane-associated phosphoproteins with pleotropic effects on cells, the inventors assessed GBV-B and HCV NS5A and Dengue NS5 proteins for HIV inhibitory effect. HCV genotype 1b NS5A was kindly provided to us by Steven Polyak (Univ. of Washington) (Polyak et al., 2001); GBV-B full-length cDNA was kindly provided by Jens Bukh (NIH) (Bukh et al., 1999). Dengue NS5 was provided by Alan Rothman (Univ. Mass) (Medin et al., 2005), and the BVDV full-length clones were kindly provided by Charles Rice (Rockefeller Univ.). The NS5A coding region from HCV and GBV-B, and the full dengue NS5 proteins were cloned into the tet-repressible reporter vector and Jurkat cells expressing these proteins were selected.

Note that the inventors have mapped the HCV inhibitory domain to the structural "domain I" and to a 21 amino acid fragment within this domain. A frame shift construct with the 152-172 sequences does not inhibit HIV confirming the requirement for the peptide sequence. GBV-B is a primate virus that, like HCV, replicates in hepatocytes. The BVDV NS5A is under construction and no data is available yet. Although the HCV NS5A Domain I peptide inhibits HIV replication, it is unlikely that HCV infection would have a significant effect on HIV disease progression because most HCV replication is in hepatocytes. The relevance of these findings is that identification of different NS5A peptide sequences that share HIV inhibitory effect will provide insight into the structure-function relationship behind this observation. These HCV amino acids in this isolate have a conserved histidine at position 6 which, in eukaryotes at least, should not be a phosphorylation target (although prokaryotes phosphorylate histidines). However, in the genotype 1B and 3A there is a tyrosine at position 8 that is not present in some isolates from other genotypes. Thus, if the histidine is not the key amino acid in HCV, the inventors will evaluate the tyrosine present in the construct (genotype 1B) and assess the NS5A of multiple HCV genotypes.

Effect of NS5A on CD4 mRNA and surface expression. The first Jurkat cell line that expressed full-length GBV-C NS5A was maintained in culture for >30 passes. After which these cells were examined for expression of HIV receptors, CXCR4 was down-regulated, CCR5 was not expressed, and there was a nonsignificant reduction in CD4 expression (Xiang et al., 2006). The inventors have used SuperArray "pathway focused" gene expression analysis, and evaluated the chemokine-, Th1,2,3 cytokine- and apoptosis-related gene pathways using this system. These arrays are in a 96-well format, with probes for 5 housekeeping genes, including a standard (actin) dilution curve, a no RNA template and no polymerase controls, and probes for 84 genes relevant to the pathway of interest. Based on published studies (Xiang et al., 2006), down-regulation of CXCR4, upregulation of CXCL12 (SDF-1) was expected, and based on unpublished studies, downregulation of Th2 cytokine genes (IL-4, IL-10, IL-13, ICOS) was expected. These genes were differentially regulated as predicted. However, NS5A expressing cells had significantly and reproducibly less CD4 mRNA compared to vector control (VC) cells (>35-fold). The CD4 surface expression in these cells was tested, and CD4 was present, but significantly reduced. Subsequently, the inventors have tested deletion mutant cell lines for CD4 expression, and discovered that cells expressing the 152-167 GBV-C peptide and the S158E mutants down-regulate CD4, whereas S158A, S158G, scrambled 152-167 peptides and the frameshift cell lines do not. Retrospectively, all cell lines that do not inhibit HIV do not have decreased CD4, and all cell lines that inhibit HIV do have decreased CD4 on their surface. CD4 is still present on these cells, but at greatly reduced density. Clearly this effect of the peptide is involved in inhibiting HIV replication. The inventors have subsequently examined the HCV domain 1, 152-172 peptide (and frameshift), the Dengue NS5 and GBV-B-expressing Jurkat cells, and all HIV-inhibiting constructs down-regulate CD4 while the non-inhibitory cell lines do not. The original GBV-C NS5A cells had markedly reduced NS5A expression following prolonged passage, probably explaining the minimal effect on CD4 seen. The other feature of GBV-C NS5A that was quite surprising was the fact that GBV-C, but not HCV NS5A significantly upregulates TNFα. By assessing TNFα mRNA levels in the different deletion mutant cell lines, the inventors know that this effect requires a different region of NS5A than does the CD4 down-regulation.

TABLE 4

Effects of GBV-C and HCV NS5A on selected mRNA expression in Jurkat cells

| Gene Name | GBV-C Fold Change | p value | HCV fold change |
|---|---|---|---|
| CD4 | −85.4 | <0.001 | −9.5 |
| CD40LG | −4.53 | 0.004 | 2.5 (ns) |
| CCR2 | −4.0 | 0.014 | −2.5 |
| IL10 | −3.1 | 0.004 | −3.2 (ns) |
| IL18 | −2.8 | <0.001 | −1.3 (ns) |
| ICOS | −2.3 | 0.005 | 4.2 |
| IL13 | −2.1 | 0.045 | −2.4 |
| IL4 | −1.7 | 0.039 | −1.1 (ns) |
| CXCR4 | −1.32 | 0.049 | 1.0 |
| CXCL12 (SDF-1) | 1.5 | 0.043 | −1.3 (ns) |
| FASLG | 4.0 | 0.004 | 1.0 (ns) |
| BCL2 | 5.6 | <0.001 | 2.3 |
| IRF4 | 12.9 | 0.011 | 3.0 |
| TNFα | 37.8 | <0.001 | −7.7 |
| TNFSF7 | 186.7 | <0.001 | 19.0 | mRNA levels in Jurkat cells expressing full-length GBV-C NS5A were compared to Jurkat cells containing the vector control expressing GFP (performed in at least 6 replicates). Genes in bold in left column are associated with HIV receptor binding and entry, and the data have been confirmed by flow cytometry or measurement of SDF-1 by ELISA (Xiang et al., 2006). Based on a report that GBV-C-infected HIV-positive people demonstrated maintenance of a Th1 cytokine profile (Nunnari et al., 2003) and other preliminary data (not shown), the inventors studied Th1 and Th2 cytokines GBV-C NS5A down-regulated Th2 cytokines (IL10, IL18, ICOS, IL13, IL4). Of note, Th2 cytokine downregulation and TNFα mRNA expression were different in GBV-C NS5A expressing cells compared with HCV NS5A expressing cells. Finally, BCL2 is upregulated by both HCV and GBV-C NS5A, and HCV NS5A has been shown to inhibit apoptosis. The regulation of Th2 cytokines, TNFα, and BCL2 regulation do not appear to be altered by the NS5A peptide region that inhibits HIV (152-167; data not shown); however, CD4 is down-regulated by this peptide fragment.

Example 3

Figure 25:
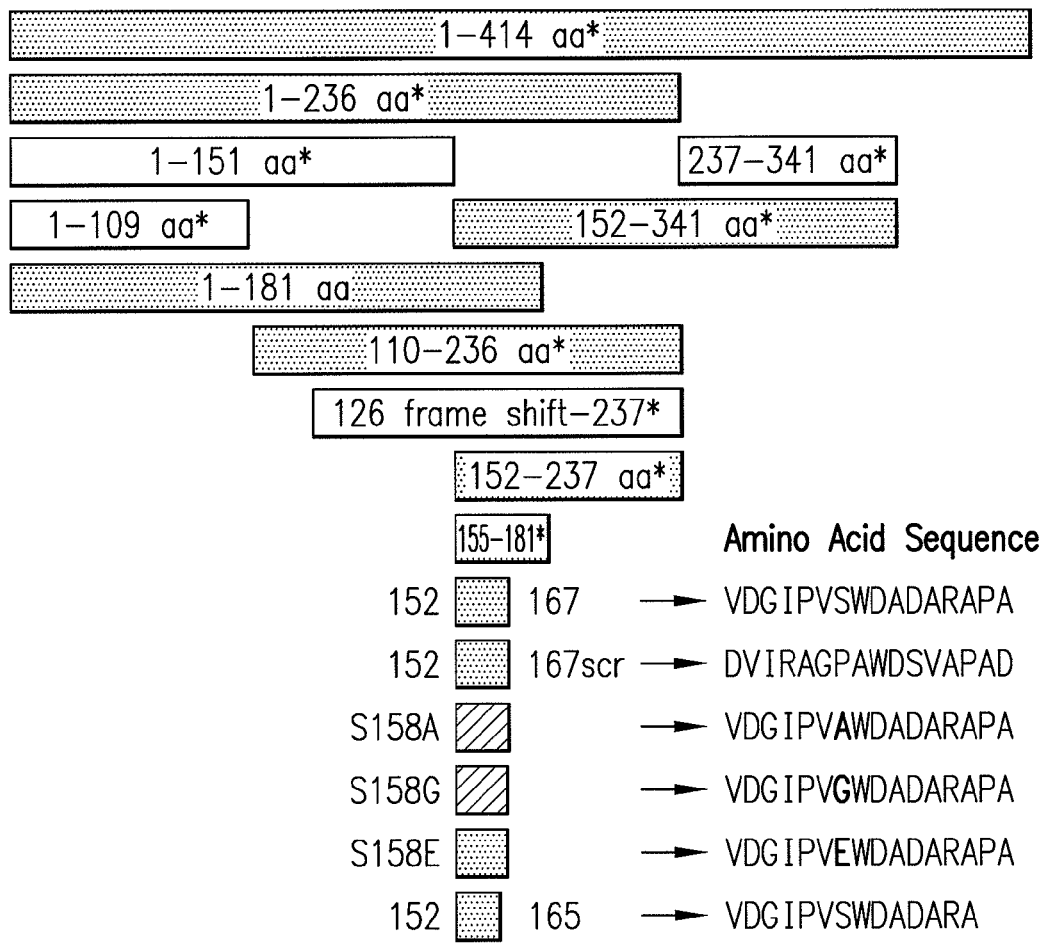
Figure 26:
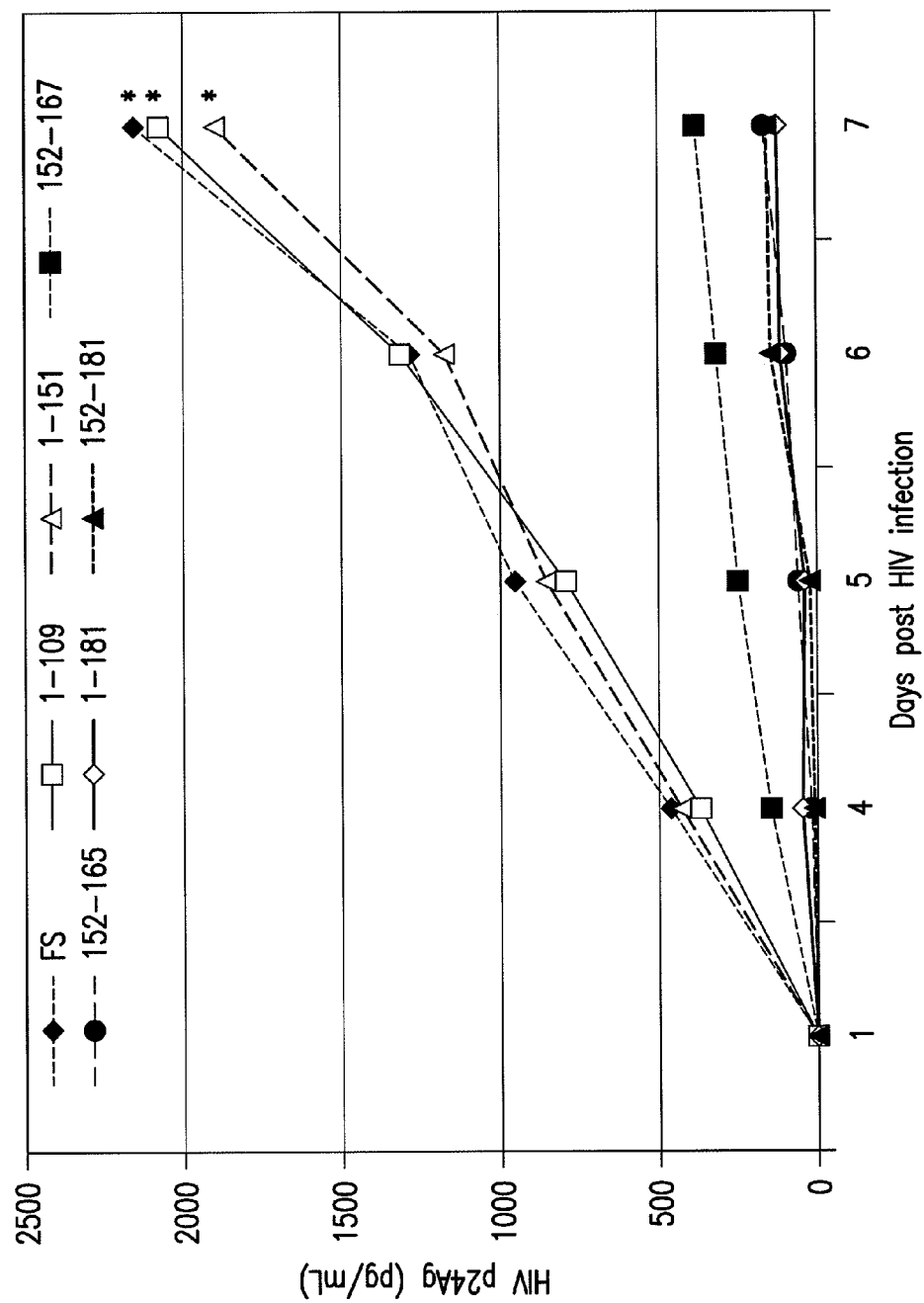

Characterization of GBV-C NS5A peptides required for HIV inhibition. Previous studies demonstrated that stable expression of the GBV-C NS5A protein in a CD4+ T lymphocyte cell line (Jurkat cells) potently inhibited HIV replication (Xiang et al., 2006). The effect required protein expression, as cells expressing GBV-C NS5A RNA in which a frame-shift mutation was introduced to abolish NS5A expression did not inhibit HIV (Xiang et al., 2006). Based on the expression of peptide deletions of NS5A, the HIV inhibitory effect was mapped to amino acids 152-181 (Chang et al., 2007). To further characterize this region, Jurkat cell lines were generated that stably expressed a number of NS5A peptides, including some containing specific amino acid substitutions. Representative NS5A fragments previously described and all new NS5A constructs used to generate stably expressing Jurkat cell lines are summarized in FIG. 25. HIV replication was significantly reduced in cell lines expressing GBV-C NS5A amino acids 1-181, 152-181, 152-167 and 152-165 when compared to HIV replication in cells containing the NS5A frame-shift RNA and cells expressing NS5A amino acids 1-109 and 1-151 (FIG. 26). All Jurkat cell lines that expressed GBV-C NS5A peptides containing amino acids 152-165 significantly inhibited HIV replication compared to the vector and frame-shift controls, whereas cell lines that did not include NS5A amino acids 152-165 did not inhibit HIV (FIG. 26 and data not shown). Thus expression of the 14 amino acid region within the GBV-C NS5A protein (152-165) was sufficient for HIV inhibition.

Figure 27A:
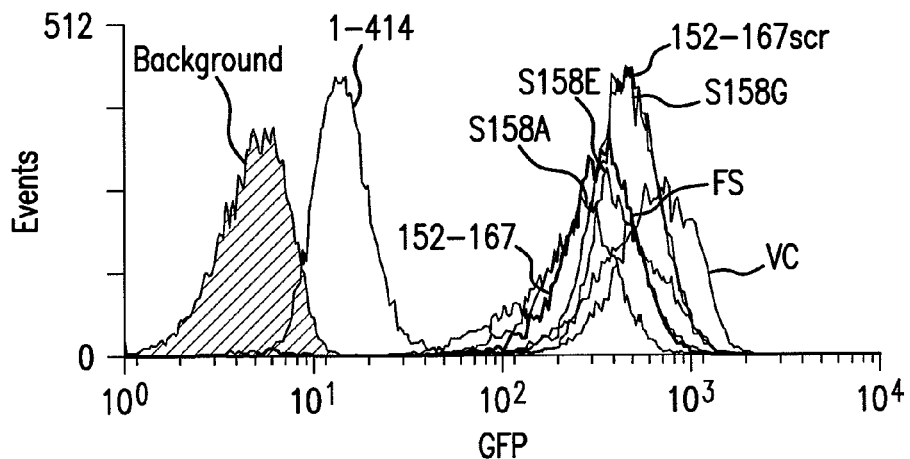
Figure 27B:
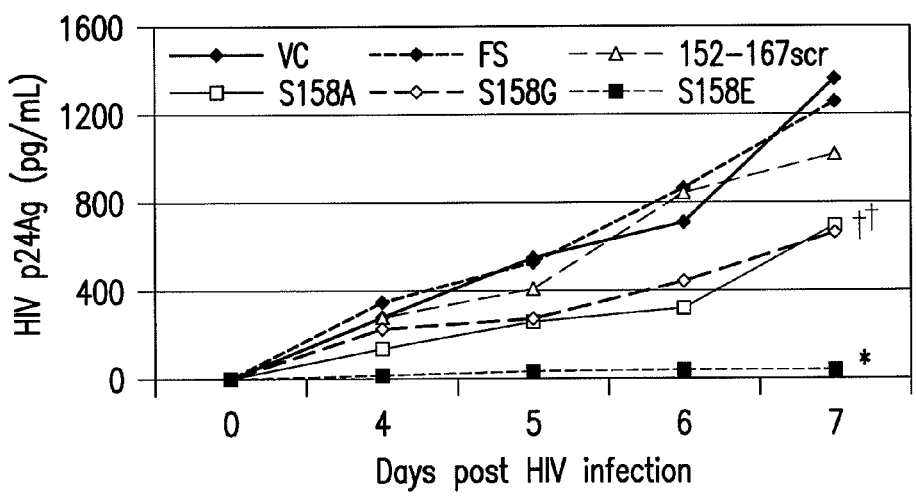

The GBV-C NS5A protein is predicted to be a phosphoprotein, and expression of NS5A in cells results in two immunoreactive proteins consistent with a basal and hyperphosphorylated form (Xiang et al., 2005; Xiang et al., 2006). The 152-167 NS5A peptide contains a serine residue at position 158 that is predicted to be phosphorylated (world-wide-web at cbs.dtu.dk/services/NetPhos/). To assess whether this serine residue is important for the HIV inhibitory effect, cell lines were generated that expressed the NS5A 16mer 152-167 (VDGIPVSWDADARAPA) (SEQ ID NO: 10) or mutated NS5A 16mer peptides with nonconservative substitutions (S158A and S158G) or a phosphomimetic substitution (S158E) (Maciejewski et al. 1995). A negative control cell line was also generated that expressed the 152-167 amino acid sequence in a scrambled order (DVIRAGPAWDSVA-PAD) (SEQ ID NO: 20) (summarized in FIG. 25). Clonal cell lines for each construct were generated that expressed the GFP reporter gene (FIG. 27A), and linkage between the CMV promoter, GBV-C NS5A peptide (or mutant peptide) and GFP was confirmed by sequence analysis of PCR products using cellular DNA as the template as previously described (Chang et al., 2007; Xiang et al., 2006) (data not shown). HIV replication was significantly inhibited in the cell lines expressing the S158E peptide compared to vector control, frame-shift control, S158A and S158G cell lines (FIG. 3B; $p<0.01$ for all). Jurkat cells expressing S158A and S158 G mutations inhibited HIV replication compared to the vector, frame-shift, and 152-167 scrambled peptide controls ($p=0.041$), but this inhibition was significantly less than that observed in cells expressing the S158E peptide (FIG. 27B; $p=0.014$). Thus the serine residue at position 158 appears to be important for optimal HIV inhibition; however, mutation to nonconservative amino acids did not completely abrogate the inhibitory effect. Consistent with prior studies (Xiang et al., 2006), expression of full-length and NS5A peptides did not have any morphologic effects on Jurkat cells nor did they alter viability (trypan blue exclusion and MTT assay) or growth kinetics (data not shown).

To determine if GBV-C NS5A expression was specific for HIV replication inhibition, Jurkat cells stably expressing the full-length GBV-C NS5A (1-414), the 152-181 NS5A peptide, vector control (expressing GFP), and parental Jurkat cells were infected with mumps virus (MOI=1.0; Jeryl-Lynn [vaccine] strain). The infectious titer of mumps in culture supernatants collected four days post-infection was assessed in Vero cells and FIG. 3C illustrates that mumps was not inhibited in cells expressing GBV-C NS5A compared to parental or control cells. The mumps titer was reproducibly higher in cells expressing GBV-C NS5A by one to three $\log_{10}$ ($p=0.029$). This enhancement requires more of the NS5A protein than does HIV inhibition, as the 152-181 NS5A peptide did not enhance mumps virus replication.

Figure 28:
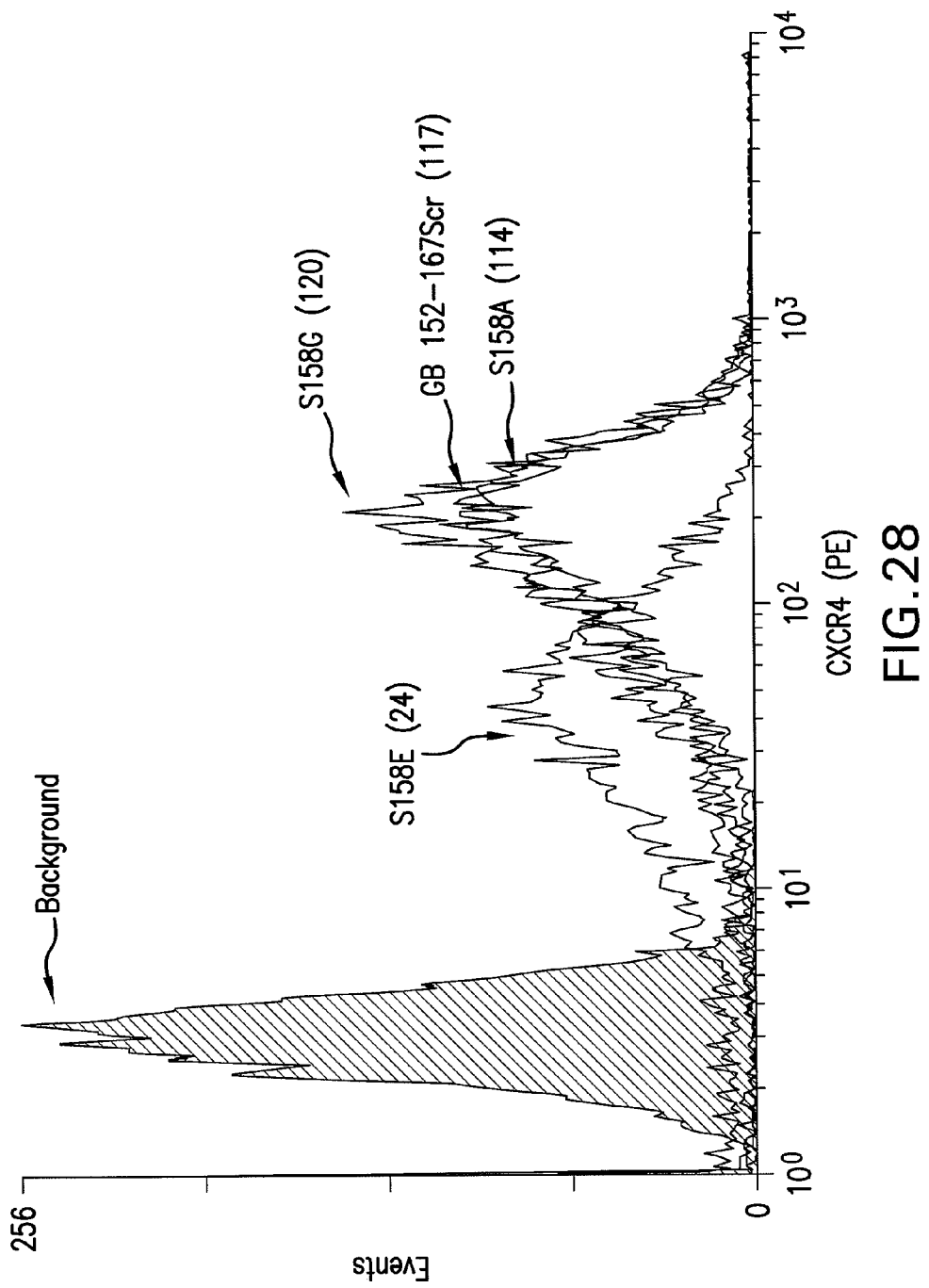

GBV-C NS5A peptide expression and chemokine receptors: Expression of GBV-C NS5A in Jurkat cells was previously shown to down-regulate CXCR4 surface expression (Xiang et al., 2006). The effect of the GBV-C NS5A peptides and controls on the surface expression of HIV co-receptors CXCR4 and CCR5 was assessed by flow cytometry. CXCR4 was reduced on cells expressing the GBV-C NS5A peptides in which HIV replication was inhibited, and not in control cell lines or cell lines expressing the S158A, S158G, or scrambled peptides (FIG. 28). CCR5 was not expressed on the Jurkat cell lines (data not shown).

Figure 29A:
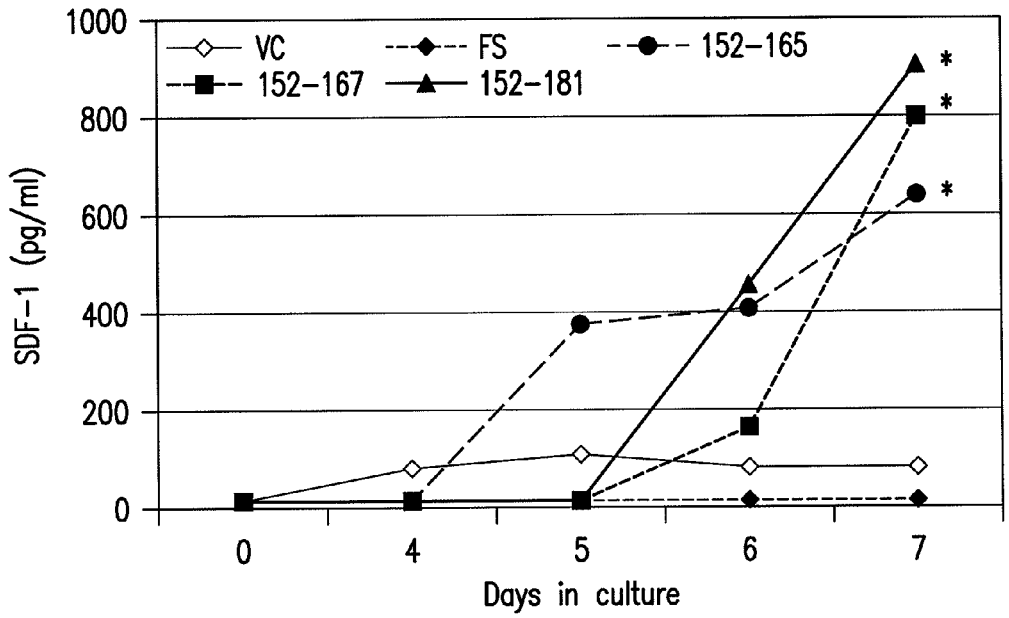
Figure 29B:
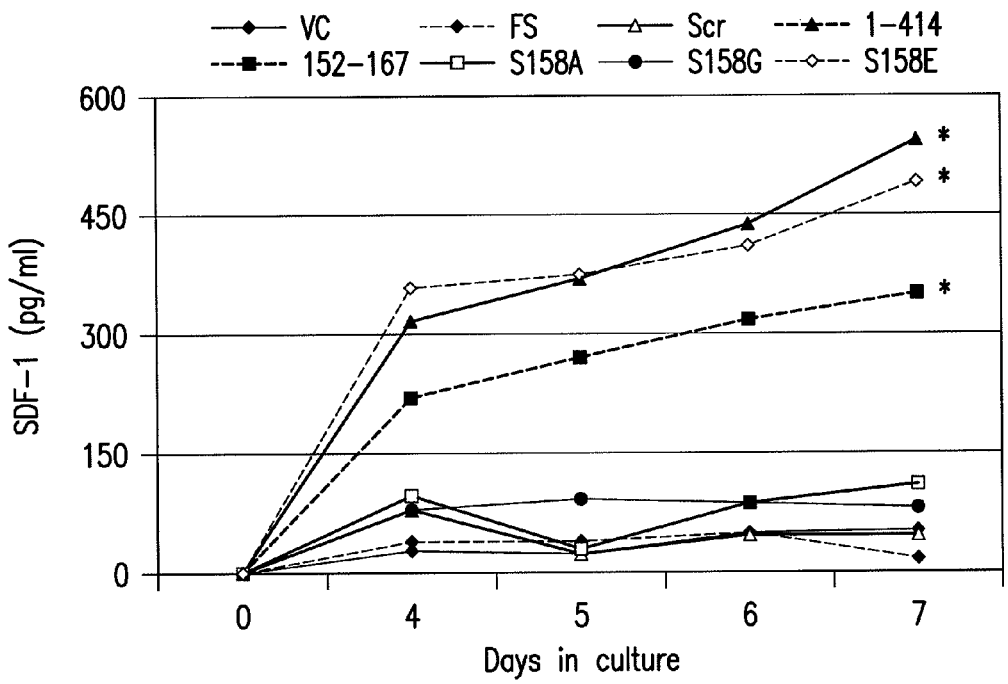

SDF-1 release into culture supernatants was induced in cells in which CXCR4 expression was diminished, including cell lines that express GBV-C NS5A amino acids 152-165, 152-167, and 152-181 (FIG. 29A) compared to the vector and frame-shift controls ($p<0.01$ for all three). Consistent with these findings, cells expressing the full-length NS5A (1-414), 152-167 and the S158E phosphomimetic mutant induced SDF-1 release compared to the cells expressing the vector control, the scrambled peptide, S158A, and S158G peptides and the frame-shift sequences (FIG. 29B; $p<0.02$ for all).

Example 4

HCV, GBV-C and other human flavivirus NS5A proteins interact and alter cellular pathways critical for HIV replication. Cellular based antiretroviral therapies can be developed by: (1) Fully characterize the structural requirements of the viral peptide necessary for HIV inhibition and/or CD4 regulation. (2) Identify the host cell protein(s) that interact with this NS5A peptide. (3) characterize the effects of NS5A structure on total cellular gene expression pathways. This information will determine which small molecules need to be synthesized to down-regulate CD4 and CXCR4, and upregulate SDF-1. Given the importance of CD4 and Th cytokines in HIV disease progression and also in other diseases including autoimmune and allergic diseases, further understanding of the effects of GBV-C and other flaviviruses on these cell receptors and cytokine pathways appear warranted. Of note, 3% of healthy U.S. blood donors have GBV-C viremia, and in developing countries, up to 17% of blood donors are GBV-C viremic. The overall effect of GBV-C on their natural host-cell (B and T lymphocytes) (George et al., 2003) may influence the course of more diseases than just HIV.

The structural requirements of the flavivirus NS5 peptides, and understanding how critical residues in NS5A interact with cells to lead to HIV inhibition will provide insight into HIV replication and lead to the discovery of small molecule inhibitors of HIV replication based on these characterized intracellular interactions.

GBV-C NS5A peptide analysis. The structure-function relationships between flavivirus NS5A interactions and HIV replication are determined using the minimal peptide sequence and the structure of the GBV-C NS5A peptide that results in HIV inhibition, and presumably CD4 down-regulation. This is repeated for HCV and Dengue. The initial experiments are very straightforward and use synthetic oligonucleotides to generate specific peptides in tet-off, GFP vector. These peptide-expressing plasmids are used to create stable cell lines expressing peptides that have sequentially deleted C- and N-terminal residues. Examples of peptides created include: 153-167 encoding DGIPVSWDADARAPA (SEQ ID NO:11), 154-167 GIPVSWDADARAPA (SEQ ID NO:12); 152-166 encoding VDGIPVSWDADARAP (SEQ ID NO:13), 152-165 VDGIPVSWDADARA (SEQ ID NO:14). Once clonal cell lines are selected that express GFP, the cell lines are tested for CD4 surface expression and HIV inhibition. To ensure that the peptide sequence is correct, cellular DNA is extracted that spans the insert between the CMV promoter and the EMC IRES as described (Xiang et al., 2006) and the sequence confirmed. Based on the predicted secondary structure analysis, if the effect requires the beta sheet predicted to be present in the 16-mer, removal of the N-terminal VDG will completely abolish the structure. However, 4 amino acids (RAPA) can be removed from the C terminus and maintain the beta sheet (and preserve the serine phosphorylation site). After definition, the minimal peptide can be synthesized and tested for activity when added exogenously to cells.

Additional flavivirus NS5 proteins. To further understand the structural and phosphorylation requirements of the flavivirus NS5 protein, the HCV peptide is characterized as was done for the GBV-C peptide. The tyrosine at position 161 is mutated to an alanine, glycine, glutamic acid or aspartic acid as done with the serine in the GBV-C peptide. In addition, N- and C-terminal deletion mutants are generated. Alignments of Dengue NS5 protein suggest an area of NS5 homology in the region of amino acid 129-160, including two serines. The Dengue NS5 protein is much larger than the pesti- and hepacivirus NS5A proteins (586 amino acids) and includes the polymerase at the C-terminal portion of the protein. Mapping of the region is performed as described for GBV-C and HCV. Vaccine strain (17D) of yellow fever virus and is used to amplify the NS5 coding region for testing this virus to see if it shares the functions of Dengue, HCV and GBV-C. Replication kinetics were good, with high titer virus released into culture supernatants within 3 days post-infection. The NS5A is amplified from the YFV isolate and is inserted into Jurkat cells as with GBV-C, GBV-B, HCV, and dengue virus. If YFV NS5A inhibits HIV as predicted, the inventors will be able to use these primary and transformed CD4+ T cell systems to serve as a robust, flavivirus-HIV co-infection model.

Structural analysis. NMR analysis is performed, and given the predictions that this peptide forms a beta sheet, there is reasonable likelihood that a structure will be detected by NMR. Peptides are purified by FPLC and a set of two dimensional, homonuclear NMR experiments are conducted using correlation spectroscopy (COSY), total correlation spectroscopy (TOCSY), and nuclear Overhauser effect spectroscopy (NOESY). The small size of the NS5A peptide decreases the likelihood that there is significant overlap between peaks, and increases the possibility of using homonuclear NMR to solve this structure. If overlaps are identified using the unlabeled peptide, nitrogen-15 and carbon-13 labeled peptides will be obtained to resolve these overlaps (as these will allow an additional proton dimension for the TOCSY and NOESY evaluations). When the structure is solved, the peptide is investigated with the native serine residue instead of the glutamic acid. Peptides are synthesized with the serine with and without a phosphate and repeat the NMR experiments to determine the role of phosphorylation of this peptide and the structure of the peptide. Based on the results of the HCV mapping experiments above, the Dengue NS5 is studied using similar approaches to assess the structure of these peptides. Alternative approaches may use circular dichroism, X-ray crystallography and the like.

The feature of these flavivirus proteins that leads to HIV inhibition likely involves phosphorylation or a structural mimetic. The smaller the size of the peptide required, the more likely these findings are able to be translated into a small molecule therapeutic or peptide mimetic. The data from these studies should clarify the phosphorylation requirement and size requirement of the peptide.

Example 5

Jurkat cells that have the RNA contained in the inhibitory NS5A construct, but in which the frame-shift results in the absence of NS5A protein expression proves that the NS5A protein (peptide) is responsible for the effect, and that it is not the result of an RNA structure binding to intracellular protein (e.g., TLR) or inducing IFN production. Thus, it is reasonable to hypothesize that the 16-amino acid region in NS5A interacts with an intracellular protein, and that this interaction either directly inhibits HIV replication or interferes with cellular pathways required for HIV replication. The inventors contemplate the identification of proteins that interact specifically with the 16 amino acid NS5A peptide. This approach will identify cellular proteins involved in HIV replication and/or inhibition. Identification of cellular binding partner(s) will lead to the development of structural studies to pursue the development of small molecule HIV inhibitors based on NS5A-cell interactions.

Yeast 2-hybrid technology can also be used as the primary means of identifying cellular proteins that interact with the GBV-C NS5A protein. Peptide pull-down experiments can be used to identify interacting polypeptides. The inventors know that the 16 amino acid peptide (152-167) inhibits HIV and down-regulates CD4, and that the serine residue at position 158 is critical for this function. Peptides are incubated with avidin-agarose beads in a 50% slurry, and cells are lysed using one of several potential lysis buffers (e.g., 1% NP-40 in 50 mM Tris (pH 8.0), 10% glycerol, 0.1 mM EDTA, 150 mM NaCl, 100 μM Na3V04, 50 mM NaF, 1 mM DTT, 0.4 mM PMSF, 1 μg/ml leupeptin, 3 μg/ml aprotinin, and 2 μg/ml pepstatin). Cellular protein lysates are pre-cleared by first incubating them with beads containing the S158A peptide, which should remove nonspecifically interacting proteins. The cleared lysates are then incubated with the S158E coated agarose beads. Interacting proteins are released by incubation of the beads in SDS sample buffer and boiling. Interacting proteins are identified by three methods. Phosphoproteins are detected by performing immunoblot analysis using anti-phosphotyrosine, anti-phosphoserine, and anti-phosphothreonine antibodies as previously described (Xiang et al., 2005). To determine if identified proteins have kinase activity, the inventors will test them for "in-gel" kinase assay (e.g., Kashiwadad et al., 2006). Alternatively, proteins are purified from SDS-PAGE and sent to the protein core facility for mass spectroscopy analysis and if necessary, N-terminal sequence analysis.

For interactions to be physiologically meaningful, binding proteins have to at least partially colocalize with the NS5A peptide. The system in which these studies is carried out depends upon the generation of antibodies to the NS5A peptide.

Most likely, interacting proteins will require purification and sequencing or mass spectroscopy for identification. It may be necessary to analyze eluates by 2-D gel electrophoresis to find out if single bands are comprised of a multiple proteins, in which case further purification is necessary. Eluates from large-scale purifications are subjected to gel electrophoresis and transferred to a PVDF membrane, followed by Coomassie blue staining. After excising the band of interest, direct sequencing by Edman degradation or peptide analysis by mass spectrometry is performed. In the likely event that the N terminus of the protein is blocked, internal sequence will be obtained by: (1) trypsin digestion of the blotted protein, followed by elution and HPLC separation of peptides, (2) partial digestion of the protein in gel slices with Endoprotease Glu-C or Arg-C followed by gel separation of fragments and transfer to PVDF, or (3) cyanogen bromide cleavage of the blotted protein followed by an additional round of gel separation/transfer (Liu and Fisher, 2004; Strack and Jacklet, 1993). cDNAs of unknown proteins is isolated by RT-PCR with degenerate oligonucleotides and cDNA library screening. cDNAs of known proteins is obtained from colleagues or EST repositories or cloned by RT-PCR/library screening. The identity of the deduced gene product with the affinity-purified protein is confirmed by immunoblotting the latter with antibodies raised against the gene product. Further confirmation is obtained from cell transfection studies.

Finally, to confirm a role for these interacting proteins in HIV replication inhibition, once identified, the genes are knocked down in NS5A expressing Jurkat cells using siRNA (using Qiagen SiRNA lentivirus vectors). After this gene(s) has been inhibited, the cells are infected with HIV in order to determine if the inhibitory effect of NS5A is abolished. Scrambled siRNA controls are used to insure specificity in the knockdown of the cellular genes. If knockdown of a gene abolishes HIV inhibition in NS5A cells, this will indicate that the gene is directly involved in the inhibitory effect.

Direct pull-down experiments will provide a limited number of potentially interacting proteins. The validation experiments will determine if the protein identified is required for NS5A peptide inhibition of HIV. The interaction of this protein(s) with the full-length NS5A and with the other flavivirus NS5 proteins will be assessed.

It is possible that the protein is part of a complex, and only a part of the complex can be identified by the pull-down experiments. In this case, the inventors will need to test more lysis conditions, perform additional pull-down and co-immunoprecipitation experiments.

Figure 18:
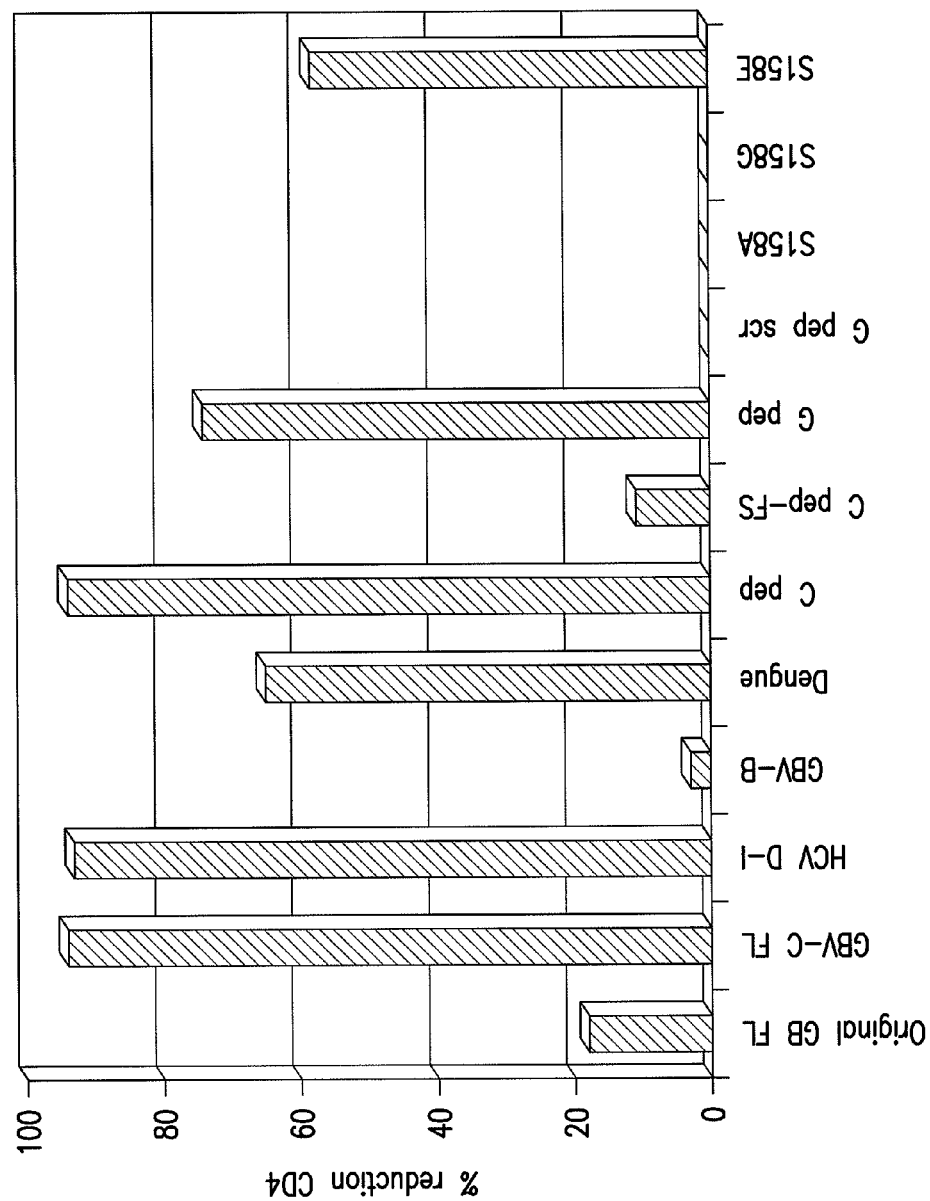
FIG. 18. CD4 measured by flow cytometry. Percent reduction in mean fluorescent intensity (MFI) of CD4 on cells. The original high passage GBV-C NS5A expressing Jurkat cells (with little protein expression by western blot; GB FL), a newly selected GBV-C FL cell line, HCV domain I (D-I), GBV-B and Dengue virus NS5 protein. C pep=HCV NS5A peptide (152-172), G pep=GBV-C 152-167, scr=scrambled peptide, S158A=alanine substituted for serine at amino acid 158, etc. All data have been re-produced in at least one additional experiment. HIV replication is inhibited in all cell lines in which CD4 expression is reduced by more than 10%.

Putative cellular interactor proteins is verified by immune precipitation, and different human protein libraries is compared in the yeast system to determine if there are cell-specific factors (e.g., hepatocyte, lymphocyte, etc.). Findings in the yeast system is confirmed in mammalian cells. For initial experiments, the S158E NS5A peptide is studied, and specificity for HIV inhibition is assessed by comparison with either the scrambled peptide, or the S158A mutant (FIG. 18 and Xiang et al., 2006). The inventors will use the Clontech Yeast Two-Hybrid Protein Interaction assay to determine which cellular proteins interact with the NS5A peptide. Briefly, this system utilizes the protein (peptide) of interest (GBV-C NS5A) as "bait". This peptide is fused to a DNA binding domain (DNA BD; the first 147 amino acids) of the GAL4 protein. The yeast is co-transfected with a commercial cDNA library fused to the activation Domain (AD), which is amino acids 768-881 of the GAL4 protein that functions as a transcriptional activator. In order for this activation to work, both the BD and AD domains have to be in close proximity. If the bait protein (NS5A peptide) interacts with a library protein, the DNA-BD and AD in turn bind to the galactose UAS, activate the galactose promoter, and activate transcription of the reporter gene (lacZ), and cells can be selected by X-gal. Absence of reporter activation by the bait alone is assayed as failure to grow on bait-prey interaction-selective plates and a negative β-Gal assay. In addition to the positive selection with for β-galactosidase, the yeast also requires histidine and ADE2 for growth. Both His3 and ADE2 expression are also under the control of two different Gal promoter. Thus, three independent selection genes are used to increase the stringency of the system. The S158E NS5A peptide (that inhibits HIV replication) is the initial region examined using the methods recommended by the manufacturer. Briefly, after testing for autonomous activation with yeast proteins, the titered (and amplified) Ad/library (human lymphocyte) is transformed, and transformants are selected using high (SD/-Ade/-His/-Lue/-Trp/X-α-gal), medium (SD/-His/-Leu/-Trp), or low stringency (SD/-Leu/-Trp). Transformants that are selected will have the protein interactions verified by repeat screening, and potential interacting proteins are identified by sequencing the "target" protein (using primers flanking the insert in the AD/library) in viable colonies. All putative proteins identified by sequencing are examined for protein expression by immune precipitation. This is facilitated by the presence of c-Myc and hemagglutinin tags in the GAL4 fusions in the Bait and Library plasmids respectively. In addition Clontech has commercial antibodies to the AD and BD regions.

Due to problems with colorimetric reporter assays resulting in false positives, chemiluminescent assays are used to measure β-Gal (Galacto-Star, Tropix) activities in lysates of liquid cultures and clones are further analyzed in groups of similar β-Gal activities to facilitate elimination of duplicates. To eliminate duplicate cDNAs, plasmid inserts are PCR amplified from yeast lysates and "finger-printed" by restriction digest with frequent cutters. Colonies harboring more than one library plasmid are segregated by repeatedly restreaking on plates without interaction selection until both β-Gal− and β-Gal+ colonies appear. Library plasmids are selectively recovered in bacteria utilizing selection and counterselection markers. Inserts are sequenced and identified by GenBank database searches. Library plasmids are cotransformed (or mated) with the original bait (S158E NS5A peptide) plasmid and negative controls (bait plasmid without insert or with the S158A-non-HIV inhibitory peptide), followed by nutritional selection and quantitative liquid β-Gal assays. Reciprocal co-immunoprecipitations with antibodies to epitope tags in the bait and prey vector to is performed. To determine if the binding partners are cell-specific, and/or if there are additional cellular proteins that interact with this 16-amino acid region on NS5A, at least two different commercial human cDNA libraries in the yeast system are tested (Clontech including "Human Bone Marrow Matchmaker cDNA Library, and human hepatocyte library).

Proteins identified in the yeast two-hybrid may bind directly to the NS5A peptide or require a third "bridging" protein. To test for direct interaction, a mixture of purified $His_6$-tag, MBP or GST-peptide fusion protein and interacting protein with a different fusion tag is precipitated with appropriate resins. Alternatively, the interacting protein is translated in vitro (using a coupled transcription/translation system) and copurified with NS5A fusion protein, or both interacting protein and epitope-tagged NS5A peptide is in vitro translated and coimmunoprecipitated with epitope tag antibodies. The T7 promoter present in common yeast two-hybrid and mammalian expression vectors facilitates this approach. The yeast two-hybrid method can detect low-affinity interactions that may not survive a standard immunoprecipitation protocol, but are nonetheless relevant if binding partners achieve high local concentrations. While the screen focuses on high-affinity interactions, weaker associations may be characterized as long as they display high specificity for the NS5A peptide. Demonstrating weak or transient interactions in vivo may necessitate immunodepletion or immunoprecipitation after reversible crosslinking.

Example 6

As noted above, some distinct differences between GBV-C NS5A and HCV NS5A full-length proteins have been identified, suggesting that there are virus-specific differences in the effects of NS5A on T lymphocyte gene expression. It is of interest to compare the effects of Dengue and/or YFV NS5 proteins with the HCV and GBV-C NS5A proteins for specific gene targets. SuperArrays can be used to examine, for example, three pathways (Chemokines, Th1,2,3, and Apoptosis related pathways) to map the specific region of viral protein that is involved in the regulation of cellular mRNAs of interest. There are at least 5 housekeeping genes in these arrays (actin, 18S rRNA, HPRT1, RPL13A and GAPDH) that are used for normalization. Each "pathway" includes real-time PCR primers and probes for 84 relevant genes (for example, chemokine kit includes [CCL] 1,11,13,15,16,17, 18, 19,2,3,4,5,7,8; CXC ligands [CXCL] 1,10,11,12,13,2,3, 5,6,9; CCR 1,2,3,4,5,6,7,8,10, CCRL1, CCRL2; BLR1, CXCR 3,4,6, CYFIP2) and the following chemokines and miscellaneous related genes: AGTRL1, BDNF, C5, C5R1 (GPR77), CCBP2, CKLF, CKLFSF1, CKLFSF2, CKLFSF3, CKLFSF4, CMKLR1, CSF3, CX3CL1, CX3CR1, ECGF1, GDF5, GPR31, GPR77, GPR81, HIF1A, IL-13, IL-16, IL-18, IL-1A, IL-4, IL-8, IL-8RA, LTB4R, MMP2, MMP7, MYD88, NFKB1, SCYE1, SDF2, SLIT2, TCP10, TLR2, TLR4, TNF, TNFRSF1A, TNFSF14, TREM1, VHL, XCL1, XCR1). The software accompanying the kit will perform T-tests for each gene, if provided ≧3 cycle threshold values for the sample and control experiments. 0.5-1.5 mg of sample and control RNA is utilized for the RT-PCR reaction and the product is amplified using the standard primer-probe set. A minimum of three independent RNA extractions are used for both the sample and control experiments. For validation, kinetics, and comparison with multiple RNA samples, the RNAs can be tested using the same primer-probe set (available individually from SuperArray, Inc.) by real-time PCR. Data is analyzed using the comparative Ct method ($\Delta\Delta C_T$) as outlined by Superarray (available on the world side web at superarray.com/PCRArrayPlate.php) and GEArray software, and the method has been validated (Lukaco et al., 2006; Perissi et al., 2004). Genes modulated by the HIV-inhibitory peptide that demonstrate a statistically significant ($p<0.05$) change compared to control are validated individually using real-time PCR, and RNA is compared from cells in log and stationary phase growth. Specific gene products for genes confirmed to be increased or decreased are assessed further for protein expression whenever possible, and because most of the 84 genes on each focused array are well characterized genes related to the pathway of interest, there are frequently commercial antibodies available for these gene products to allow further characterization. Specifically, surface expressed receptors (chemokine receptors) are assessed by flow cytometry (Xiang et al., 2001; Xiang et al., 2004), whereas western blot (normalizing for actin content) (Xiang et al., 2006a), IFA (Xiang et al., 2000) or confocal microscopy (Wunschmann et al., 2000) are used to compare protein expression and localization (and co-localization with NS5A) in NS5A and control cell lines. Chemokine release into culture supernatant is measured by ELISA as previously described (Xiang et al., 2004; Xiang et al., 2005). The functional significance of upregulated genes is assessed by siRNA knockdown in the Jurkat cells expressing the NS5A protein or fragment (and control cells) using Qiagen SiRNA lentivirus vectors to determine if they are involved in the HIV inhibition. After these genes have been inhibited, cells are infected with HIV in order to determine if the inhibitory effect of NS5A is abolished. Scrambled siRNA controls are also used to insure specificity in the knockdown of the cellular genes. If knockdown of a gene abolishes HIV inhibition in NS5A cells, this will indicate that the gene is directly involved in the inhibitory effect. Assessing the functionality of down-regulated genes is more difficult, but downregulation is assessed by knocking down the target genes with siRNA in the control cells, and testing HIV replication in these cells compared with cells transduced with a scrambled siRNA. If knockdown of these genes mimics the effect of the NS5A peptide, the genes (or gene products) are identified as critical for the NS5A inhibitory effect.

Clearly, if phosphorylation is required for HIV inhibition and downregulation of CD4, identification of the specific kinase responsible for phosphorylation is important to characterize (Macdonald and Harris, 2004). Several approaches can used, including knocking down putative kinases with siRNA, selecting candidate kinases based on data with HCV NS5A characterization or phosphoprotein proteomics (Macdonald and Harris, 2004; Schilling et al., 2006). Because there may be pathways or genes modulated by the NS5A peptide that are not included in the specific PCR arrays selected, for example, those testing for host cell restriction factors (e.g., APOBEC or Trim5-α), global gene expression profiling can be performed utilizing Affymetrix gene chips (U133 A and B). The basic approach is similar to that used for the PCR arrays, and validation using real-time RT-PCR for candidate genes, protein detection, SiRNA knockdown, and appropriate control cell lines is performed as described above and experiments are performed in at least quadruplicate. The inventors believe that understanding the effects of NS5 proteins on global lymphocyte gene expression may shed light on novel cellular pathways involved in HIV replication.

Example 7

Figure 19:
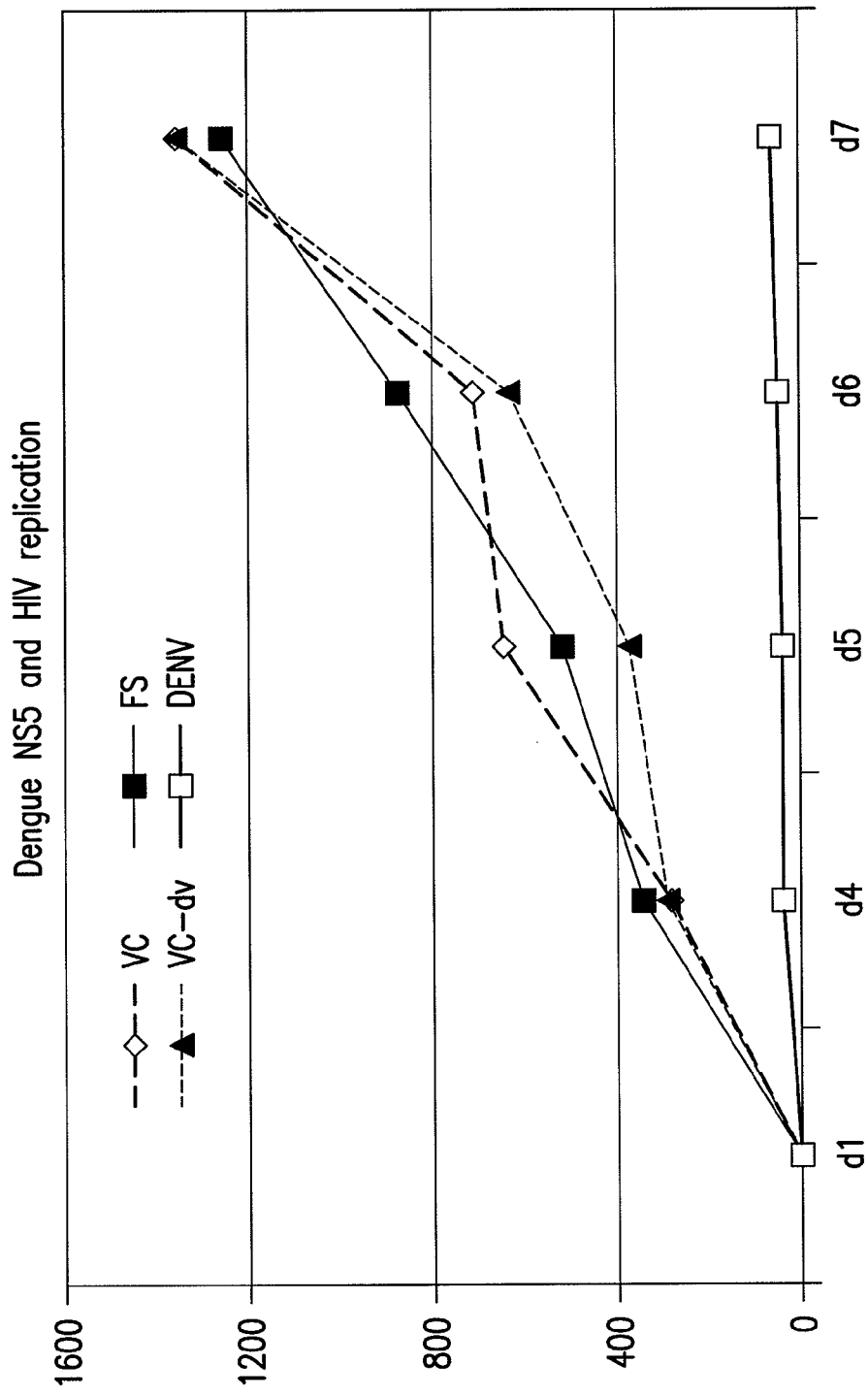
FIG. 19. Dengue NS5 and HIV replication. Jurkat cells expressing DENV NS5 are infected with HIV and replication measured at the indicated time points.
Figure 20:
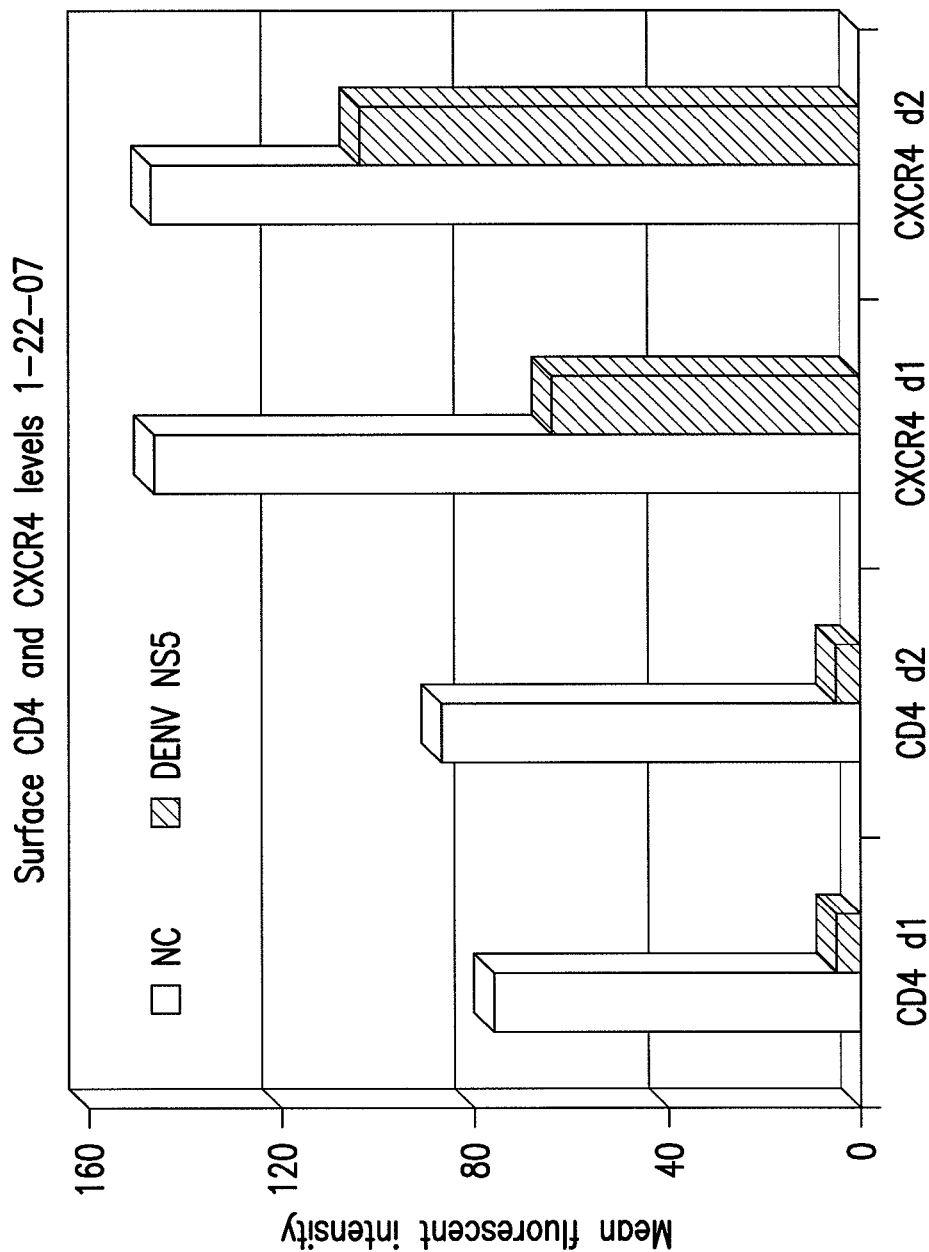
FIG. 20. Surface CD4 and CXCR4 levels. Experimental set up as in FIG. 19, where effect of DENV NS5 on cell surface expression is measured.

There are three genera within the family Flaviviridae. The "flavi" genera includes several human pathogens (for example: Dengue virus (DENV), Yellow Fever virus (YFV), West Nile virus (WNV)). The "pesti" genera contains only non-human animal viruses, whereas the "hepaci" genera includes GB virus C virus (GBV-C) and hepatitis C virus (HCV). To assess if the NS5 protein of DENV, YFV, and WNV also alters CD4+ T cells to make them less permissive for HIV replication, the inventors cloned the NS5 protein of these three viruses into the tet-off expression plasmid described above for the GBV-C and HCV NS5A proteins and mutants. Jurkat cell lines expressing DENV NS5 have been selected and characterized, and the DENV NS5 protein almost completely inhibits HIV replication in these cells (FIG. 19) similar to GBV-C and HCV. Thus, the NS5 protein of at least one member of the "flavi" genera shares the functional properties of the NS5A proteins of GBV-C and HCV. Jurkat cell lines with the WNV and YFV NS5 proteins are under construction, but it is anticipated that these will similarly demonstrate HIV inhibition. Mechanistically, the DENV NS5 protein also downregulates CD4 and CXCR4, both of which contribute to the HIV inhibition (FIG. 20). Because these HIV infections are done in transformed, CD4+ T cell lines, we have only been able to assess CXCR4-tropic HIV isolates.

Figure 21:
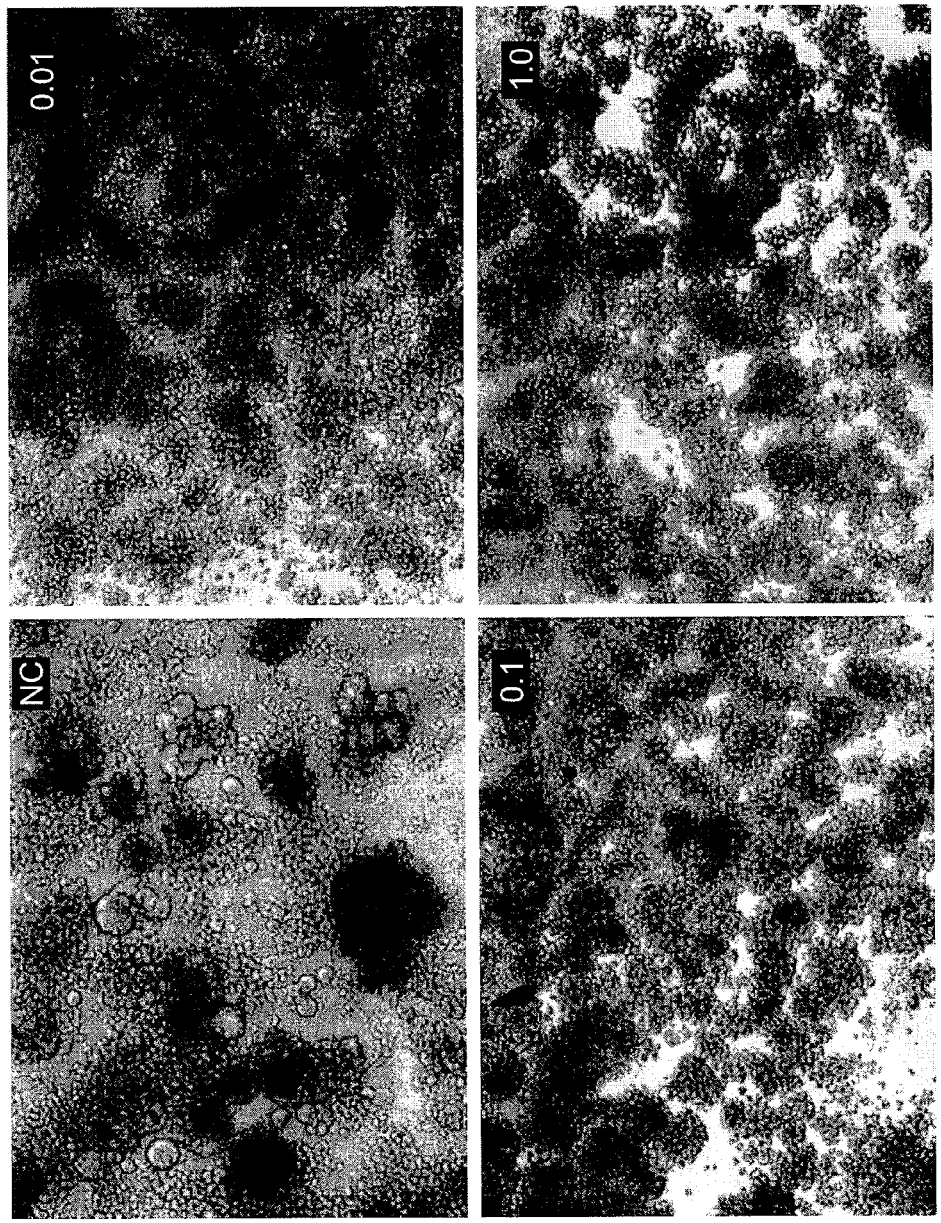
FIG. 21. Yellow fever virus (YFV) infection inhibits HIV replication in a human CD4+ T cell line (MT-2 cells). MT-2 cells ($2\times10^6$ cells) were infected with a media preparation (negative control=NC), or with vaccine strain YFV (strain 17D) at three different multiplicities of infection (MOI=0.01, 0.1 and 1.0). Cells were incubated 24 hrs prior to infection with a CXCR4-tropic HIV isolate (NIH AIDS Reference Reagent Program number 1073; 200 pg p24 Ag per 2 million cells) as previously described (Xiang et al., 2006). Four days after HIV infection, 4+ syncytia formation was observed in the negative control cells, whereas no syncytia were observed in any of the cells infected with YFV.
Figure 22A:
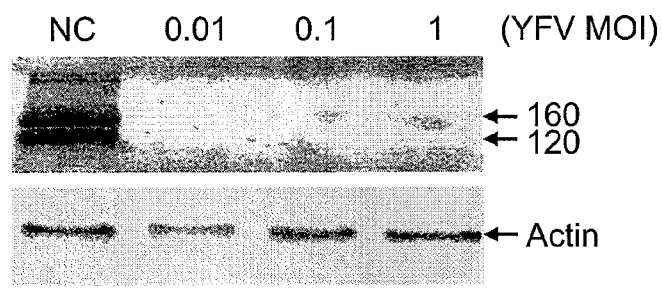
FIGS. 22A-B.
Figure 22:
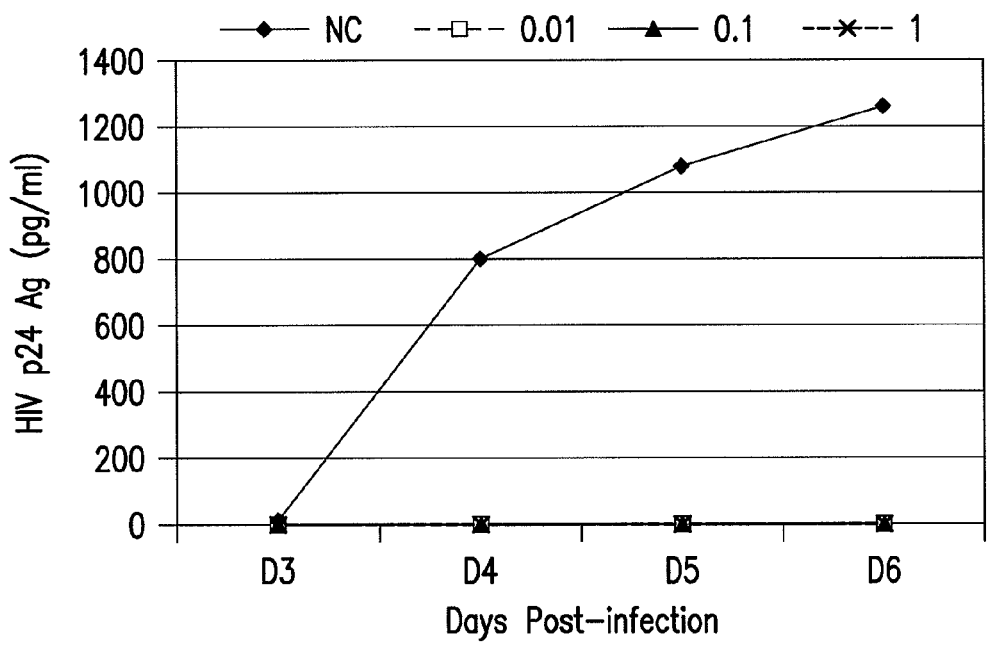
Figure 23A:
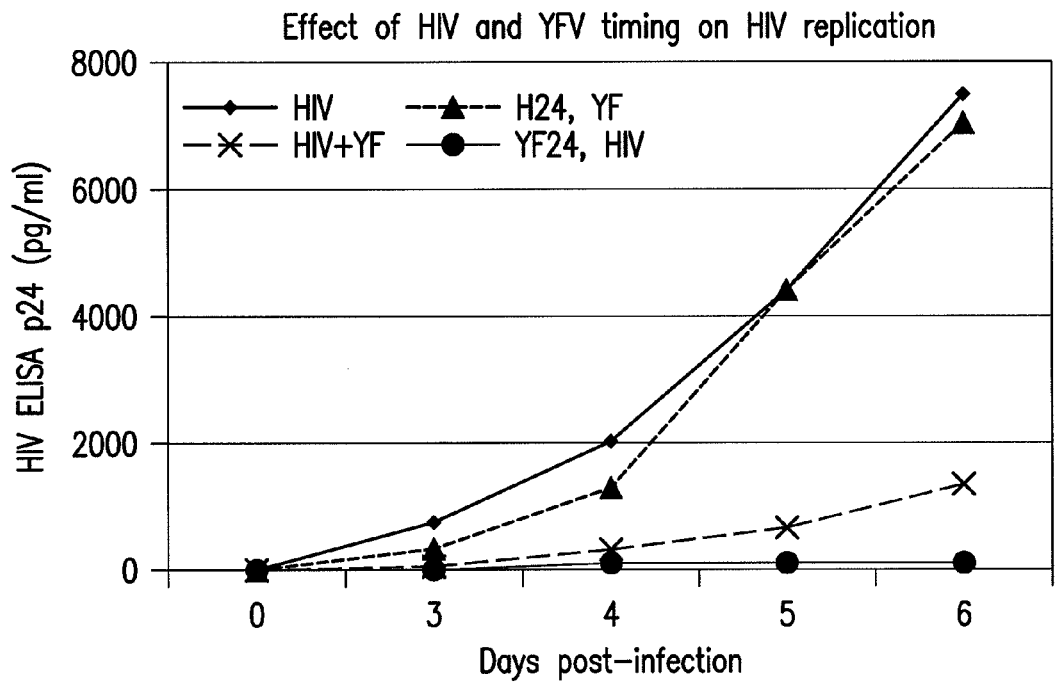
FIGS. 23A-B.
Figure 23B:
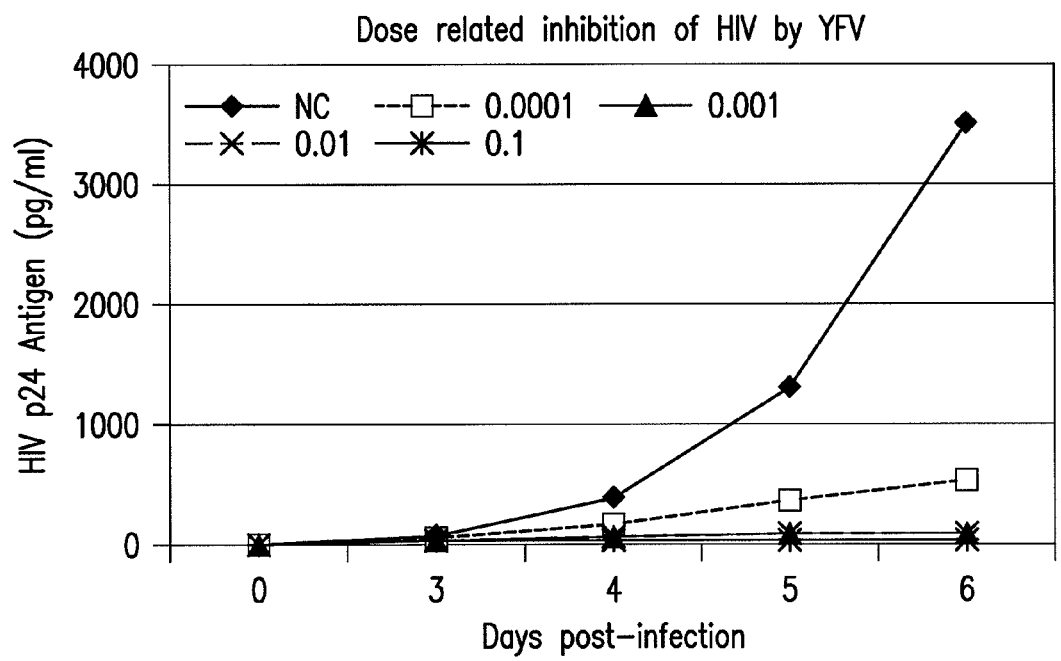

To assess another member of the "flavi" genera for HIV inhibitory function, and to determine if the effects of the NS5 protein are represented in a replicating virus system, the inventors next studied YFV. For biosafety reasons, all studies utilized the vaccine strain of YFV (strain 17D). Previous studies found that YFV can grow in human lymphocytes, so we tested YFV for growth in three human CD4+ T cell lines (Jurkat, MT-2, and CEM), and also in primary human peripheral blood mononuclear cells (PBMCs) and primary human CD4+ enriched T cells. A stock YFV preparation was made, and the infectious titer determined. MT-2 cells were mock-infected, or infected with YFV at varying multiplicities of infection (MOI), and 24 hrs later, the cells were infected with HIV (X4 isolate) as above. Because MT-2 cells are highly fusogenic with X4 HIV isolates, visible syncytia can be observed in HIV-infected cells. FIG. 21 illustrates that MT-2 cells infected by YFV did not exhibit syncytia 5 days following HIV infection, whereas large syncytia were observed in the mock-infected negative control cells (NC). FIG. 22A confirm this observation by showing nearly complete reduction in HIV protein expression (gp120/160) in cells infected with YFV compared to mock-infected cells, and FIG. 22B illustrates the replication curves as monitored by release of HIV p24 antigen into culture supernatants. When YFV was infected 24 hrs prior to, or simultaneously with HIV, inhibition was observed; however, if HIV infection was set up 24 hrs prior to YFV, no inhibition was observed, nor was YFV replication detected (FIG. 23A). The effect of YFV on HIV replication was dependent upon the YFV inoculum dose (FIG. 23B).

To determine if this inhibitory effect also occurs in primary human lymphocytes, PBMCs were infected with mock- or YFV-infected (MOI 1 and 0.1) and 24 hrs later were infected with either a CXCR4- or CCR5-tropic HIV isolate (as previously described, 200 pg p24 Ag). FIGS. 24A-B illustrate that YFV potently inhibited HIV replication (measured by p24 antigen production) for HIV isolates that utilize either CCR5 tropic (R5; FIG. 24A) or CXCR4 tropic (X4; FIG. 24B) isolates.

Example 8

Figure 30A:
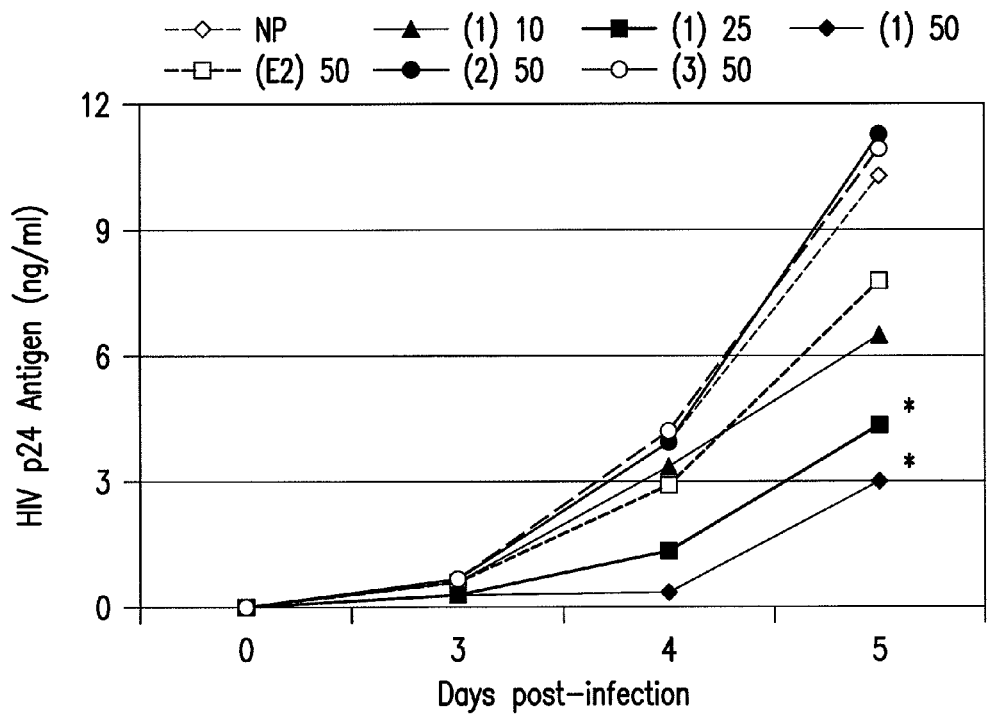

Synthetic GBV-C NS5A peptides inhibit HIV replication: Based on earlier data demonstrating that an 85 amino acid fragment within NS5A inhibits HIV replication (Xiang et al., 2006), overlapping peptides representing GBV-C NS5A amino acids 152-191, 172 to 211, and 197 to 236 were synthesized and tested for their ability to inhibit HIV when added to MT-2 or Jurkat cells. Incubation of cells with the peptide representing GBV-C NS5A amino acids 152-191 for 24 hrs prior to HIV infection, but not the two overlapping peptides or a control peptide, inhibited HIV replication in MT-2 cells in a dose-dependent manner (FIG. 30A). The peptides were added to MT-2 cells 24 hrs prior to HIV infection and maintained in the culture media in these experiments. Although the magnitude of HIV inhibition was less than that observed when the peptides were expressed within Jurkat cells, the inhibition was statistically significant ($p<0.01$ at 25 and 50 µg/ml).

Figure 30B:
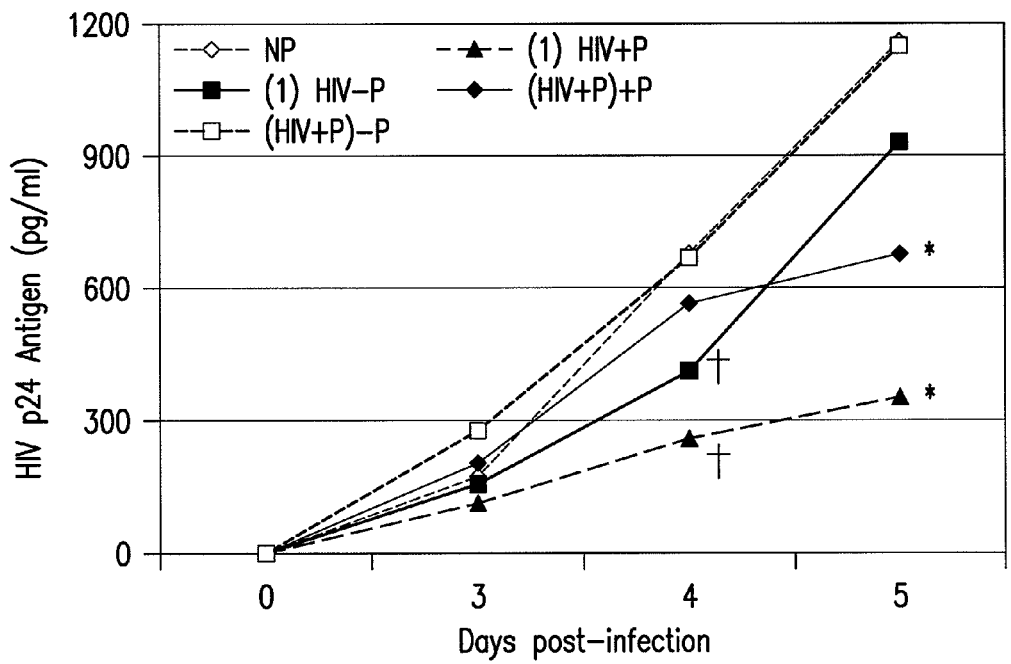

To determine if the timing of addition of peptides, or if the CD4+ cell substrate influenced the inhibitory effect, Jurkat cells were incubated with the inhibitory peptide (152-191) 24 hrs prior to HIV infection or at the time of HIV infection. Following HIV infection, cells were washed and incubated either with or without the peptide. Similar to the results observed using MT-2 cells (FIG. 30B), the Jurkat cells incubated with this peptide for 24 hrs prior to HIV infection demonstrated significantly less HIV replication than control cells during the first 4 days post infection, whether or not the peptide was maintained in the media (FIG. 30B). However, the inhibitory effect was lost by day 5 in cells maintained in media without peptide. In contrast, addition of peptides to cells at the time of HIV infection did not lead to significant differences in HIV replication from controls during the first 4 days post-infection. Nevertheless, cells maintained in peptide post-HIV infection demonstrated significantly less HIV release on day 5, presumably due to inhibition of cell-to-cell HIV spread (FIG. 30B).

Figure 27C:
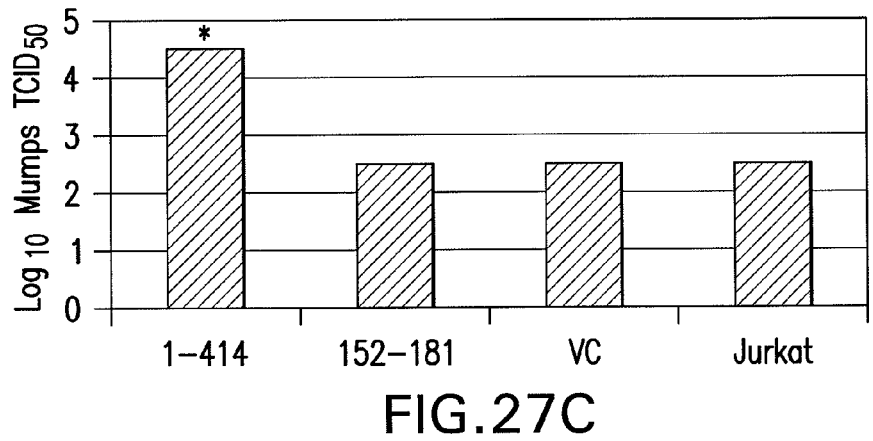
Figure 31A:
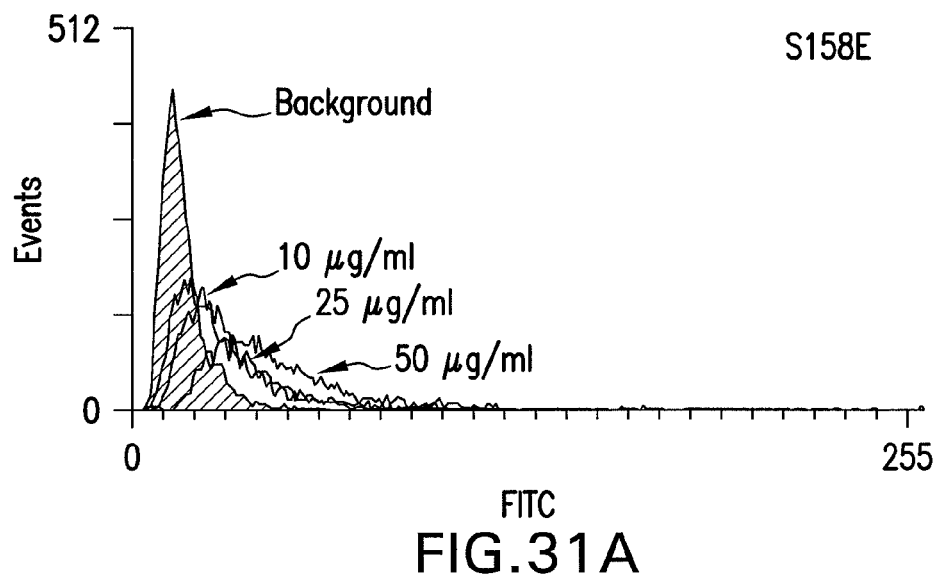
Figure 31B:
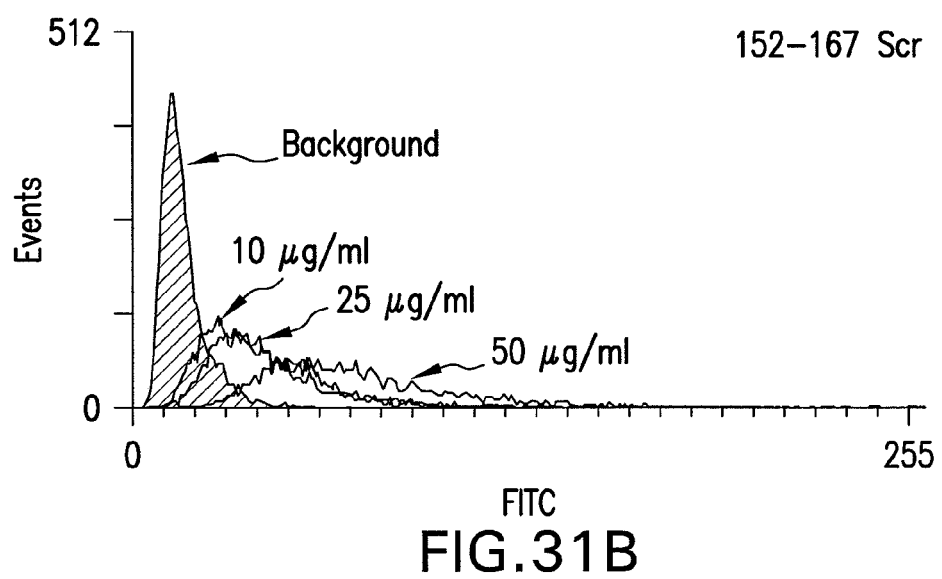
Figure 31C:
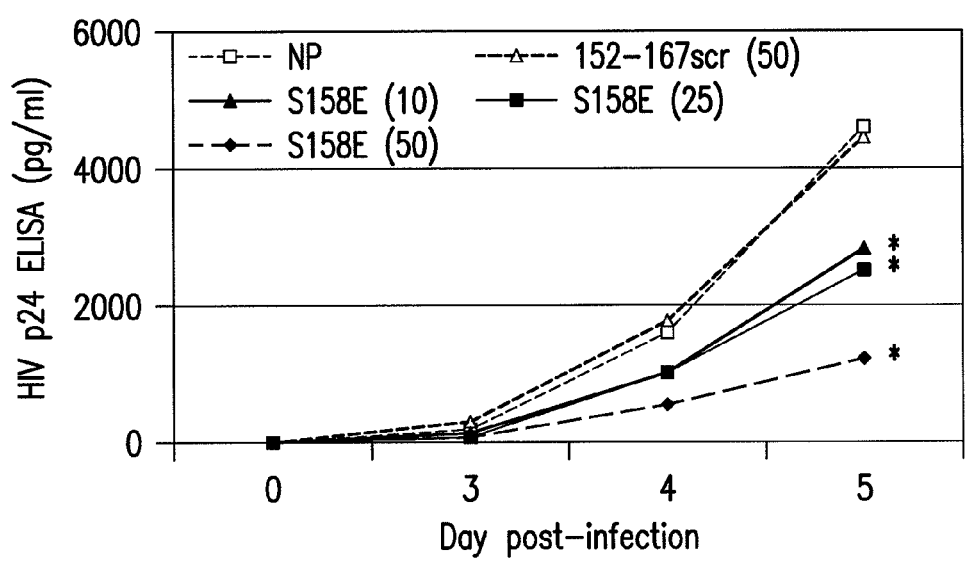

Based on the deletion mapping and mutagenesis data (FIG. 27), the active NS5A peptide mutant (S158E) and a control (152-167scr) peptide were synthesized and tested for HIV inhibition when added to cells 24 hrs prior to HIV infection (concentration up to 50 ug/mL). Neither peptide inhibited HIV replication (data not shown). To determine if this reflected poor uptake and/or degradation of the peptides, the S158E peptide and the scrambled 152-167 peptide were synthesized with an N-terminal Tat-protein-transduction domain to improve cellular uptake (Hermann et al., 2007), and the peptides were conjugated to FITC to allow monitoring of cellular binding and uptake. Both peptides were taken up by MT-2 cells in a dose-dependent manner (FIGS. 31A and B). Cells incubated in the S158E peptide inhibited HIV replication (FIG. 31C), albeit to a lesser extent than expression of the peptide within Jurkat cells (FIG. 26). In contrast, the 152-167scr peptide did not inhibit HIV (FIG. 31C), even though it's cellular uptake was similar to the S158E peptide (FIGS. 31A and B). No cellular toxicity or affect on viability was observed in MT-2 cells or Jurkat cells incubated in either of the peptides (50 ug/ml) as determined by cell counts, trypan blue exclusion, and MTT assay (Cederna et al., 2000; Xiang et al., 2001; Xiang et al., 2000) (data not shown).

Example 9

Materials and Methods

GBV-C NS5A proteins and peptides. The full length GBV-C NS5A protein coding sequences (numbering based on AF121950) were amplified from the plasma of individuals with GBV-C viremia, ligated into the pTRE2-Hyg plasmid (Clontech, Inc., Mountain View, Calif.) modified to include a stop codon after NS5A, followed by the EMC IRES element directing the translation of green fluorescent protein (GFP) as previously described (Xiang et al., 2006). GBV-C NS5A deletion or point mutants were generated in three ways, using convenient restriction sites, PCR mutagenesis, or using synthetic oligonucleotides to insert the desired sequence into the modified pTRE2-Hgy plasmid. All sequences were confirmed by automated fluorescent dye terminator cycle sequencing (University of Iowa DNA Core Facility; Applied Biosystems automated DNA sequencer 373A, Foster City, Calif.). Tet-Off Jurkat cells (Clontech, Inc.) were transfected (Amaxa nucleofection, Amaxa Inc., Gaithersburg, Md.) with plasmids containing NS5A sequences or with control sequences including the vector control expressing GFP, or with a vector that contains NS5A sequences with a single base insertion to create a frameshift mutation as previously described (Xiang et al., 2006). Following selection in hygromycin and neomycin (200 µg/ml each), clonal cell lines were prepared by at least two rounds of terminal dilution cloning.

To monitor NS5A expression, Jurkat cells were lysed in RIPA buffer containing protease and phosphatase inhibitors, clarified (13,000×g, 2 min and 4° C.), and subjected to SDS-PAGE prior to transfer to nitrocellulose membranes (Bio Rad, Inc., Hercules, Calif.) as previously described (Xiang et al., 2005). Immunoreactive proteins were identified using the GE3 anti-GBV-C NS5A rabbit serum kindly provided by Dr. Jungsuh Kim (Genelabs Technologies, Inc., Redwood City, Calif.) which was generated against GBV-C nucleotide sequences 6615-6977 expressed in *E. coli*. For cell lines expressing NS5A fragments not detected by immunoblot, expression of GFP was demonstrated by flow cytometry and total cellular DNA was examined for linkage between NS5A sequences and GFP using PCR followed by determination of the nucleotide sequence as previously described (Xiang et al., 2006). DNA sequence alignments and predicted protein secondary structure analyses employed DNAMan software (Lynnen Biosoft, Inc.).

Synthetic peptides representing NS5A amino acid sequences were either kindly provided by Dr. Opendra Sharma and the NIH Aids Reference Reagent Program or purchased (New England Peptide LLC 65 Zub Lane Gardener Mass. or Iowa State University Protein Facility, Ames, Iowa).

Virus infections. An HIV-1 isolate (X4, Glade B; NIH AIDS Research and Reference Reagent Program, catalog number 1073) was used to infect CD4+ T cell lines (Jurkat cells and Jurkat cells expressing GBV-C NS5A peptides or control plasmids, or MT-2 cells; 200 pg HIV p24 antigen per $10^6$ cells) as previously described (Wuenschmann and Stapleton, 2000).

Following HIV attachment, cells were washed, maintained in fresh media and culture supernatants were obtained at various time points to measure HIV-1 replication. HIV-1 replication was determined either by measuring HIV p24 antigen in pooled culture supernatants from three replicate infections (Retro-Tek HIV-1 p24 antigen ELISA kits, Zeptometrix, Buffalo, N.Y.) as previously described (Xiang et al., 2004; Xiang et al., 2001). All infections were performed in triplicate and were independently repeated at least twice with consistent results. The amount of HIV produced from cultured cells was estimated by calculating the HIV p24 antigen area under the curve (AUC) between successive time points (using the formula described by Trkola et al.: AUC=(HIV p24 antigen time 2−HIV p24 antigen time 1)×(Time 2 in days−Time 1 in days)/ ln(HIV p24 antigen time2/HIV p24 antigen time1) (George et al., 2006; Trkola et al., 2003).

Attenuated mumps virus (Jeryl-Lyn vaccine strain, Merck & Co.) was purchased and a stock virus preparation was generated. The infectious titer of this preparation was determined in Vero cells as described (Kenny et al., 1970).

The mumps virus preparation was used to infect Jurkat cells including cell lines that expressed GBV-C NS5A peptides or vector control cell lines.

Chemokines and chemokine receptors. CXCR4 and CCR5 expression on the surface of cells were determined by flow cytometry as previously described (Xiang et al., 2001). Polyclonal rabbit anti-CCR5 (FITC-conjugated) and anti-CXCR4 (PE-conjugated) antibodies (BD Pharmingen, San Jose, Calif.) were used in these studies. Flow cytometry was performed using a FACScan (Becton Dickenson, San Jose, Calif.). SDF-1, RANTES, MIP-1α and MIP-1β were detected in culture supernatant fluids by ELISA (R&D Systems, Minneapolis, Minn.) as previously described (Xiang et al., 2004).

Statistics. Statistics were performed using SigmaStat software V3.11 (Jandel Scientific, Chicago, Ill.). For individual timepoints, HIV p24 antigen release or infectious titer (mumps virus) were compared by T-tests. For all other results the AUC for experimental samples was compared to control samples using T-tests.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,554,101
U.S. Pat. No. 4,683,202
U.S. Pat. No. 4,833,077
U.S. Pat. No. 4,879,236
U.S. Pat. No. 5,582,981
U.S. Pat. No. 5,620,896
U.S. Pat. No. 5,650,298
U.S. Pat. No. 5,714,153
U.S. Pat. No. 5,871,986
U.S. Pat. No. 5,874,563
U.S. Pat. No. 5,925,565
U.S. Pat. No. 5,928,906
U.S. Pat. No. 5,935,819
U.S. Pat. No. 5,958,895
U.S. Pat. No. 6,004,799
U.S. Pat. No. 6,399,763
U.S. Pat. No. 6,479,243
PCT Appln. WO 01/77157
PCT Appln. PCT/US03/33925
PCT Appln. PCT/US2004/017706
Abe, *Japan. J. Infect. Dis.* 54:55-63, 2001.
Akiyoshi et al., *Am. J. Gastroenterol.*, 94:1627-1631, 1999.
Almendro, et al., *J. Immunol.*, 157(12):5411-21, 1996.
Alter, *Transfusion* 37:569-572, 1997.
Alter et al., *N. Engl. J. Med.*, 336:741-746, 1997a.
Alter et al., *N. Engl. J. Med.*, 336:747-754, 1997b.
Angel et al., *Cell*, 49:729, 1987b.
Angel et al., *Mol. Cell. Biol.*, 7:2256, 1987a.
Antonucci et al., 2005. Antiviral Ther. 10:109-117.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Avirutnan et al., 1998. J. Immunol. 161:6338-6346.
Bae et al., *J. Virol. Methods* 110:185-191, 2003.
Baichwal and Sugden, In: *Gene Transfer*, Kucherlapati (Ed.), NY, Plenum Press, 117-148, 1986.
Balfe et al., *AIDS Res. Hum. Retroviruses* 14, 1229-1234. 1998.
Banerji et al., *Cell*, 27(2 Pt 1):299-308, 1981.
Banerji et al., *Cell*, 33(3):729-740, 1983.
Barany and Merrifield, In: *The Peptides*, Gross and Meienhofer (Eds.), Academic Press, NY, 1-284, 1979.
Berkhout et al., *Cell*, 59:273-282, 1989.
Bica et al., *Clin. Infect. Dis.* 32:492-497, 2001.
Birk et al., *AIDS* 16:2482-2485, 2002.
Bisson et al., *AIDS* 19:1910-1912, 2005.
Bjorkman et al., *AIDS* 18:877-86, 2004.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Bukh et al., *Virol.* 262:470-478, 1999.
Bukh et al., *J. Inf. Dis.*, 177:855-862, 1998.
Bulla and Siddiqui, *J. Virol.*, 62:1437, 1986.
Burger et al., *Antimicrob Agents Chemother.*, 37(7):1426-31, 1993.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonell et al., *FEMS Microbiol. Lett.*, 177(1):75-82, 1999.
Celander and Haseltine, *J. Virology*, 61:269, 1987.
Celander et al., *J. Virology*, 62:1314, 1988.
Centers for Disease Control and Prevention (CDC). HIV/AIDS Surveillance Report 1999. 11 (no. 2), 1-44. 2000.
Chandler et al., *Cell*, 33:489, 1983.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell. Biol.*, 7:2745-2752, 1987.
Chen et al., *J. Virol.* 78:12107-12119, 2004.
Choi et al., *Cell*, 53:519, 1988.
Clark-Lewis et al., *J. Biol. Chem.*, 269:16075-16081, 1994.
Clegg et al., *AIDS* 14, 103-108, 2000.
Cocchi et al., *Science* 270:1811-1815, 1995.
Cocea, *Biotechniques*, 23(5):814-6, 1997.
Cohen et al., *J. Clin. Invest.* 100:1581-1589, 1997.
Cohen et al., *J. Cell. Physiol.*, 5:75, 1987.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
Dawson et al., *J. Med. Virol.* 50:97-103, 1996.
de Martino et al., *J. Infect. Dis.*, 178:862-865, 1998.
De Villiers et al., *Nature*, 312(5991):242-246, 1984.
Deacon et al., *Science* 270:988-991, 1995.

Deng et al., *Nature* 381:661-666, 1996.
Deschamps et al., *Science*, 230:1174-1177, 1985.
Dickens and Lemon, 1997. Hepatology 25:1285-1286.
Edbrooke et al., *Mol. Cell. Biol.*, 9:1908, 1989.
Edlund et al., *Science*, 230:912-916, 1985.
Enomoto et al., *J. Clin. Invest.* 96:224-230, 1995.
Fechheimer et al., *Proc. Nat'l Acad. Sci. USA*, 84:8463-8467, 1987.
Feng and Holland, *Nature*, 334:6178, 1988.
Feucht et al., *Hepatology*, 26:491-494, 1997.
Firak and Subramanian, *Mol. Cell. Biol.*, 6:3667, 1986.
Foecking and Hofstetter, *Gene*, 45(1):101-105, 1986.
Fogeda et al., *J. Virol.* 74:7936-7942, 2000.
Fogeda et al., *J. Virol.* 73:4052-4061, 1999.
Fraley et al., *Proc. Nat'l Acad. Sci. USA*, 76:3348-3352, 1979.
Freshney, In: *Animal Cell Culture: a Practical Approach*, 2$^{nd}$ Ed., Oxford/NY, IRL Press, Oxford University Press, 1992.
Fujita et al., *Cell*, 49:357, 1987.
Fultz et al., 2003. 1996. Conference on Retroviruses and Opportunistic Infections Boston:abstract 828.
Gabizon et al., *Cancer Res.*, 50(19):6371-6378, 1990.
Gale et al., *Mol. Cell. Biol.* 18:5208-5218, 1998.
Gale et al., *J. Virol.* 73:6506-6516, 1999.
Garcia et al., *J. Virol.* 79:9197-9205, 2005.
George et al., *Curr. Infect. Dis. Rep.* 4:550-558, 2002.
George et al., *Virology* 316:191-201, 2003.
George et al., *J. Infect. Dis.* 193:451-454, 2006.
Ghosh and Bachhawat, In: *Liver diseases, targeted diagnosis and therapy using specific receptors and ligands*, Wu and Wu (Eds.), NY, Marcel Dekker, 87-104, 1991.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Goodnough et al., *N. Engl. J. Med.* 340:438-447, 1999.
Gopal, *Mol. Cell. Biol.*, 5:1188-1190, 1985.
Gossen et al., *Proc. Nat'l Acad. Sci. USA*, 89:5547-5551, 1992.
Gossen et al., *Science*, 268:1766-69, 1995.
Graham and Van Der Eb, *Virology*, 52:456-467, 1973.
Greene et al., *Immunology Today*, 10:272, 1989
Greub et al., *Lancet* 356:1800-1805, 2001.
Grivel et al., *J. Infect. Dis.* 192:71-78, 2005.
Grosschedl and Baltimore, *Cell*, 41:885, 1985.
Haaskjold et al., *APMIS* 100:1123-1128, 1992.
Handelsman et al., Abstract 718. Conference on Retroviruses and Opportunistic Infections Denver: 309, 2006.
Harland and Weintraub, *J. Cell Biol.*, 101:1094-1099, 1985.
Haslinger and Karin, *Proc. Natl. Acad. Sci. USA*, 82:8572, 1985.
Hassoba et al., *J. Med. Virol.* 56:253-258, 1998.
Hauber and Cullen, *J. Virology*, 62:673, 1988.
Heim et al., *J. Virol.* 73:8469-8475, 1999.
Hen et al., *Nature*, 321:249, 1986.
Hensel et al., *Lymphokine Res.*, 8:347, 1989.
Heringlake et al., *J. Infect. Dis.* 177:1723-1726, 1998.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Hoofnagle, 1997. Hepatology 26:15 S-20S.
Horlick and Benfield, *Mol. Cell. Biol.*, 9:2396, 1989.
Huang et al., *Cell*, 27:245, 1981.
Huang et al., *Nature Med.*, 2:1240-1243, 1996.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jessie et al., *J. Infect. Dis.* 189:1411-1418, 2004.
Johnson et al., *Mol. Cell. Biol.*, 9:3393, 1989.
Jung and Reil, 13th International Meeting on Hepatitis C virus & related viruses Abstract number 679: Aug. 30, 2006.
Jung et al., *AIDS* 19:12567-1272, 2005.
Jung et al., Abstract 282. Conference on Retroviruses and Opportunistic Infections Denver: 141, 2006.
Jung et al., *AIDS* 21:645-647, 2007.
Kadesch and Berg, *Mol. Cell. Biol.*, 6:2593, 1986.
Kalbfleish and Prentice, The Statistical Analysis of Failure Time Data. Wiley, New York, 2002.
Kaneda et al., *Science*, 243:375-378, 1989.
Karin et al., *Mol. Cell. Biol.*, 7:606, 1987.
Kashiwadad et al., *J. Immunol.* 176:3958-3965, 2006.
Katinka et al., *Cell*, 20:393, 1980.
Kawamoto et al., *Mol. Cell. Biol.*, 8:267, 1988.
Kenny-Walsh et al., *N. Engl. J. Med.* 340:1228-1233, 1999.
Kiledjian et al., *Mol. Cell. Biol.*, 8:145, 1988.
Klamut et al., *Mol. Cell. Biol.*, 10:193, 1990.
Klinzman et al., GB virus C/hepatitis G virus: Does clearance of viremia differ based on mode of transmission? Jilbert A R, editor. Australian Center for Hepatitis Virology, Melbourne. 488-490, 2004.
Koch et al., *Mol. Cell. Biol.*, 9:303, 1989.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kyte and Doolittle, *J. Mol. Biol.*, 157:105-132, 1982.
Lareyre et al., *J. Bio. Chem.*, 274(12):8282-90, 1999.
Larios et al., *Arch. Biochem. Biophys.* 442:149-159, 2004.
Larios et al., *FEBS J.* 272:2456-2466, 2005.
Larsen et al., *Proc Nat'l Acad. Sci. USA.*, 83:8283, 1986.
Laskus et al., *J. Virol.*, 72:3072-3075. 1998.
Laspia et al., *Cell*, 59:283, 1989.
Latimer et al., *Mol. Cell. Biol.*, 10:760, 1990.
Law et al., *AIDS* 18:1169-1177, 2004.
Leary et al., *J. Med. Virol.*, 48:60-67. 1996.
Lee et al., *DNA Cell Biol.*, 16(11):1267-1275, 1997.
Lee et al., *Nature*, 294:228, 1981.
Lee et al., *Nucleic Acids Res.*, 12:4191-206, 1984.
Lefrère et al., *J. Infect. Dis.* 179:783-789, 1999.
Lefrère et al., *J. Infect. Dis.*, 179:783-789, 1999.
Levenson et al., *Hum. Gene Ther.*, 9(8):1233-6, 1998.
Levinson et al., *Nature*, 295:79, 1982.
Lin et al., *J. Virol.* 76:12242-12249, 2002.
Lin et al., *Mol. Cell. Biol.*, 10:850, 1990.
Lin et al., *Proc. Nat'l Acad. Sci. USA* 99, 15590-15595, 2002.
Lindenbach et al., *Science* 309:623-626, 2005.
Lindenbach et al., *Proc. Nat'l Acad. Sci. USA* 103:3805-3809, 2006.
Linnen et al., *Science*, 271:505-508. 1996.
Liu and Fisher, *J. Biol. Chem.* 279:14120-14128, 2004.

Lukaco et al., *Am. J. Pathol.* 109:977-986, 2006.
Luria et al., *EMBO J.,* 6:3307, 1987.
Lusky and Botchan, *Proc. Nat'l Acad. Sci. USA,* 83:3609, 1986.
Lusky et al., *Mol. Cell. Biol.,* 3:1108, 1983.
Macdonald and Harris, *J. Gen. Virol.* 85:2485-2502, 2004.
Macejak and Sarnow, *Nature,* 353:90-94, 1991.
Maciejewski et al., *J. Biol. Chem.* 46:27661-27665, 1995.
Majors and Varmus, *Proc. Natl. Acad. Sci. USA,* 80:5866, 1983.
Maniatis, et al., In: *Molecular Cloning,* A Laboratory Manual, Cold Spring Harbor Press, Cold Spring Harbor, N.Y., 1990.
Marks et al., *Bio/Technol.,* 10:779-783, 1992.
McNeall et al., *Gene,* 76:81, 1989.
McOmish et al., *J. Clin. Microbiol.* 32:884-892, 2006.
Medin et al., *J. Virol.* 79:11053-11061, 2005.
Merrifield, *Science,* 232: 341-347, 1986
Miksicek et al., *Cell,* 46:203, 1986.
Mordacq and Linzer, *Genes and Dev.,* 3:760, 1989.
Moreau et al., *Nucl. Acids Res.,* 9:6047, 1981.
Moss et al., *J. Infect. Dis.* 185:1035-1042, 2002.
Muesing et al., *Cell,* 48:691, 1987.
Nattermann et al., 2003. *AIDS* 17:1457-1462.
Nerurkar et al., *J. Med. Virol.,* 56:123-127, 1998.
Ng et al., *Nuc. Acids Res.,* 17:601, 1989.
Nicolas and Rubenstein, In: *Vectors: A survey of molecular cloning vectors and their uses,* Rodriguez and Denhardt (eds.), Stoneham: Butterworth, 493-513, 1988.
Nicolau and Sene, *Biochim. Biophys. Acta,* 721:185-190, 1982.
Niedrig et al., *Vaccine* 11:67-74, 1993.
Nomoto et al., *Gene,* 236(2):259-271, 1999.
Nousbaum et al., *J. Virol.* 74:9028-9038, 2000.
Nunnari et al., *Ann. Int. Med.* 139:26-30, 2003.
Okamoto et al., *J. Gen. Virol.* 78:737-745, 1997.
Ondek et al., *EMBO J.,* 6:1017, 1987.
Ornitz et al., *Mol. Cell. Biol.,* 7:3466, 1987.
Palmiter et al., *Nature,* 300:611, 1982.
Pawlotsky and Germanidis, 1999. J. Viral Hepat. 6:343-356.
Pech et al., *Mol. Cell. Biol.,* 9:396, 1989.
Pelletier and Sonenberg, *Nature,* 334(6180):320-325, 1988.
Penin et al., *Hepatology* 39:5-19, 2004.
Perez-Stable and Constantini, *Mol. Cell. Biol.,* 10:1116, 1990.
Perissi et al., *Cell* 116:511-526, 2004.
Perkins et al., Conference on Retroviruses and Opportunistic Infections Boston: 418 abstract 940, 2005.
Pessoa et al., *Hepatol.,* 27:877-880, 1998.
Picard and Schaffner, *Nature,* 307:83, 1984.
Pinkert et al., *Genes and Dev.,* 1:268, 1987.
Piroth et al., *J. Viral Hepat.* 7:302-308, 2000.
Polgreen et al., *Microbes and Infect.* 5:1255-1261, 2003.
Polyak et al., *J. Virol.* 75:6095-6106, 2001.
Polyak et al., *J. Virol.* 75:6209-6211, 2001.
Polyak, *Clin. Liver Dis.* 7:67-88, 2003.
Ponta et al., *Proc. Natl. Acad. Sci. USA,* 82:1020, 1985.
Porton et al., *Mol. Cell. Biol.,* 10:1076, 1990.
Potter et al., *Proc. Natl. Acad. Sci. USA,* 81:7161-7165, 1984.
Queen and Baltimore, *Cell,* 35:741, 1983.
Quinn et al., *Mol. Cell. Biol.,* 9:4713, 1989.
Radkowski et al., 2000. Transfusion Med. Rev. 95:3986-3989.
Redondo et al., *Science,* 247:1225, 1990.
Reisman and Rotter, *Mol. Cell. Biol.,* 9:3571, 1989.
Remington's Pharmaceutical Sciences, 18th Ed. Mack Printing Company, 1389-1404, 1990.
Report on the global HIV/AIDS epidemic: December 2000, UNAIDS.
Resendez Jr. et al., *Mol. Cell. Biol.,* 8:4579, 1988.
Rey et al., *Eur. J. Clin. Microbiol. Infect. Dis.* 19:721-724, 2000.
Reynes et al., *AIDS* 15, 1627-1634, 2001.
Ridgeway, In: *Vectors: A survey of molecular cloning vectors and their uses,* Rodriguez and Denhardt (Eds.), Stoneham: Butterworth, 467-492, 1988.
Ripe et al., *Mol. Cell. Biol.,* 9:2224, 1989.
Rippe et al., *Mol. Cell. Biol.,* 10:689-695, 1990.
Rittling et al., *Nuc. Acids Res.,* 17:1619, 1989.
Robertson et al., *Arch. Virol.,* 143:2493-2503, 1998.
Rodriguez et al., *J. Infect. Dis.* 187:504-507, 2003.
Rosen et al., *Cell,* 41:813, 1988.
Rossi et al., *JAMA* 288:241-243, 2002.
Rowland-Jones, *J. Infect.,* 38:67-70, 1999.
Sabin et al., *J. Acquir. Immune Defic. Syndr.,* 19:546-547, 1998.
Sakai et al., *Genes and Dev.,* 2:1144, 1988.
Sambrook et al., In: *Molecular cloning,* Cold Spring Harbor Laboratory Press, Cold Spring Harbor, N.Y., 2001.
Satake et al., *J. Virol.,* 62:970, 1988.
Scarlatti et al., *Nature Med.* 3:1259-1265, 1997.
Schaffner et al., *J. Mol. Biol.,* 201:81, 1988.
Schilling et al., *J. Biol. Chem.* 281:23686-23697, 2006.
Searle et al., *Mol. Cell. Biol.,* 5:1480, 1985.
Seeff et al., *Ann. Int. Med.* 132:105-111, 2000.
Seipp et al., *J. Hepatol.,* 30:570-579, 1999.
Sharp and Marciniak, *Cell,* 59:229, 1989.
Shaul and Ben-Levy, *EMBO J.,* 6:1913, 1987.
Sherman et al., *Mol. Cell. Biol.,* 9:50, 1989.
Shimizu, *J. Virol.,* 73:8411-8414, 1999.
Shor-Posner et al., *Am. J. Med.* 94:515-519, 1993.
Simons et al., *Nature Med.* 1:564-569, 1995.
Simons et al., *J. Virol.,* 70:6126-6135. 1996.
Simons et al., *Nature Med.,* 1:564-569, 1995a.
Simons et al., *Proc. Nat'l Acad. Sci. USA,* 92:3401-3405, 1995b.
Sleigh and Lockett, *J. EMBO,* 4:3831, 1985.
Smith et al., *Science* 277:959-965, 1997.
Souza et al., *HIV Med.* 7:25-31, 2006.
Spalholz et al., *Cell,* 42:183, 1985.
Spandau and Lee, *J. Virology,* 62:427, 1988.
Spandidos and Wilkie, *EMBO J.,* 2:1193, 1983.
Stapleton et al., *J. Clin. Microbiol.* 42:3915-3919, 2004.
Stapleton et al., Evidence for delayed human immunodeficiency virus (HIV) disease progression in HIV-GB virus C co-infected individuals. In Viral Hepatitis and Liver Disease. H. Margolis and Fields, H. A., editors. Lipincott, London. 2004.
Stapleton et al., *J. Infect. Dis.* 191:2157-2158, 2005.
Stapleton, *Semin. Liver Dis.* 23:137-148, 2003.
Stephens and Hentschel, *Biochem. J.,* 248:1, 1987.
Stewart and Young, In: *Solid Phase Peptide Synthesis,* 2d. ed., Pierce Chemical Co., 1984.
Strack and Jacklet, *J. Neurobiol.* 24:552-570, 1993.
Stuart et al., *Nature,* 317:828, 1985.
Sulkowski et al., *JAMA* 288:199-206, 2002.
Sullivan and Peterlin, *Mol. Cell. Biol.,* 7:3315, 1987.
Swartzendruber and Lehman, *J. Cell. Physiology,* 85:179, 1975.
Tacke et al., *Hepatol.,* 26:1626-1633, 1997.
Takebe et al., *Mol. Cell. Biol.,* 8:466, 1988.
Tam et al., *J. Am. Chem. Soc.,* 105:6442, 1983.
Tan and Katze, *Virol.* 284:1-12, 2001.
Tanaka et al., *Ann. Intern. Med.* 125:740-743, 1996.
Tanaka et al., *J. Viral Hepat.* 5:153-159, 1998.
Tanaka et al., *J. Hepatol.,* 27:1110-1112, 1997.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.

Tellinghuisen et al., *J. Biol. Chem.* 279:48576-48587, 2004.
Temin, In: *Gene Transfer*, Kucherlapati (ed.), NY: Plenum Press, 149-188, 1986.
Thiesen et al., *J. Virology*, 62:614, 1988.
Thomas et al., *J. Infect. Dis.*, 177:539-542, 1998.
Tillmann and Manns, *Antiviral Res.* 52:83-90, 2001.
Tillmann et al., *Hepatology* 28:379-384, 1998.
Tillmann et al., 7th International Meeting on Hepatitis C and Related Viruses. Gold Coast, Australia. Dec. 3-7, 2000, p. 311, Abstract P172.
Tillmann et al., *N. Engl. J. Med.* 345:715-724, 2001.
Toyoda et al., *J. Acquir. Immune Defic. Syndr.*, 17:209-213, 1998.
Treisman, *Cell*, 42:889, 1985.
Tronche et al., *Mol. Biol. Med.*, 7:173, 1990.
Trudel and Constantini, *Genes and Dev.*, 6:954, 1987.
Tsumaki et al., *J. Biol. Chem.*, 273(36):22861-22864, 1998.
Tur-Kaspa et al., *Mol. Cell. Biol.*, 6:716-718, 1986.
Tyndell et al., *Nuc. Acids. Res.*, 9:6231, 1981.
Van der Bij et al., *J. Infect. Dis.* 191:2158-2160, 2005.
Van der Bij et al., *J. Infect. Dis.* 191:678-85, 2005.
Vannice and Levinson, *J. Virology*, 62:1305, 1988.
Vasseur et al., *Proc Nat'l Acad. Sci. USA,* 77:1068, 1980.
Voirin et al., Conference on Retroviruses and Opportunistic Infections Seattle, 2002.
Wakita et al., *Nature Med.* 11:791-796, 2005.
Wang and Calame, *Cell*, 47:241, 1986.
Watt et al., *Clin. Infect. Dis.* 36:1067-1069, 2003.
Weber et al., *Cell*, 36:983, 1984.
Weinberger et al. *Mol. Cell. Biol.*, 8:988, 1984.
Wen et al., *J. Med. Virol.* 72:230-240, 2004.
Williams et al., *N. Engl. J. Med.* 350:981-90, 2004.
Winoto and Baltimore, *Cell*, 59:649, 1989.
Winter et al., *J. Infect. Dis.* 190:1618-1626, 2004.
Wright et al., *Hepatol.* 20:1152-1155, 1994.
Wu and Wu, *Biochem.*, 27:887-892, 1988.
Wu and Wu, *J. Biol. Chem.*, 262:4429-4432, 1987.
Wu et al., *Biochem. Biophys. Res. Commun.*, 233(1):221-6, 1997.
Wu et al., *J. Med. Virol.*, 52:83-85. 1997.
Wunschmann et al., *J. Virol.* 74:10055-10062, 2000.
Xiang et al., In vitro replication of a GB virus C infectious clone. In Viral Hepatitis and Liver Disease. H. S. Margolis and Fields, H. A., editors. Lipincott, London, 2000.
Xiang et al., *J. Virol.* 74:9125-9133, 2000.
Xiang et al., *N. Engl. J. Med.* 345:707-714, 2001.
Xiang et al., *Lancet* 363:2040-2046, 2004.
Xiang et al., *J. Infect. Dis.* 192:2147-2151, 2005.
Xiang et al., *J. Interferon Cytokine Res.* 25:261-270, 2005.
Xiang et al., *Proc. Nat'l Acad. Sci. USA* 103:15570-15575, 2006.
Xiang et al., *J. Interferon Cytokine Res.*, 25:261-70, 2005.
Xiang et al., *J. Viral Hepat.*, 6:S16-S22, 1999.
Yang et al., *Proc. Natl. Acad. Sci. USA,* 87:9568-9572, 1990.
Yeo et al., *Ann. Intern. Med.* 132:959-963, 2000.
Yutzey et al., *Mol. Cell. Biol.*, 9:1397, 1989.
Zhang et al., *HIV Med.*, 7:173-80, 2006.
Zhao-Emonet et al., *Biochim. Biophys. Acta*, 1442(2-3):109-19, 1998.
Zhong et al., *Proc. Nat'l Acad. Sci. USA*, 102:9294-9299, 2005.

---

The invention claimed is:

1. A pharmaceutical composition comprising an isolated peptide comprising at most 80 contiguous amino acids of NS5A, wherein the peptide comprises the amino acid sequence of VDGIPV(S/E)WDA(D/E)ARAPA) (SEQ ID NO: 24) or (V/L)DG(I/V)X(S/H)(W/R)XA(D/P)XXXPX (SEQ ID NO: 25), wherein X is any amino acid.

2. The composition of claim 1, comprising two or more peptides and/or peptide mimetics.

3. The composition of claim 1, wherein the peptide is a fusion peptide.

4. The composition of claim 3, wherein the fusion peptide includes a targeting domain.

5. The composition of claim 4, wherein the targeting domain targets the endoplasmic reticulum.

6. The composition of claim 4, wherein the targeting domain targets a cell surface receptor.

7. The composition of claim 6, wherein the cell surface receptor is the CD4 receptor.

8. The composition of claim 1, wherein the peptide is formulated in a lipid vehicle.

9. The composition of claim 8, wherein the lipid vehicle is a liposome.

10. The composition of claim 1, wherein the peptide is formulated with an amphipathic peptide, an insect peptide, or pyrrhocoricin.

11. The composition of claim 1, wherein the peptide comprises residues 152-167 of GBV-C NS5A, or the corresponding sequences from other flavivirus NS5A proteins.

12. A method for treating HIV infection comprising administering to a subject a composition comprising an isolated peptide comprising at most 80 contiguous amino acids of NS5A, wherein the peptide comprises an amino acid sequence VDGIPV(S/E)WDA(D/E)ARAPA (SEQ ID NO: 24) or (V/L)DG(I/V)X(S/H)(W/R)XA(D/P)XXXPX (SEQ ID NO: 25), wherein X is any amino acid.

13. The method of claim 12, wherein the peptide is a GBV-C NS5A peptide.

14. The method of claim 12, further comprising administration of at least a second anti-HIV therapy.

15. The method of claim 12, wherein the composition is administered at least twice.

16. A method for treating HIV infection comprising administering to a subject a composition comprising an expression construct encoding a peptide comprising at most 80 contiguous amino acids of NS5A, wherein said peptide comprises an amino acid sequence of VDGIPV(S/E)WDA(D/E)ARAPA (SEQ ID NO: 24) or (V/L)DG(I/V)X(S/H)(W/R)XA(D/P)XXXPX (SEQ ID NO: 25), wherein X is any amino acid.

17. The method of claim 16, wherein the peptide further comprises a targeting domain.

18. The method of claim 17, wherein the targeting domain targets a cell surface receptor.

19. A method for modulating CD4 expression in a T cell of a subject comprising providing to a subject a peptide comprising at most 80 contiguous amino acids of NS5A, wherein said peptide comprises an amino acid sequence of VDGIPV(S/E)WDA(D/E)ARAPA (SEQ ID NO: 24) or (V/L)DG(I/V)X(S/H)(W/R)XA(D/P)XXXPX (SEQ ID NO: 25), wherein X is any amino acid.

20. The method of claim 19, wherein the peptide is provided by administering an expression construct encoding the peptide.

21. The method of claim 19, wherein the NS5A peptide further comprises a targeting domain.

22. The method of claim 21, wherein the targeting domain is a nuclear targeting signal.

23. Then method of claim 21, wherein the targeting domain targets the endoplasmic reticulum.

24. The method of claim 21, wherein the targeting domain targets a cell surface receptor.

25. The method of claim 24, wherein the cell surface receptor is the CD4 receptor.

26. A method for modulating T cell function, modulating chemokine product by a T cell, or inhibiting apoptosis in a T cell, comprising contacting a T cell with a flavivirus NS5A peptide comprising at most 80 contiguous amino acids of NS5A, wherein said peptide comprises an amino acid sequence of VDGIPV(S/E)WDA(D/E)ARAPA (SEQ ID NO: 24) or (V/L)DG(I/V)X(S/H)(W/R)XA(D/P)XXXPX (SEQ ID NO: 25), wherein X is any amino acid.

27. The method of claim 26, wherein the peptide is encoded by an expression construct.

28. The method of claim 26, wherein the peptide further comprises a targeting domain.

29. The method of claim 26, wherein said T cell is in a subject.

30. The method of claim 29, wherein said subject suffers from or is at risk of an allergic reaction, suffers from or is at risk of an autoimmune disease, or is or will be a transplant recipient.

31. The method of claim 28, wherein the targeting domain is a nuclear targeting signal.

32. Then method of claim 28, wherein the targeting domain targets the endoplasmic reticulum.

33. The method of claim 28, wherein the targeting domain targets a cell surface receptor.

34. The method of claim 33, wherein the cell surface receptor is the CD4 receptor.

35. The method of claim 17, wherein the targeting domain is a nuclear targeting signal.

36. Then method of claim 17, wherein the targeting domain targets the endoplasmic reticulum.

37. The method of claim 18, wherein the cell surface receptor is the CD4 receptor.

38. The method of claim 12, wherein the fusion peptide includes a targeting domain.

39. The method of claim 38, wherein the targeting domain targets the endoplasmic reticulum.

40. The method of claim 38, wherein the targeting domain targets a cell surface receptor.

41. The method of claim 40, wherein the cell surface receptor is the CD4 receptor.

* * * * *